United States Patent
Vreugde et al.

(10) Patent No.: US 11,298,364 B2
(45) Date of Patent: Apr. 12, 2022

(54) METHODS AND PRODUCTS FOR PREVENTING AND/OR TREATING MICROORGANISM INFECTIONS COMPRISING IRON CHELATORS AND NON-IRON PORPHYRINS

(71) Applicant: The University of Adelaide, Adelaide (AU)

(72) Inventors: Sarah Vreugde, North Brighton (AU); Peter John Wormald, North Adelaide (AU)

(73) Assignee: The University of Adelaide, Adelaide (AU)

( * ) Notice: Subject to any disclaimer, the term of this patent is extended or adjusted under 35 U.S.C. 154(b) by 130 days.

(21) Appl. No.: 15/755,719

(22) PCT Filed: Aug. 30, 2016

(86) PCT No.: PCT/AU2016/050811
§ 371 (c)(1),
(2) Date: Feb. 27, 2018

(87) PCT Pub. No.: WO2017/035582
PCT Pub. Date: Mar. 9, 2017

(65) Prior Publication Data
US 2018/0338985 A1 Nov. 29, 2018

(30) Foreign Application Priority Data

Aug. 31, 2015 (AU) .................................. 2015903523

(51) Int. Cl.
*A61K 31/4422* (2006.01)
*A61K 31/555* (2006.01)
(Continued)

(52) U.S. Cl.
CPC .......... *A61K 31/555* (2013.01); *A61K 31/409* (2013.01); *A61K 31/4422* (2013.01); *A61K 45/06* (2013.01); *A61P 31/04* (2018.01)

(58) Field of Classification Search
CPC .............. A61K 31/409; A61K 31/4422; A61K 31/555; A61P 31/04–08; A61P 31/00
See application file for complete search history.

(56) References Cited

U.S. PATENT DOCUMENTS

2001/0007868 A1* 7/2001 Facchini ................ A61K 31/00
514/185
2007/0231406 A1* 10/2007 Bucalo ................... A61K 47/38
424/617

(Continued)

OTHER PUBLICATIONS

Ballouche el al., "Iron Metabolism: A Promising Target for Antibacterial Strategies," *Recent Patents on Anti-Infective Drug Discovery*, vol. 4:190-205, 2009.

(Continued)

*Primary Examiner* — Theodore R. Howell
(74) *Attorney, Agent, or Firm* — Klarquist Sparkman, LLP

(57) ABSTRACT

The present disclosure relates to methods and products for reducing the viability of microorganisms, and to methods and products for preventing and/or treating microorganism infections. Certain embodiments of the present disclosure provide a method for reducing viability of a microorganism. The method comprises exposing the microorganism to an effective amount of an iron chelator and subsequently exposing the microorganism to an effective amount of a non-iron porphyrin, thereby reducing the viability of the microorganism.

17 Claims, 18 Drawing Sheets

(51) Int. Cl.
  *A61P 31/04*    (2006.01)
  *A61K 31/409*   (2006.01)
  *A61K 45/06*    (2006.01)

(56) References Cited

U.S. PATENT DOCUMENTS

2008/0138440 A1* 6/2008 Swaminathan ........ A61B 5/412
                                            424/617
2010/0129434 A1* 5/2010 Ibrahim ............. A61K 31/4196
                                            424/450

OTHER PUBLICATIONS

Breusing et al., "Light-induced Cytotoxicity after Aminolevulinic Acid Treatment is Mediated by Heme and not by Iron," *J. Phytochem. Photobiol. B: Biol.*, vol. 99:36-43, 2010.

Lee et al., "Concurrent Expression of Heme Oxygenase-1 and p53 in Human Retinal Pigment Epithelial Cell Line," *Biochem. Biophys. Res. Comm.*, vol. 365:870-874, 2008.

Lehmann et al., "The Heme Oxygenase 1 Product Biliverdin Interferes with Hepatitis C Virus Replication by Increasing Antiviral Interferon Response," *Hepatology.*, vol. 51:398-404, 2010.

* cited by examiner

1) Vehicle Alone
2) Def
3) GaPP
4) Def-GaPP

5) Vehicle alone
6) Def 20-GaPP 200
7) Def 20-GaPP 500

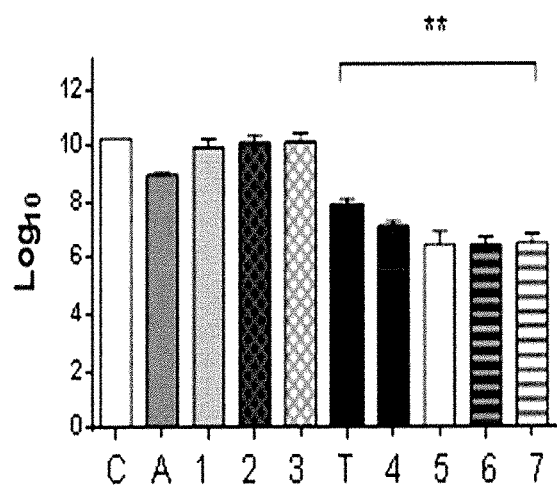
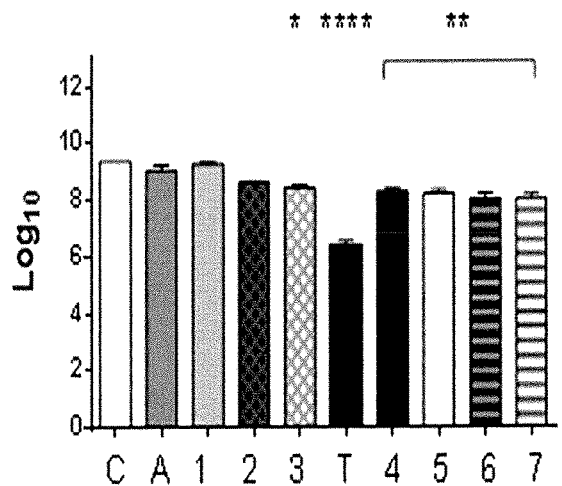
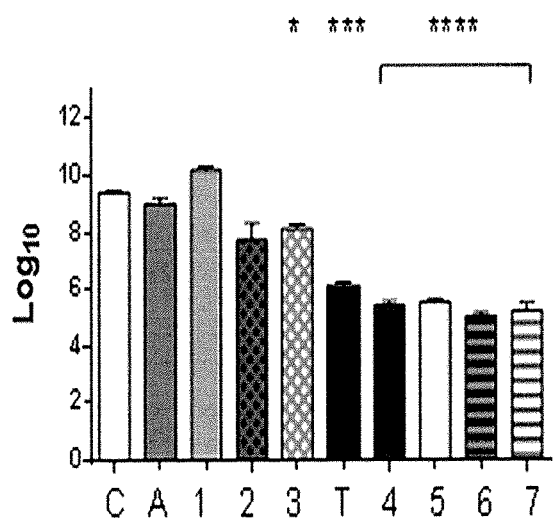
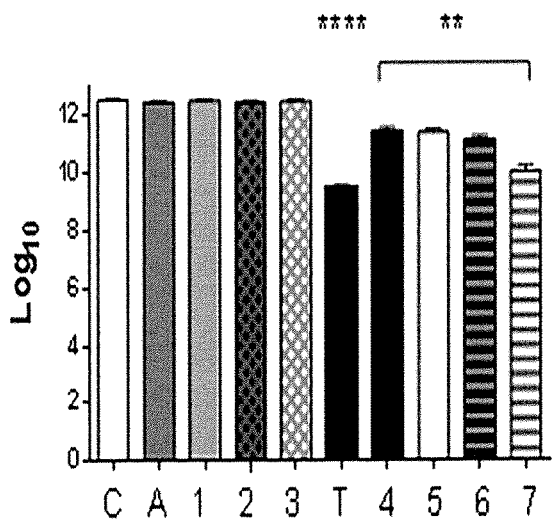
*Fig. 15*

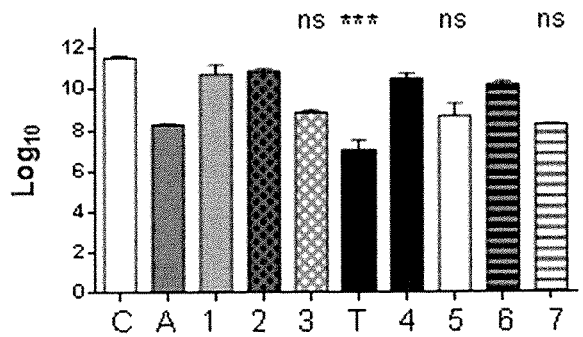
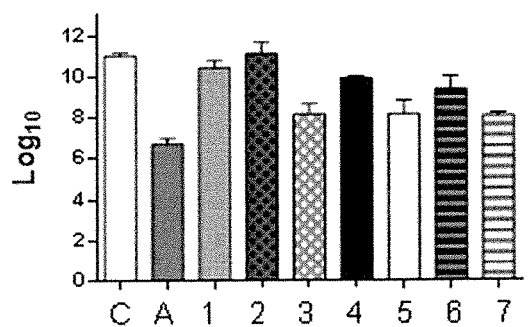
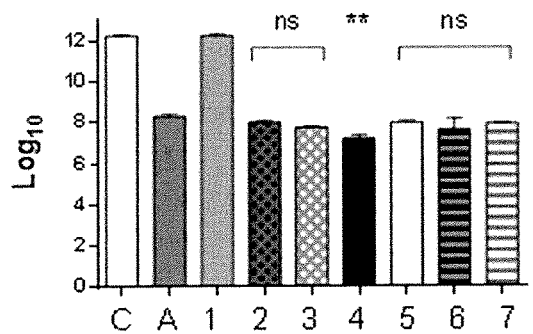
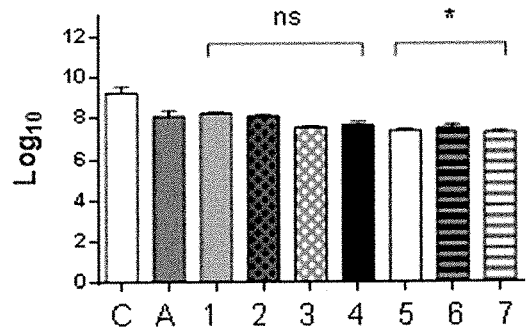
*Fig. 16*

METHODS AND PRODUCTS FOR PREVENTING AND/OR TREATING MICROORGANISM INFECTIONS COMPRISING IRON CHELATORS AND NON-IRON PORPHYRINS

PRIORITY CLAIM

This application is the U.S. National Stage of International Application No. PCT/AU2016/050811, filed on 30 Aug. 2016, published in English under PCR Article PCR Article 21(2), which claims priority to Australian Provisional Patent Application 2015903523 filed on 31 Aug. 2015, the content of which is hereby incorporated by reference.

FIELD

The present disclosure relates to methods and products for reducing the viability of microorganisms, and to methods and products for preventing and/or treating microorganism infections.

BACKGROUND

Microorganisms are responsible for a significant proportion of all disease burden. The majority of infections caused by microorganisms are due to infections by bacteria, fungi or viruses. Various anti-bacterial agents have been developed to treat some bacterial infections. Infections involving microorganisms such as fungi and viruses are often harder to treat, but anti-fungal agents and anti-viral agents do exist that can be used to treat some types of these infections. However, there is a constant need to develop new agents that target microorganisms and which can be used to treat infections, particularly due to the fact that some infections remain untreatable and/or due to the emergence of resistance in the microorganisms against the specific treatment.

For example, in the case of bacteria, the emergence and spread of bacterial resistance over the past decades has highlighted the need to develop new strategies for treating bacterial infections. Indeed, some bacteria have developed resistance to several different antibiotics, such as methicillin resistant *Staphylococcus aureus* (MRSA), presenting an acute challenge to trying to treat such infections. Because of the rise of bacterial resistance, the need for development of new anti-bacterial agents has become acute.

In addition, a further complication is that while anti-bacterial agents exist for a variety of bacteria, some bacterial infections are difficult to treat as the bacteria are resident in a biofilm, which are clusters of bacterial cells, irreversibly attached to a surface and embedded in a matrix of extracellular polymeric substances self-produced by the bacteria. The biofilm state is advantageous for bacterial survival as the biofilm acts like a protective shield, enabling the bacteria to adapt to hostile environmental conditions, evade the immune system, and ultimately to establish resistance against antimicrobials.

Bacteria residing in biofilms require up to 1000-fold higher concentrations of antimicrobial treatments than their planktonic (free-floating) counterparts. Therefore, bacterial biofilms represent one of the biggest challenges the medical community is facing. Indeed, recent data suggest that biofilms may account for over 80% of microbial infections in the body.

Clinically relevant biofilms are often microbial complex structures associated with severe and recalcitrant diseases, including chronic wounds, cystic fibrosis, and chronic rhinosinusitis. *Staphylococcus aureus* (*S. aureus*) represents one of the most notorious bacteria causing invasive, superficial, chronic and nosocomial (including methicillin resistant *S. aureus*) infections. Current intervention options include are i) treatment with antibiotics, ii) surgery and iii) long-term follow up, causing tremendous health care costs and contributing to the spread of bacterial resistance against antibiotics.

Biofilms also occur in non-biological settings, and removing contamination by microorganisms in biofilms in these settings can be difficult to achieve.

For these reasons, there is a need to develop new strategies to treat microorganism infections.

SUMMARY

The present disclosure relates to methods and products for reducing the viability of microorganisms, and to methods and products for preventing and/or treating microorganism infections.

Certain embodiments of the present disclosure provide a method for reducing viability of a microorganism, the method comprising exposing the microorganism to an effective amount of an iron chelator and subsequently exposing the microorganism to an effective amount of a non-iron porphyrin, thereby reducing the viability of the microorganism.

Certain embodiments of the present disclosure provide a method of preventing and/or treating a microorganism infection in a subject, the method comprising administering to the subject an effective amount of an iron chelator and subsequently administering to the subject an effective amount of a non-iron porphyrin, thereby preventing and/or treating the microorganism infection.

Certain embodiments of the present disclosure provide a product for the prevention and/or treatment of a microorganism infection in a subject, the product comprising the following components:

an iron chelator; and a non-iron porphyrin;

wherein the components are provided in a form for administration of the iron chelator to the subject followed by subsequent administration of the non-iron porphyrin to the subject.

Certain embodiments of the present disclosure provide an iron chelator and a non-iron porphyrin for the prevention and/or treatment of a subject having a microorganism infection.

Certain embodiments of the present disclosure provide use of an iron chelator and a non-iron porphyrin for the prevention and/or treatment of a microorganism infection in a subject.

Certain embodiments of the present disclosure provide use of an iron chelator and a non-iron porphyrin for the prevention and/or treatment of a subject having an infection associated with a bacterial biofilm.

Certain embodiments of the present disclosure provide use of an iron chelator and a non-iron porphyrin for the prevention and/or treatment of a subject having a microorganism infection in a subject, wherein the iron chelator is provided in an immediate or sustained release form and the non-iron porphyrin is provided in a delayed release form.

Certain embodiments of the present disclosure provide use of an iron chelator and a non-iron porphyrin for the prevention and/or treatment of a subject having a microorganism infection in a subject wherein the non-iron porphyrin is administered subsequent to the administration of the iron chelator.

Certain embodiments of the present disclosure provide a composition comprising an iron chelator and a non-iron porphyrin, wherein the composition provides an immediate or sustained release of the iron chelator and a delayed release of the non-iron porphyrin.

Certain embodiments of the present disclosure provide a composition comprising an iron chelator, a non-iron porphyrin and an antibiotic.

Certain embodiments of the present disclosure provide a method preventing and/or treating bacterial rhinosinusitis in a subject, the method comprising topically administering to the site of infection associated with the bacterial rhinosinusitis an effective amount of an iron chelator and subsequently topically administering to the site of bacterial infection an effective amount of a non-iron porphyrin, thereby preventing and/or treating the bacterial rhinosinusitis in the subject.

Certain embodiments of the present disclosure provide a method of treating an infected wound in a subject, the method comprising topically administering to the wound an effective amount of an iron chelator and subsequently topically administering to the wound an effective amount of a non-iron porphyrin, thereby treating the infected word in the subject.

Certain embodiments of the present disclosure provide a method of preventing and/or treating bacterial infection of a wound, the method comprising topically administering to the wound an effective amount of an iron chelator and subsequently topically administering to the wound an effective amount of a non-iron porphyrin, thereby preventing and/or treating infection of the wound.

Certain embodiments of the present disclosure provide a method of reducing the viability of a bacterium resistant to an antibiotic, the method comprising exposing the bacterium to an effective amount of an iron chelator and subsequently exposing the bacterium to an effective amount of a non-iron porphyrin, thereby reducing the viability of the bacterium.

Certain embodiments of the present disclosure provide use of an iron chelator and a non-iron porphyrin for preventing and/or treating an antibiotic resistant bacterial infection in a subject.

Certain embodiments of the present disclosure provide a method preventing and/or treating bacterial rhinosinusitis in a subject, the method comprising administering to the site of infection associated with the bacterial rhinosinusitis an effective amount of a topical composition comprising an iron chelator and a non-iron porphyrin, thereby preventing and/or treating the bacterial rhinosinusitis in the subject.

Certain embodiments of the present disclosure provide a method of increasing sensitivity of a bacterium to an antibiotic, the method comprising exposing the bacterium to an effective amount of an iron chelator and subsequently exposing the bacterium to an effective amount of a non-iron porphyrin, thereby increasing the sensitivity of the bacterium to the antibiotic.

Certain embodiments of the present disclosure provide a method of reducing viability of a bacterium, the method comprising:
 exposing the bacterium to an effective amount of an iron chelator and subsequently exposing the bacterium to an effective amount of a non-iron porphyrin; and
 exposing the bacterium to an antibiotic prior to, concurrent with and/or after exposure to the iron chelator.

Certain embodiments of the present disclosure provide a method of identifying a combination of agents for use to prevent and/or treat a microorganism infection, the method comprising:
 providing an iron chelator and a non-iron porphyrin;
 exposing a microorganism to the iron chelator and subsequently exposing the microorganism to the non-iron porphyrin; and
 identifying a combination of the iron chelator and the non-iron porphyrin as a combination of agents for use to prevent and/or treat a microorganism infection on the basis of the combination reducing the viability of the microorganism.

Other embodiments are disclosed herein.

BRIEF DESCRIPTION OF THE FIGURES

Certain embodiments are illustrated by the following figures. It is to be understood that the following description is for the purpose of describing particular embodiments only and is not intended to be limiting with respect to the description.

FIG. 15 shows log 10 reduction of biofilms of *S. aureus* (A) and MRSA (B), SCV 8 (C) and SCV 12 (D) after treatment exposure to Def/GaPP gels relative to ciprofloxacin-loaded gel. C: drug-free control, A: ciprofloxacin 5 μg/ml, 1: deferiprone 20 (Def in mM), 2: gallium-protoporphyrin 100 (GaPP in μg/ml), 3: Def 20+GaPP 100, T: triple gel consisting of Def 20+GaPP 100+Cip, 4: GaPP 250, 5: Def 20+GaPP 250, 6: GaPP 500, 7: Def 20+GaPP 500. Data are the mean±SD of 3 biological replicates.* $p<0.05$  $p<0.01$ * $p<0.001$ **** $p<0.0001$.

FIG. 16 shows log 10 reduction of biofilms of *P. aeruginosa* (A), *P. aeruginosa* clinical isolate (B). *S. epidermidis* (C), *Acinetobacter johnsonii* (D), after treatment exposure to Def/GaPP gels relative to ciprofloxacin-loaded gel. C: drug-free control, A: ciprofloxacin 5 μg/ml, 1: deferiprone 20 (Def in mM), 2: gallium-protoporphyrin 100 (GaPP in μg/ml), 3: Def 20+GaPP 100, T: triple gel consisting of Def 20+GaPP 100+Cip, 4: GaPP 250, 5: Def 20+GaPP 250, 6: GaPP 500, 7: Def 20+GaPP 500. Data are the mean±SD of 3 biological replicates.* $p<0.05$  $p<0.01$ * $p<0.001$ **** $p<0.0001$.

DETAILED DESCRIPTION

Figure 1:
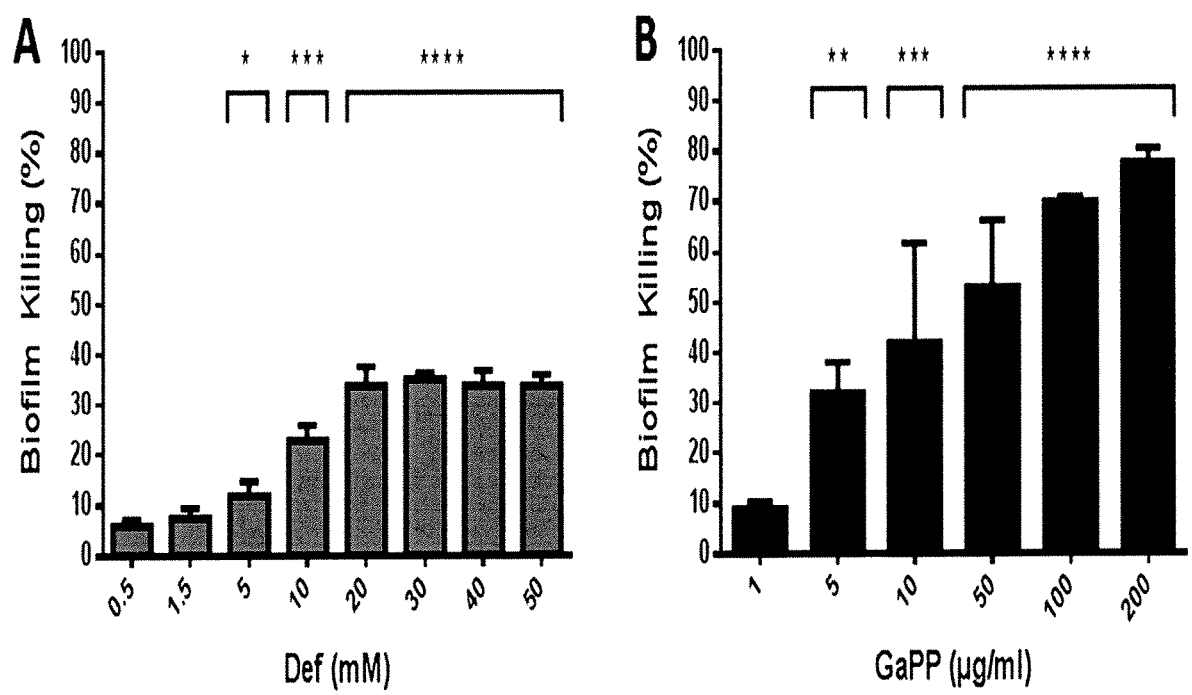
FIG. 1 shows *S. aureus* biofilm killing (%) by various concentrations of (A) Def (mM) and (B) GaPP (µg/ml) relative to controls (no treatment, i.e. 0% biofilm killing). Incubation time 2 h. The values indicate mean±SD of 3 individual plates with 4 wells for each treatment concentration, n=12. Statistical analysis: one-way ANOVA. * $p<0.05$  $p<0.01$ * $p<0.001$ **** $p<0.0001$.

The present disclosure relates to methods and products for reducing the viability of a microorganism, and to methods and products for preventing and/or treating microorganism infections.

Certain disclosed embodiments provide methods, products, compositions, and uses thereof that have one or more advantages. For example, some of the advantages of some embodiments disclosed herein include one or more of the following: identification of a new treatment regime for microorganism infections, such as bacterial infections; identification of a treatment regime that is suitable for the treatment of some bacteria in a biofilm; identification that the biocidalproperties of iron chelators can be enhanced by subsequent treatment with a non-iron porphyrin; identification that controlled release of iron chelators and non-iron porphyrins provides improved strategies for treatment of microorganisms, such as bacteria; treatment regimes that can utilise lower concentrations of agents that target microorganisms or can improve the efficacy of such agents, such as anti-bacterial agents, than when used alone; new products and compositions for the treatment of bacterial infections, including bacterial infections associated with a biofilm; new regimes for the treatment of bacteria such as *Staphylococcus* and *Pseudomonas*, particularly when present in a biofilm; products and compositions for the treatment of bacterial infections, including bacterial infections associated with a biofilm; to provide one or more advantages, or to provide a commercial alternative. Other advantages of some embodiments of the present disclosure are disclosed herein.

Certain embodiments of the present disclosure provide a method for reducing the viability of a microorganism. Methods for assessing the viability of microorganisms are known in the art.

Certain embodiments of the present disclosure provide a method for reducing viability of a microorganism, the method comprising exposing the microorganism to an effective amount of an iron chelator and subsequently exposing the microorganism to an effective amount of an agent that is an iron mimetic and/or a heme mimetic, thereby reducing the viability of the microorganism.

The term "iron mimetic" refers to an agent that is an analogue of iron and interferes with the action of iron in cells, including interfering with enzymes utilising iron, such as redox enzymes, or interferes with iron metabolism. The term "heme mimetic" refers to an agent that is an analogue of heme and interferes with heme activity, heme synthesis or heme metabolism.

In certain embodiments, the agent that is an iron mimetic and/or a heme mimetic comprises a non-iron porphyrin.

Certain embodiments of the present disclosure provide a method for reducing viability of a microorganism, the method comprising exposing the microorganism to an effective amount of an iron chelator and subsequently exposing the microorganism to an effective amount of a non-iron porphyrin, thereby reducing the viability of the microorganism.

In certain embodiments, the microorganism comprises a bacterium. In certain embodiments, the microorganism comprises a fungus or a virus. Other microorganisms are contemplated.

Examples of iron chelators include deferiprone, deferoxamine, deferasirox, tetramic acid, desferrithiocin, 8-hydroxyquinoline analogues, clioquinol, O-trensox (tris-N-(2-aminoethyl-[8-hydroxyquinoline-5-sulfonato-7-carboxamido] amine), tachpyridine (N,N',N"-tris(2-pyridylmethyl)-cis, cis-1,3,5-triaminocyclohexane), Dexrazone, Thiosemicarbazones, Triapine® (3-aminopyridine-2-carboxaldehyde thiosemicarbazone [3-AP]), pyridoxal isonicotinoyl hydrazone (PIH) and its analogs, phytochemicals, proanthocyanidins, epicatechins, flavonols and anthocyanin, curcumin, apocyanin, kolaviron, floranol, nitrilotriacetate, pycnogenol, procyanidins, baicalein, baicalin, quercetin, tetramethylpyrazine, ferulic acid, ligustrazine, quercetin, chrysin, 3-hydroxyflavone, 3',4'-dihydroxy flavone, rutin and flavones, ferrozine, gallic acid, catechin, epigallocatechin gallate (EGCG) and proanthocyanidins, green tea catechins, black tea theaflavins, ethylenediaminetetraacetic acid/ethylenediaminetetraacetate salts (EDTA), citric acid, phosphonic acid/phosphonates and its analogs, aminophosphonates and its analogs, bisphosphonates and its analogs, and/or an acceptable salt, derivative (such as a chemically substituted form), solvate, hydrate, tautomer, pro-drug, or stereoisomer of any of aforementioned. Other iron chelators are contemplated.

In certain embodiments, the method comprises exposing the microorganism to a concentration of the iron chelator as follows: 100 mM or less, 50 mM or less, 20 mM or less, 10 mM or less, 5 mM or less, 4 mM or less, 3 mM or less, 2 mM or less, 1.5 mM or less deferiprone, 1 mM or less, 0.5 mM or less, 0.4 mM or less, 0.3 mM or less, 0.2 mM or less, or 0.1 mM or less.

In certain embodiments, the iron chelator comprises deferiprone (3-hydroxy-1,2-dimethylpyridin-4(1H)-one/1,2-dimethyl-3-hydroxy-4-pyridinone) and/or an acceptable salt, derivative thereof, such as a chemically substituted form thereof, a solvate thereof, a tautomer thereof, a pro-drug thereof, or a stereoisomer thereof. Other iron chelators are contemplated.

In certain embodiments, the method comprises exposing the microorganism to 50 mM or less deferiprone, 20 mM or less deferiprone, 10 mM or less deferiprone, 5 mM or less deferiprone, 4 mM or less deferiprone, 3 mM or less deferiprone, 2 mM or less deferiprone, 1.5 mM or less deferiprone, 1 mM or less deferiprone or 0.5 mM or less deferiprone. Other concentrations are contemplated.

In certain embodiments, the method comprises exposing the microorganism to 20 mM or less deferiprone.

In certain embodiments, the microorganism comprises a bacterium and the method comprises exposing the bacterium to 50 mM or less deferiprone, 20 mM or less deferiprone, 10 mM or less deferiprone, 5 mM or less deferiprone, 4 mM or less deferiprone, 3 mM or less deferiprone, 2 mM or less deferiprone, 1.5 mM or less deferiprone, 1 mM or less deferiprone or 0.5 mM or less deferiprone.

In certain embodiments, the microorganism comprises a bacterium and the method comprises exposing the bacterium to 20 mM or less deferiprone.

In certain embodiments, the method comprises exposing the microorganism to a concentration of deferiprone in the range from 0.1 to 50 mM, 0.2 to 50 mM, 0.3 to 50 mM, 0.4 to 50 mM, 0.5 to 50 mM, 1.0 to 50 mM, 1.5 to 50 mM, 2.0 to 50 mM, 3.0 to 50 mM, 4.0 to 50 mM, 5.0 to 50 mM, 10 to 50 mM, 20 to 50 mM, 30 to 50 mM, 40 to 50 mM, 0.1 to 40 mM, 0.2 to 40 mM, 0.3 to 40 mM, 0.4 to 40 mM, 0.5 to 40 mM, 1.0 to 40 mM, 1.5 to 40 mM, 2.0 to 40 mM, 3.0 to 40 mM, 4.0 to 40 mM, 5.0 to 40 mM, 10 to 40 mM, 20 to 40 mM, 30 to 40 mM, 0.1 to 30 mM, 0.2 to 30 mM, 0.3 to 30 mM, 0.4 to 30 mM, 0.5 to 30 mM, 1.0 to 30 mM, 1.5 to 30 mM, 2.0 to 30 mM, 3.0 to 30 mM, 4.0 to 30 mM, 5.0 to 30 mM, 10 to 30 mM, 20 to 30 mM, 0.1 to 20 mM, 0.2 to 20 mM, 0.3 to 20 mM, 0.4 to 20 mM, 0.5 to 20 mM, 1.0 to 20 mM, 1.5 to 20 mM, 2.0 to 20 mM, 3.0 to 20 mM, 4.0 to 20 mM, 5.0 to 20 mM, 10 to 20 mM, 0.1 to 10 mM, 0.2 to 10 mM, 0.3 to 10 mM, 0.4 to 10 mM, 0.5 to 10 mM, 1.0 to 10 mM, 1.5 to 10 mM, 2.0 to 10 mM, 3.0 to 10 mM, 4.0 to 10 mM, 5.0 to 10 mM, 0.1 to 5 mM, 0.2 to 5 mM, 0.3 to 5 mM, 0.4 to 5 mM, 0.5 to 5 mM, 1.0 to 5 mM, 1.5 to 5 mM, 2.0 to 5 mM, 3.0 to 5 mM, 4.0 to 5 mM, 0.1 to 4 mM, 0.2 to 4 mM, 0.3 to 4 mM, 0.4 to 4 mM, 0.5 to 4 mM, 1.0 to 4 mM, 1.5 to 4 mM, 2.0 to 4 mM, 3.0 to 4 mM, 0.1 to 3 mM, 0.2 to 3 mM, 0.3 to 3 mM, 0.4 to 3 mM, 0.5 to 3 mM, 1.0 to 3 mM, 1.5 to 3 mM, 2.0 to 3 mM, 0.1 to 2 mM, 0.2 to 2 mM, 0.3 to 2 mM, 0.4 to 2 mM, 0.5 to 2 mM, 1.0 to 2 mM, 1.5 to 2 mM, 0.1 to 1.5 mM, 0.2 to 1.5 mM, 0.3 to 1.5 mM, 0.4 to 1.5 mM, 0.5 to 1.5 mM, 1.0 to 1.5 mM, 0.1 to 1 mM, 0.2 to 1 mM, 0.3 to 1 mM, 0.4 to 1 mM, 0.5 to 1 mM, 0.1 to 0.5 mM, 0.2 to 0.5 mM, 0.3 to 0.5 mM, 0.4 to 0.5 mM, 0.1 to 0.4 mM, 0.2 to 0.4 mM, 0.3 to 0.4 mM, 0.1 to 0.3 mM, 0.2 to 0.3 mM, or 0.1 to 0.2 mM. Other ranges are contemplated.

In certain embodiments, the microorganism comprises a bacterium and the method comprises exposing the bacterium to a concentration of deferiprone in the range from 0.1 to 50 mM, 0.2 to 50 mM, 0.3 to 50 mM, 0.4 to 50 mM, 0.5 to 50 mM, 1.0 to 50 mM, 1.5 to 50 mM, 2.0 to 50 mM, 3.0 to 50 mM, 4.0 to 50 mM, 5.0 to 50 mM, 10 to 50 mM, 20 to 50 mM, 30 to 50 mM, 40 to 50 mM, 0.1 to 40 mM, 0.2 to 40 mM, 0.3 to 40 mM, 0.4 to 40 mM, 0.5 to 40 mM, 1.0 to 40 mM, 1.5 to 40 mM, 2.0 to 40 mM, 3.0 to 40 mM, 4.0 to 40 mM, 5.0 to 40 mM, 10 to 40 mM, 20 to 40 mM, 30 to 40 mM, 0.1 to 30 mM, 0.2 to 30 mM, 0.3 to 30 mM, 0.4 to 30 mM, 0.5 to 30 mM, 1.0 to 30 mM, 1.5 to 30 mM, 2.0 to 30 mM, 3.0 to 30 mM, 4.0 to 30 mM, 5.0 to 30 mM, 10 to 30 mM, 20 to 30 mM, 0.1 to 20 mM, 0.2 to 20 mM, 0.3 to 20 mM, 0.4 to 20 mM, 0.5 to 20 mM, 1.0 to 20 mM, 1.5 to 20 mM, 2.0 to 20 mM, 3.0 to 20 mM, 4.0 to 20 mM, 5.0 to 20 mM, 10 to 20 mM, 0.1 to 10 mM, 0.2 to 10 mM, 0.3 to 10 mM, 0.4 to 10 mM, 0.5 to 10 mM, 1.0 to 10 mM, 1.5 to 10 mM, 2.0 to 10 mM, 3.0 to 10 mM, 4.0 to 10 mM, 5.0 to 10 mM, 0.1 to 5 mM, 0.2 to 5 mM, 0.3 to 5 mM, 0.4 to 5 mM, 0.5 to 5 mM, 1.0 to 5 mM, 1.5 to 5 mM, 2.0 to 5 mM, 3.0 to 5 mM, 4.0 to 5 mM, 0.1 to 4 mM, 0.2 to 4 mM, 0.3 to 4 mM, 0.4 to 4 mM, 0.5 to 4 mM, 1.0 to 4 mM, 1.5 to 4 mM, 2.0 to 4 mM, 3.0 to 4 mM, 0.1 to 3 mM, 0.2 to 3 mM, 0.3 to 3 mM, 0.4 to 3 mM, 0.5 to 3 mM, 1.0 to 3 mM, 1.5 to 3 mM, 2.0 to 3 mM, 0.1 to 2 mM, 0.2 to 2 mM, 0.3 to 2 mM, 0.4 to 2 mM, 0.5 to 2 mM, 1.0 to 2 mM, 1.5 to 2 mM, 0.1 to 1.5 mM, 0.2 to 1.5 mM, 0.3 to 1.5 mM, 0.4 to 1.5 mM, 0.5 to 1.5 mM, 1.0 to 1.5 mM, 0.1 to 1 mM, 0.2 to 1 mM, 0.3 to 1 mM, 0.4 to 1 mM, 0.5 to 1 mM, 0.1 to 0.5 mM, 0.2 to 0.5 mM, 0.3 to 0.5 mM, 0.4 to 0.5 mM, 0.1 to 0.4 mM, 0.2 to 0.4 mM, 0.3 to 0.4 mM, 0.1 to 0.3 mM, 0.2 to 0.3 mM, or 0.1 to 0.2 mM. Other ranges are contemplated.

In certain embodiments, the agent that is an iron mimetic and/or a heme mimetic comprises a non-iron porphyrin.

The term "porphyrin" as used herein refers to a molecule based on a porphyrin structure, and includes derivatives thereof.

In certain embodiments, the non-iron porphyrin comprises a non-iron metalloporphyrin. In certain embodiments, the non-iron porphyrin comprises a non-iron metalloprotoporphyrin.

The term "non-iron metalloporphyrin" refers to an non-iron containing agent having a porphyrin group coordinated to a metal ion (M), as follows:

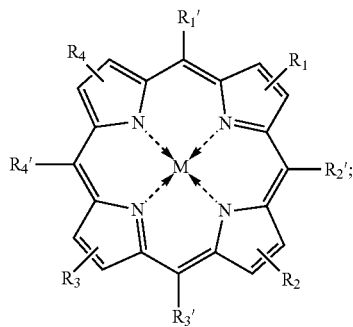

wherein M is a metal ion, and any one or more of R1 to R4 and/or any one or more of R1' t R4' are the same or a different group.

In certain embodiments, the non-iron porphyrin comprises one or more of a gallium protoporphyrin, a manganese protoporphyrin, a zinc protoporphyrin, an indium protoporphyrin, a cobalt protoporphyrin, a ruthenium protoporphyrin, a silver protoporphyrin or a copper protoporphyrin.

In certain embodiments, the non-iron porphyrin comprises a gallium protoporphyrin.

In certain embodiments, the non-iron porphyrin comprises a compound with the following structure:

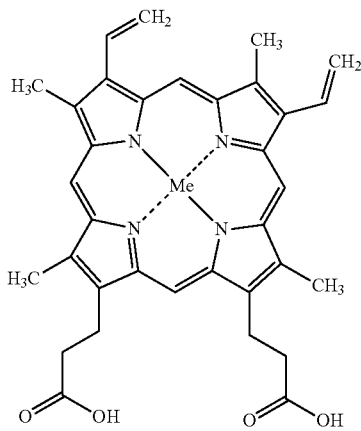

wherein Me is selected from gallium, manganese, zinc, indium, cobalt, ruthenium, silver and copper; and/or an acceptable salt, substituted derivative, solvate, tautomer or stereoisomer thereof. In certain embodiments, Me is gallium.

In certain embodiments, the method comprises exposing the microorganism to a concentration of the agent that is an iron mimetic and/or a heme mimetic as follows: 100 mM or less, 50 mM or less, 20 mM or less, 10 mM or less, 5 mM or less, 4 mM or less, 3 mM or less, 2 mM or less, 1.5 mM or less deferiprone, 1 mM or less, 0.5 mM or less, 0.4 mM or less, 0.3 mM or less, 0.2 mM or less, or 0.1 mM or less.

In certain embodiments, the method comprises exposing the microorganism to a concentration of the agent that is an iron mimetic and/or a heme mimetic as follows: 1 mg/ml or less, 500 μg/ml or less 200 μg/ml or less, 100 μg/ml or less, 50 μg/ml or less, 25 μg/ml or less, 10 μg/ml or less, 5 μg/ml or less, or 1 μg/ml or less.

In certain embodiments, the method comprises exposing the microorganism to 200 μg/ml or less, 100 μg/ml or less, 50 μg/ml or less, 25 μg/ml or less, 10 μg/ml or less, 5 μg/ml or less, or 1 μg/ml or less of a non-iron porphyrin.

In certain embodiments, the method comprises exposing the microorganism to 200 μg/ml or less of a non-iron porphyrin.

In certain embodiments, the microorganism comprises a bacterium and the method comprises exposing the microorganism to 200 μg/ml or less, 100 μg/ml or less, 50 μg/ml or less, 25 μg/ml or less, 10 μg/ml or less, 5 μg/ml or less, or 1 μg/ml or less of a non-iron porphyrin.

In certain embodiments, the method comprises exposing the microorganism to a concentration of a non-iron porphyrin in the range from 1 to 200 μg/ml, 5 to 200 μg/ml, 10 to 200 μg/ml, 25 to 200 μg/ml, 50 to 200 μg/ml, 100 to 200 μg/ml, 1 to 100 μg/ml, 5 to 100 μg/ml, 10 to 100 μg/ml, 25 to 100 μg/ml, 50 to 100 μg/ml, 1 to 50 μg/ml, 5 to 50 μg/ml, 10 to 500 μg/ml, 25 to 50 μg/ml, 1 to 25 μg/ml, 5 to 25 μg/ml, 10 to 25 μg/ml, 1 to 10 μg/ml, 5 to 10 μg/ml, or 1 to 5 μg/ml.

In certain embodiments, the microorganism comprises a bacterium and the method comprises exposing the microorganism to a concentration of a non-iron porphyrin in the range from 1 to 200 μg/ml, 5 to 200 μg/ml, 10 to 200 μg/ml, 25 to 200 μg/ml, 50 to 200 μg/ml, 100 to 200 μg/ml, 1 to 100 μg/ml, 5 to 100 μg/ml, 10 to 100 μg/ml, 25 to 100 μg/ml, 50 to 100 μg/ml, 1 to 50 μg/ml, 5 to 50 μg/ml, 10 to 500 μg/ml, 25 to 50 μg/ml, 1 to 25 μg/ml, 5 to 25 μg/ml, 10 to 25 μg/ml, 1 to 10 μg/ml, 5 to 10 μg/ml, or 1 to 5 μg/ml.

Certain embodiments of the present disclosure provide use of an iron chelator and a non-iron porphyrin as described herein.

In certain embodiments, the method reduces the viability of a bacterium resistant to one or more antibiotics.

In certain embodiments, the method reduces the viability of a small colony variant of a bacterium, or an antibiotic resistant variant of the bacterium.

In certain embodiments, the microorganism is present in vitro.

In certain embodiments, the microorganism is present is a non-biological setting, such as being present in/on a device, a system, a container, a fluid, or a site. For example, the method may be used to treat a medical device, or to treat a water storage container or water pipes.

In certain embodiments, the microorganism is present in an instrument, a device or an implant which is potentially contaminated with a microorganism (such as a bacterium) for use in a subject and as such may need to be treated prior to use, so as to eliminate the microorganism and/or to reduce the likelihood of the subject becoming infected with the microorganism. Examples include catheters, intravenous catheters, vascular prosthesis, cerebrospinal fluid shunts, prosthetic heart valves, urinary catheters, joint prostheses and orthopaedic fixation devices, cardiac pacemakers, peritoneal dialysis catheters, intrauterine devices, biliary tract stents, dentures, breast implants, and contact lenses. Such devices may, for example, be treated with a solution of an iron chelator and subsequently treated with a solution of a non-iron porphyrin prior to use.

In certain embodiments, the microorganism is present in a biological setting.

In certain embodiments, the microorganism is present in vitro in a biological setting.

In certain embodiments, the microorganism is present in a biological system. The term "biological system" refers to a cellular system and includes one or more cells in vivo, ex vivo, in vitro; a tissue or organ in vivo or ex vivo, or an entire subject. In certain embodiments, the biological system comprises one or more cells in vitro, one or more cells in culture, one or more cells ex vivo, a tissue or organ, or a human or animal subject.

In certain embodiments, the microorganism is present in vivo. In certain embodiments, a subject is infected with the microorganism.

In certain embodiments, the subject is a human subject, a mammalian subject, a livestock animal (such as a horse, a cow, a sheep, a goat, a pig), a domestic animal (such as a dog or a cat) and other types of animals such as primates, rabbits, rats, mice, birds and laboratory animals. Other types of animals are contemplated. Veterinary applications of the present disclosure are contemplated.

In certain embodiments, the method is used in treatment regimes that are beneficial for wound healing, treatment regimes that are beneficial for wound healing of an infected wound, treatment regimes that are beneficial for wound healing where the wound occurs during surgery (eg abdominal surgery, sinus surgery) or is a burn wound, treatment regimes that are beneficial for wound healing of chronic wounds, diabetic wounds and/or diabetic ulcers. Methods for assessing the efficacy of treatments are known in the art.

In certain embodiments, the method is used in treatment regimes during and/or post surgery, such as to reduce the likelihood of infection of surgical wounds. For example, the method may be used in treatment regimes post-abdominal surgery to assisting with reducing the likelihood of infection post surgery, or during and/or post sinus surgery.

Methods for assessing the viability of microorganisms are known in the art.

In certain embodiments, the method is used to reduce the viability of one or more microorganisms. In certain embodiments, the method is used to kill one or more microorganisms.

In certain embodiments, the method reduces the viability of the microorganisms by 50% or more, by 60% or more, by 70% or more, by 80% or more, by 90% or more, by 95% or more, by 99% or more, by 99.9% or more, by 99.99% or more, or by 99.999% or more. In certain embodiments, the method comprises reducing the viability of the microorganism by 10 fold or more, by 100 fold or more, by 1000 fold or more, by $10^4$ fold or more, by $10^5$ fold or more, or by $10^6$ fold or more. Other levels of reduction of viability are contemplated.

In certain embodiments, the method substantially kills all the microorganisms. In certain embodiments, the method reduces the viability of microorganisms to below detectable levels. In certain embodiments, the method reduces the viability of microorganisms to below a clinically relevant level.

In certain embodiments, the microorganism comprises a fungus. Examples of fungal species include *Aspergillus, Alternaria, Candida, Malassezia, Fusarium, Penicillium, Curvularia, Cryptococcus, Histoplasma, Paracoccidioides, Pneumocystis, Pythium, Rhizopus, Trichosporon, Aureobasidium, Cladosporium, Ulocladium, Engodontium,* and *Trichtophyton*. Other fungi are contemplated.

In certain embodiments, the microorganism comprises a virus. Examples of viruses include Adenovirus, Influenza virus, respiratory syncytial virus (RSV), Rhinovirus, Parainfluenza, Coronavirus, Human Papillomavirus, HIV-1, Cytomegalovirus, Enterovirus, Human metapneumoviruses, vaccinia virus, herpes simplex virus 1 and hepatitis B virus, hepatitis A virus, hepatitis C virus, haemorrhagic arenaviruses, canine and feline parvoviruses and mouse mammary tumour virus. Other types of viruses are contemplated.

In certain embodiments, the microorganism comprises a microorganism selected from the following species or genus: *Rhizobia, Bordetella, Shigella, E. coli, Vibrio, Aeromonas, Francisella Tularensis, Bacteroides, Campylobacter jejuni, Cyanobacteria, Bacillus subtilis, Staphylococcus epidermidis, Staphylococcus aureus, Neisseria, Pseudomonas aeruginosa, Salmonella, Helicobacter pylori, Haemophilus influenza, Corynebacterium, Mycobacterium, Streptomyces* and *Saccharomyces, Acinetobacter, Proteus, Salmonella, Streptococcus, Moraxella, Clostridium, Klebsiella, Chlamydia, Legionella, Pasteurella, Escherichia,* and *Enterobacter.*

In certain embodiments, the microorganism comprises a bacterium. In certain embodiments, the microorganism comprises a Gram positive bacterium, a Gram negative bacterium, Gram test non-responsive bacteria, aerobic bacteria, or anaerobic bacteria.

In certain embodiments, the bacterium is a small colony variant of a bacterium, or an antibiotic resistant variant of the bacterium, such as small colony variant of a *Staphylococcus* spp or a *Pseudomonas* spp.

Examples of genera or species of bacteria include *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erysipelothrix, Escherichia, Eubacterium, Ewingella, Exiguobacterium, Facklamia, Filifactor, Flavimonas, Flavobacterium, Francisella, Fusobacterium, Gardnerella, Globicatella, Gemella, Gordona, Haemophilus, Hafnia, Helicobacter, Helococcus, Holdemania, Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia,*

*Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella*; Gram-positive bacteria such as, *M. tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies paratuberculosis, *Staphylococcus aureus, Staphylococcus epidermidis, Staphylococcus aqui, Streptococcus pyogenes, Streptococcus agalactiae, Listeria monocytogenes, Listeria ivanovii, Bacillus anthracis, B. subtilis, Nocardia asteroides, Actinomyces israelii, Propionibacterium acnes,* and *Enterococcus* species and Gram-negative bacteria such as *Clostridium tetani, Clostridium perfringens, Clostridium botulinum, Pseudomonas aeruginosa, Vibrio cholerae, Actinobacillus pleuropneumonias, Pasteurella haemolytica, Pasteurella multocida, Legionella pneumophila, Salmonella typhi, Brucella abortus, Chlamydi trachomatis, Chlamydia psittaci, Coxiella bumetti, Escherichia coli, Neiserria meningitidis, Neiserria gonorrhea, Haemophilus influenzae, Haemophilus ducreyi, Yersinia pestis, Yersinia enterolitica, Escherichia coli, E. hirae, Burkholderia cepacia, Burkholderia pseudomallei, Francisella tularensis, Bacteroides fragilis, Fusobascterium nucleatum,* and *Cowdria ruminantium.* Other types of bacteria are contemplated. In certain embodiments, the bacteria comprises one or more of *Enterococcus faecalis, Staphylococcus aureus, Staphylococcus epidermidis, Streptococcus viridans, Escherichia coli, Klebsiella pneumoniae, Proteus mirabilis, Pseudomonas aeruginosa,* and a small colony variant or an antibiotic resistant variant of any of the aforementioned In certain embodiments, the microorganism comprises a bacterium of the genus *Staphylococcus*, or a small colony variant or antibiotic resistant variant thereof. In certain embodiments, the microorganism comprises *Staphylococcus aureus* or a small colony variant or antibiotic resistant variant thereof.

In certain embodiments, the microorganism comprises a bacterium of the genus *Pseudomonas* or a small colony variant or antibiotic resistant variant thereof. In certain embodiments, the microorganism comprises *Pseudomonas aeruginosa* or a small colony variant or antibiotic resistant variant thereof.

In certain embodiments, the microorganism comprises a microorganism selected from the following genus: *Staphylococcus, Pseudomonas* or *Acinetobacter* or a small colony variant or antibiotic resistant variant of any of the aforementioned.

In certain embodiments, the microorganism comprises *Staphylococcus aureus* or *Staphylococcus epidermidis*. In certain embodiments, the microorganism comprises *Pseudomonas aeruginosa*. In certain embodiments, the microorganism comprises *Acinetobacter johnsonii*.

In certain embodiments, the microorganism comprises an antibiotic resistant microorganism. In certain embodiments, the microorganism comprises a bacterium resistant to one or more antibiotics.

In certain embodiments, a method as described herein increases the sensitivity of a bacterium to an antibiotic. In certain embodiments, the increasing of the sensitivity reduces the effective concentration of an antibiotic required to reduce the viability of the bacterium.

Certain embodiments of the present disclosure provide a method of increasing sensitivity of a bacterium to an antibiotic, the method comprising exposing the bacterium to an effective amount of an iron chelator and subsequently exposing the bacterium to an effective amount of a non-iron porphyrin, thereby increasing the sensitivity of the bacterium to the antibiotic.

Examples of antibiotics are as described herein.

In certain embodiments, a method as described herein reduces the viability of a bacterium resistant to one or more antibiotics.

Certain embodiments of the present disclosure provide a method of reducing the viability of a bacterium resistant to an antibiotic, the method comprising exposing the bacterium to an effective amount of an iron chelator and subsequently exposing the bacterium to an effective amount of a non-iron porphyrin, thereby reducing the viability of the bacterium.

Examples of antibiotics are as described herein.

Certain embodiments of the present disclosure provide use of an iron chelator and a non-iron porphyrin for preventing and/or treating an antibiotic resistant bacterial infection in a subject.

In certain embodiments, the antibiotic resistant bacteria are resistant to one or more antibiotics as described herein.

In certain embodiments, the microorganism comprises a bacterium that forms part of a biofilm. In certain embodiments, the microorganism comprises a bacterium associated with a bacterial infection in a subject. In certain embodiments, the microorganism comprises a bacterium associated with a bacterial infection associated with a biofilm in a subject.

Examples of bacterial infections associated with biofilms include bacterial biofilms associated urinary tract infections (eg *E. coli, Pseudomonas aeruginosa,* enterococci, *Klebsiella, Enterobacter* spp *Proteus, Serratia*), such as being responsible for persistent infections causing relapses and acute prostatitis; wounds including acute or chronic wounds (eg *S. aureus, P. aeruginosa*), lung infections (eg *P. aeruginosa*, such as occurs in patients with cystic fibrosis), chronic osteomyelitis (eg *S. aureus*), rhinosinusitis (eg *S. aureus*), urinary tract infections (eg *E. coli, P. aeruginisa*), tuberculosis (eg *M. turbulocosis*) and infections associated with foreign bodies inserted in the human body (eg *S. aureus*).

In certain embodiments, the bacterial infection comprises rhinosinusitis. In certain embodiments, the bacterial infection comprises chronic rhinosinusitis. In certain embodiments, the bacterial infection comprises acute rhinosinusitis.

In certain embodiments, the bacterial infection comprises an infected wound, a chronic wound, a diabetic wound or a diabetic ulcer. In certain embodiments, the bacterial infection comprises a post surgery infected wound or an infected wound following abdominal surgery or sinus surgery. In certain embodiments, the bacterial infection comprises a burn injury.

Methods for assessing bacterial infection are known in the art.

The term "exposing", and related terms such as "expose" and "exposure", as used herein refers to directly and/or indirectly contacting and/or treating a microorganism with an agent(s).

Methods for exposing a microorganism to an agent(s) are known in the art.

For example, a microorganism may be exposed directly to an agent(s), exposed to an agent(s) in a composition, or exposed to a pro-form of the agent(s) that is subsequently converted to the agent.

For a microorganism in vitro, the microorganism may, for example, be exposed to the agent(s) directly, or exposed to an agent(s) in a composition, such as in a liquid composition.

For a microorganism ex vivo, the microorganism may for example be exposed to the agent(s) directly or indirectly, such as a tissue or organ being perfused with a composition comprising the agent(s).

For a microorganism in vivo, the microorganism may for example be exposed to the agent(s) directly or indirectly, such as by topical application directly to a site of infection or by administration of the agent(s) to a subject.

In certain embodiments, the method comprises exposing the microorganism to the iron chelator continuously. In certain embodiments, the method comprises exposing the microorganism to the iron chelator discontinuously. In certain embodiments, the method comprises exposing the microorganism with a decreasing amount of the iron chelator with time. In certain embodiments, the method comprises exposing the microorganism to the iron chelator with an increasing amount of the iron chelator with time.

In certain embodiments, the method comprises exposing the microorganism to one or more repeated or continuing doses of the iron chelator.

In certain embodiments, the method comprises exposing the microorganism to the agent that is an iron mimetic and/or a heme mimetic 2 hours or greater after exposing the microorganism to the iron chelator.

In certain embodiments, the method comprises exposing the microorganism to the non-iron porphyrin 2 hours or greater after exposing the microorganism to the iron chelator.

In certain embodiments, the method comprises exposing the microorganism to the agent that is an iron mimetic and/or a heme mimetic 1 hour or greater, 2 hours or greater, 3 hours or greater, 4 hours or greater, 6 hours or greater, 8 hours or greater, 10 hours or greater, 12 hours or greater, 18 hours or greater, 24 hours or greater, 36 hours or greater, 48 hours or greater, or 72 hours or greater after exposing the microorganism to the iron chelator. Other times are contemplated.

In certain embodiments, the method comprises exposing the microorganism to the non-iron porphyrin 1 hour or greater, 2 hours or greater, 3 hours or greater, 4 hours or greater, 6 hours or greater, 8 hours or greater, 10 hours or greater, 12 hours or greater, 18 hours or greater, 24 hours or greater, 36 hours or greater, 48 hours or greater, or 72 hours or greater after exposing the microorganism to the iron chelator. Other times are contemplated.

In certain embodiments, the method comprises exposing the microorganism to the agent that is an iron mimetic and/or a heme mimetic 8 hours or greater after exposing the microorganism to the iron chelator.

In certain embodiments, the method comprises exposing the microorganism to the non-iron porphyrin 8 hours or greater after exposing the microorganism to the iron chelator.

In certain embodiments, the method comprises exposing the microorganism to the agent that is an iron mimetic and/or a heme mimetic so that the release of the iron mimetic and/or the heme mimetic from a composition occurs 1 hour or greater, 2 hours or greater, 3 hours or greater, 4 hours or greater, 6 hours or greater, 8 hours or greater, 10 hours or greater, 12 hours or greater, 18 hours or greater, 24 hours or greater, 36 hours or greater, 48 hours or greater, or 72 hours or greater after exposing the microorganism to the iron chelator.

In certain embodiments, the microorganism is associated with an infection in a subject. In certain embodiments, the method comprises administering to the subject the iron chelator and subsequently administering to the subject an agent that is an iron mimetic and/or a heme mimetic. Methods for administration are as described herein.

In certain embodiments, the microorganism is a bacterium associated with a bacterial infection.

In certain embodiments, the method comprises topical administration of the iron chelator and/or the iron mimetic or the heme mimetic to the site of a bacterial infection.

In certain embodiments, the method comprises administering to the subject the iron chelator and subsequently administering to the subject the non-iron porphyrin.

In certain embodiments, the method comprises administering to the subject a composition comprising the iron chelator and subsequently administering to the subject a composition comprising the agent that is an iron mimetic and/or a heme mimetic. In certain embodiments, the method comprises administering to the subject a composition comprising the iron chelator and subsequently administering to the subject a composition comprising the non-iron porphyrin.

In certain embodiments, the iron chelator agent is administered to the subject so as to expose a microorganism to a concentration of 0.1 nM or greater, 0.5 nM or greater, 1 nM or greater, 5 nM or greater, 10 nM or greater, 50 nM or greater, 100 nM or greater, 500 nM or greater, 1 uM or greater, 5 uM or greater, 10 uM or greater, 100 uM or greater, 500 uM or greater, 1 mM or greater, or 10 mM or greater. In certain embodiments, the method comprises exposing the microorganism to a concentration of deferiprone in the range from 0.1 to 50 mM, 0.2 to 50 mM, 0.3 to 50 mM, 0.4 to 50 mM, 0.5 to 50 mM, 1.0 to 50 mM, 1.5 to 50 mM, 2.0 to 50 mM, 3.0 to 50 mM, 4.0 to 50 mM, 5.0 to 50 mM, 10 to 50 mM, 20 to 50 mM, 30 to 50 mM, 40 to 50 mM, 0.1 to 40 mM, 0.2 to 40 mM, 0.3 to 40 mM, 0.4 to 40 mM, 0.5 to 40 mM, 1.0 to 40 mM, 1.5 to 40 mM, 2.0 to 40 mM, 3.0 to 40 mM, 4.0 to 40 mM, 5.0 to 40 mM, 10 to 40 mM, 20 to 40 mM, 30 to 40 mM, 0.1 to 30 mM, 0.2 to 30 mM, 0.3 to 30 mM, 0.4 to 30 mM, 0.5 to 30 mM, 1.0 to 30 mM, 1.5 to 30 mM, 2.0 to 30 mM, 3.0 to 30 mM, 4.0 to 30 mM, 5.0 to 30 mM, 10 to 30 mM, 20 to 30 mM, 0.1 to 20 mM, 0.2 to 20 mM, 0.3 to 20 mM, 0.4 to 20 mM, 0.5 to 20 mM, 1.0 to 20 mM, 1.5 to 20 mM, 2.0 to 20 mM, 3.0 to 20 mM, 4.0 to 20 mM, 5.0 to 20 mM, 10 to 20 mM, 0.1 to 10 mM, 0.2 to 10 mM, 0.3 to 10 mM, 0.4 to 10 mM, 0.5 to 10 mM, 1.0 to 10 mM, 1.5 to 10 mM, 2.0 to 10 mM, 3.0 to 10 mM, 4.0 to 10 mM, 5.0 to 10 mM, 0.1 to 5 mM, 0.2 to 5 mM, 0.3 to 5 mM, 0.4 to 5 mM, 0.5 to 5 mM, 1.0 to 5 mM, 1.5 to 5 mM, 2.0 to 5 mM, 3.0 to 5 mM, 4.0 to 5 mM, 0.1 to 4 mM, 0.2 to 4 mM, 0.3 to 4 mM, 0.4 to 4 mM, 0.5 to 4 mM, 1.0 to 4 mM, 1.5 to 4 mM, 2.0 to 4 mM, 3.0 to 4 mM, 0.1 to 3 mM, 0.2 to 3 mM, 0.3 to 3 mM, 0.4 to 3 mM, 0.5 to 3 mM, 1.0 to 3 mM, 1.5 to 3 mM, 2.0 to 3 mM, 0.1 to 2 mM, 0.2 to 2 mM, 0.3 to 2 mM, 0.4 to 2 mM, 0.5 to 2 mM, 1.0 to 2 mM, 1.5 to 2 mM, 0.1 to 1.5 mM, 0.2 to 1.5 mM, 0.3 to 1.5 mM, 0.4 to 1.5 mM, 0.5 to 1.5 mM, 1.0 to 1.5 mM, 0.1 to 1 mM, 0.2 to 1 mM, 0.3 to 1 mM, 0.4 to 1 mM, 0.5 to 1 mM, 0.1 to 0.5 mM, 0.2 to 0.5 mM, 0.3 to 0.5 mM, 0.4 to 0.5 mM, 0.1 to 0.4 mM, 0.2 to 0.4 mM, 0.3 to 0.4 mM, 0.1 to 0.3 mM, 0.2 to 0.3 mM, or 0.1 to 0.2 mM. Other ranges are contemplated.

In certain embodiments, the iron chelator is administered to the subject in an amount ranging from one of the following selected ranges: 1 µg/kg to 100 mg/kg; 1 µg/kg to 10 mg/kg; 1 µg/kg to 1 mg/kg; 1 µg/kg to 100 µg/kg; 1 µg/kg to 10 µg/kg; 10 µg/kg to 100 mg/kg; 10 µg/kg to 10 mg/kg; 10 µg/kg to 1 mg/kg; 10 µg/kg to 100 µg/kg; 100 µg/kg to 100 mg/kg; 100 µg/kg to 10 mg/kg; 100 µg/kg to 1 mg/kg;

1 mg/kg to 10 mg/kg; and 10 mg/kg to 100 mg/kg body weight. The dose and frequency of administration may be determined by one of skill in the art.

In certain embodiments, the agent that is an iron mimetic and/or a heme mimetic is administered to the subject so as to expose a microorganism to a concentration as follows: 100 mM or less, 50 mM or less, 20 mM or less, 10 mM or less, 5 mM or less, 4 mM or less, 3 mM or less, 2 mM or less, 1.5 mM or less deferiprone, 1 mM or less, 0.5 mM or less, 0.4 mM or less, 0.3 mM or less, 0.2 mM or less, or 0.1 mM or less.

In certain embodiments, the agent that is an iron mimetic and/or a heme mimetic is administered to the subject so as to expose a microorganism to a concentration as follows: 1 mg/ml or less, 500 µg/ml or less 200 µg/ml or less, 100 µg/ml or less, 50 µg/ml or less, 25 µg/ml or less, 10 µg/ml or less, 5 µg/ml or less, or 1 µg/ml or less.

In certain embodiments, the non-iron porphyrin is administered to the subject so as to expose a microorganism to a concentration of the non-iron porphyrin of 200 µg/ml or less, 100 µg/ml or less, 50 µg/ml or less, 25 µg/ml or less, 10 µg/ml or less, 5 µg/ml or less, or 1 µg/ml or less of a non-iron porphyrin.

In certain embodiments, the non-iron porphyrin is administered to the subject so as to expose a microorganism to a concentration of the non-iron porphyrin in the range from 1 to 200 µg/ml, 5 to 200 µg/ml, 10 to 200 µg/ml, 25 to 200 µg/ml, 50 to 200 µg/ml, 100 to 200 µg/ml, 1 to 100 µg/ml, 5 to 100 µg/ml, 10 to 100 µg/ml, 25 to 100 µg/ml, 50 to 100 µg/ml, 1 to 50 µg/ml, 5 to 50 µg/ml, 10 to 500 µg/ml, 25 to 50 µg/ml, 1 to 25 µg/ml, 5 to 25 µg/ml, 10 to 25 µg/ml, 1 to 10 µg/ml, 5 to 10 µg/ml, or 1 to 5 µg/ml.

In certain embodiments, the microorganism is a bacterium and the method further comprises exposing the bacterium to an antibiotic or an anti-bacterial agent.

Examples of antibiotics include aminoglycosides, carbapenems, cephalosporins, glycopeptides, lincoasmides, lipopeptides, macrolides, monobactams, nitrofurans, oxazolidinones, penicillins (eg. amoxillicin, amoxicillin and clavunate) peolypeptides, quinolones, fluoroquinones, sulphonamides, and tetracyclines. Antibiotics are commercially available, and methods for their use are known in the art, for example as described in "Therapeutic Guidelines—Antibiotic", Version 15, 2014, published by eTG complete.

In certain embodiments, the method comprises exposing the bacterium to a fluoroquinolone antibiotic and/or a penicillin antibiotic. In certain embodiments, the method comprises exposing the bacterium to a fluoroquinolone antibiotic and/or a penicillin antibiotic. In certain embodiments, the antibiotic comprises ciprofloxacin, amoxicillin, and/or amoxicillin and clavulanate.

In certain embodiments, the method comprises exposing the bacterium to repeating or continuing doses of the antibiotic.

In certain embodiments, the method comprises exposing the bacterium to an antibiotic prior to, concurrent with and/or after exposure to the iron chelator. In certain embodiments, the method comprises exposing the bacterium to an antibiotic prior to, concurrent with and/or after exposure to the non-iron porphyrin.

Certain embodiments of the present disclosure provide a method of reducing viability of a bacterium, the method comprising:

exposing the bacterium to an effective amount of an iron chelator and subsequently exposing the bacterium to an effective amount of a non-iron porphyrin; and exposing the bacterium to an antibiotic prior to, concurrent with and/or after exposure to the iron chelator.

In certain embodiments, the bacterium is a small colony variant of a bacterium, or an antibiotic resistant variant of the bacterium.

The agent(s) as described herein may be administered to the subject in a suitable form. In this regard, the terms "administering" or "providing" include administering the agent(s), or administering a prodrug of the agent(s), or a derivative of the agent(s) that will form a therapeutically effective amount of the agent(s) within the body of the subject. The terms include for example routes of administration that are systemic (e.g., via injection such as intravenous injection, orally in a tablet, pill, capsule, or other dosage form useful for systemic administration of pharmaceuticals), and topical (e.g., creams, solutions, gels and the like, including solutions such as mouthwashes, for topical oral administration). Other forms of administration include delivery by way of a scaffold, such as a biomaterial scaffold including a scaffold produced from collagen, hydroxyapatite, β-tricalcium phosphate or a combination thereof.

Methods for administering agents are known in the art.

The agent(s) may be administered alone or may be delivered in a mixture with other therapeutic substances and/or other substances that enhance, stabilise or maintain the activity of the agent(s). In certain embodiments, an administration vehicle (e.g., pill, tablet, implant, injectable solution, etc.) would contain the agent(s) (alone or in combination) and/or additional substance(s).

When administered to a subject, the effective dosage may vary depending upon the particular agent(s) utilized, the mode of administration, the infection, and severity thereof, as well as the various physical factors related to the subject being treated, such as the presence of co-morbidities. The daily dosages are expected to vary with route of administration, and the nature of the agent(s) administered.

In certain embodiments the methods comprise administering to the subject escalating doses of agent(s) and/or repeated doses. In certain embodiments the methods comprise administering to the subject decreasing doses of agent(s) and/or repeated doses.

In certain embodiments, the agent(s) is administered orally. In certain embodiments, the agent(s) is administered topically. In certain embodiments, the agent(s) is administered via injection, such as intravenous injection. In certain embodiments, the agent(s) is administered parenterally. In certain embodiments, the agent(s) is administered by direct introduction to the lungs, such as by aerosol administration, by nebulized administration, and by being instilled into the lung. In certain embodiments, the agent(s) is administered by implant. In certain embodiments, the agent(s) is administered by subcutaneous injection, intraarticularly, rectally, intranasally, intraocularly, vaginally, or transdermally. In certain embodiments, the agent(s) is administered by a biological or non-biological implant. In certain embodiments, the agent(s) is administered incorporated in a matrix.

"Intravenous administration" is the administration of substances directly into a vein. In certain embodiments, the agent(s) may also be administered intravenously. Compositions containing the agent(s) as described herein suitable for intravenous administration may be formulated by a skilled person, and typically contain a carrier or excipient such as isotonic saline.

"Oral administration" is a route of administration where a substance is taken through the mouth, and includes buccal, sublabial and sublingual administration, as well as enteral administration and that through the respiratory tract, unless made through e.g. tubing so the medication is not in direct contact with any of the oral mucosa. Typical forms for the oral administration of therapeutic substances includes the use of tablets or capsules.

In certain embodiments, it may be desirable to administer the agent(s) directly to the airways in the form of an aerosol. Formulations for the administration of aerosol forms are known.

In certain embodiments, the agent(s) may also be administered parenterally (such as directly into the joint space) or intraperitoneally. For example, solutions or suspensions of the agent(s) in a non-ionised form or as a pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations typically contain a preservative to prevent the growth of microorganisms.

In certain embodiments, the agent(s) may also be administered by injection. Pharmaceutical forms suitable for injectable use include sterile aqueous solutions or dispersions and sterile powders for the extemporaneous preparation of sterile injectable solutions or dispersions. The carrier can be a solvent or dispersion medium containing, for example, water, ethanol, polyol (e.g., glycerol, propylene glycol and liquid polyethylene glycol), suitable mixtures thereof, and vegetable oils.

For example, a pharmaceutical composition for intravenous use of an iron chelator may be as follows: 10-500 mg of deferiprone in isotonic saline, optionally including one or more pharmaceutically acceptable additives and/or excipients. A pharmaceutical composition for intravenous use of a non-iron porphyrin may be as follows: 10-500 mg of gallium protoporhyrin in isotonic saline, optionally including one or more pharmaceutically acceptable additives and/or excipients.

In certain embodiments, the agent(s) may also be administered transdermally. Transdermal administrations are understood to include all administrations across the surface of the body and the inner linings of bodily passages including epithelial and mucosal tissues. Such administrations may be carried out using the agent(s) as described herein, or pharmaceutically acceptable salts thereof, in lotions, creams, foams, patches, suspensions, solutions, and suppositories (rectal and vaginal).

Transdermal administration may also be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient.

In certain embodiments, the agent(s) may also be administered by way of a suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the agent(s) may be administered or delivered by way of solid or semi-solid substrate, for example being incorporated into a matrix, a scaffold or a support, such as a biodegradable matrix or support. Methods for delivering agent(s) via scaffolds are known in the art. For example, a biomaterial scaffold including a scaffold produced from collagen, hydroxyapatite, β-tricalcium phosphate or a combination thereof may be used to deliver the agent. Methods for incorporating agent(s) into such substrates are known in the art.

In certain embodiments, the agent(s) may be administered or delivered by way of an implantable composition. Methods for preparing implantable compositions are known in the art.

Additional numerous various excipients, dosage forms, dispersing agents and the like that are suitable for use in connection with the administration of the agent and/or the formulation into compositions, medicaments, or pharmaceutical compositions.

Formulations are known and described in, for example, Remington's Pharmaceutical Sciences, 17th ed., Mack Publishing Company, Easton, Pa., 1985, which is incorporated herein by reference in its entirety.

In certain embodiments, the iron chelator is present in a composition, formulation or medicament in an amount ranging from one of the following selected ranges: 1 µg to 1000 mg, 1 µg to 500 mg; 1 µg to 250 mg; 1 µg to 100 mg; 1 µg to 10 mg; 1 µg to 1 mg; 1 µg to 100 µg; 1 µg to 10 µg; 10 µg to 1000 mg; 10 µg to 500 mg; 10 µg to 250 mg, 10 µg to 10 mg; 10 µg to 1 mg; 10 µg to 100 µg; 100 µg to 1000 mg; 100 µg to 500 mg, 100 µg to 250 mg, 100 µg to 100 mg; 100 µg to 10 mg; 100 µg to 1 mg; 1 mg to 1000 mg, 1 mg to 500 mg, 1 mg to 250 mg, 1 mg to 100 mg; 1 mg to 10 mg, 10 mg to 1000 mg; 10 mg to 500 mg, 10 mg to 250 mg, 10 mg to 100 mg, 100 mg to 1000 mg, 100 mg to 500 mg, 100 mg to 250 mg, and 500 mg to 100 mg. Other amounts are contemplated.

In certain embodiments, the agent that is an iron mimetic and/or a heme mimetic is present in a composition, formulation or medicament in an amount ranging from one of the following selected ranges: 1 µg to 1000 mg, 1 µg to 500 mg; 1 µg to 250 mg; 1 µg to 100 mg; 1 µg to 10 mg; 1 µg to 1 mg; 1 µg to 100 µg; 1 µg to 10 µg; 10 µg to 1000 mg; 10 µg to 500 mg; 10 µg to 250 mg, 10 µg to 10 mg; 10 µg to 1 mg; 10 µg to 100 µg; 100 µg to 1000 mg, 100 µg to 500 mg, 100 µg to 250 mg, 100 µg to 100 mg; 100 µg to 10 mg; 100 µg to 1 mg; 1 mg to 1000 mg, 1 mg to 500 mg, 1 mg to 250 mg, 1 mg to 100 mg; 1 mg to 10 mg, 10 mg to 1000 mg, 10 mg to 500 mg, 10 mg to 250 mg, 10 mg to 100 mg, 100 mg to 1000 mg, 100 mg to 500 mg, 100 mg to 250 mg and 500 mg to 1000 mg. Other amounts are contemplated.

In certain embodiments, the non-iron porphyrin is present in a composition, formulation or medicament in an amount ranging from one of the following selected ranges: 1 µg to 1000 mg, 1 µg to 500 mg; 1 µg to 250 mg; 1 µg to 100 mg; 1 µg to 10 mg; 1 µg to 1 mg; 1 µg to 100 µg; 1 µg to 10 µg; 10 µg to 1000 mg; 10 µg to 500 mg; 10 µg to 250 mg, 10 µg to 10 mg; 10 µg to 1 mg; 10 µg to 100 µg; 100 µg to 1000 mg, 100 µg to 500 mg, 100 µg to 250 mg, 100 µg to 100 mg; 100 µg to 10 mg; 100 µg to 1 mg; 1 mg to 1000 mg, 1 mg to 500 mg, 1 mg to 250 mg, 1 mg to 100 mg; 1 mg to 10 mg, 10 mg to 1000 mg, 10 mg to 500 mg, 10 mg to 250 mg, 10 mg to 100 mg, 100 mg to 1000 mg, 100 mg to 500 mg, 100 mg to 250 mg and 500 mg to 1000 mg. Other amounts are contemplated.

In certain embodiments, the method comprises administering to the subject a composition that provides an immediate or sustained release of the iron chelator.

In certain embodiments, the method comprises administering to the subject a the subject a composition that provides a continuous release of the iron chelator.

In certain embodiments, the method comprises administering to the subject repeated or continuing doses of a composition comprising an iron chelator.

In certain embodiments, the method comprises administering to the subject a composition that provides a delayed release of the agent that is an iron mimetic and/or a heme mimetic.

In certain embodiments, the method comprises administering to the subject a composition that provides a delayed release of a non-iron porphyrin agent.

In certain embodiments, the method comprises administering to the subject a composition that provides an immediate or sustained release of the iron chelator and a delayed release of the agent that is an iron mimetic and/or a heme mimetic.

In certain embodiments, the method comprises administering to the subject a composition that provides an immediate or sustained release of the iron chelator and a delayed release of the non-iron porphyrin.

In certain embodiments, the method comprises administering to the subject a composition that provides a release of the agent that is an iron mimetic and/or a heme mimetic from the composition of 1 hour or greater, 2 hours or greater, 3 hours or greater, 4 hours or greater, 6 hours or greater, 8 hours or greater, 10 hours or greater, 12 hours or greater, 18 hours or greater, 24 hours or greater, 36 hours or greater, 48 hours or greater, or 72 hours or greater, after exposing the microorganism to the iron chelator.

In certain embodiments, the method comprises administering to the subject a composition that provides a release of the agent that is an iron mimetic and/or a heme mimetic from the composition of 1 hour or greater, 2 hours or greater, 3 hours or greater, 4 hours or greater, 6 hours or greater, 8 hours or greater, 10 hours or greater, 12 hours or greater, 18 hours or greater, 24 hours or greater, 36 hours or greater, 48 hours or greater, or 72 hours or greater after administration.

In certain embodiments, the method comprises administering to the subject a composition that provides a maximal release of the agent that is an iron mimetic and/or a heme mimetic from the composition of 1 hour or greater, 2 hours or greater, 3 hours or greater, 4 hours or greater, 6 hours or greater, 8 hours or greater, 10 hours or greater, 12 hours or greater, 18 hours or greater, 24 hours or greater, 36 hours or greater, 48 hours or greater, or 72 hours or greater after exposing the microorganism to the iron chelator.

In certain embodiments, the method comprises administering to the subject a composition that provides a maximal release of the agent that is an iron mimetic and/or a heme mimetic from the composition of 1 hour or greater, 2 hours or greater, 3 hours or greater, 4 hours or greater, 6 hours or greater, 8 hours or greater, 10 hours or greater, 12 hours or greater, 18 hours or greater, 24 hours or greater, 36 hours or greater, 48 hours or greater, or 72 hours or greater after administration.

In certain embodiments, the method comprises administering to the subject a composition that provides a delayed release of a non-iron porphyrin agent.

In certain embodiments, the method comprises administering to the subject a composition that provides a release of the non-iron porphyrin from the composition of 1 hour or greater, 2 hours or greater, 3 hours or greater, 4 hours or greater, 6 hours or greater, 8 hours or greater, 10 hours or greater, 12 hours or greater, 18 hours or greater, 24 hours or greater, 36 hours or greater, 48 hours or greater, or 72 hours or greater after exposing the microorganism to the iron chelator.

In certain embodiments, the method comprises administering to the subject a composition that provides a release of the non-iron porphyrin of 1 hour or greater, 2 hours or greater, 3 hours or greater, 4 hours or greater, 6 hours or greater, 8 hours or greater, 10 hours or greater, 12 hours or greater, 18 hours or greater, 24 hours or greater, 36 hours or greater, 48 hours or greater, or 72 hours or greater after administration.

In certain embodiments, the method comprises administering to the subject a composition that provides a maximal release of the non-iron porphyrin of 1 hour or greater, 2 hours or greater, 3 hours or greater, 4 hours or greater, 6 hours or greater, 8 hours or greater, 10 hours or greater, 12 hours or greater, 18 hours or greater, 24 hours or greater, 36 hours or greater, 48 hours or greater, or 72 hours or greater after exposing the microorganism to the iron chelator. In certain embodiments, the composition provide a $T_{max}$ of one or the aforementioned times.

In certain embodiments, the method comprises administering to the subject a composition that provides a maximal release of the non-iron porphyrin of 1 hour or greater, 2 hours or greater, 3 hours or greater, 4 hours or greater, 6 hours or greater, 8 hours or greater, 10 hours or greater, 12 hours or greater, 18 hours or greater, 24 hours or greater, 36 hours or greater, 48 hours or greater, or 72 hours or greater after administration. In certain embodiments, the composition provide a $T_{max}$ of one or the aforementioned times.

In certain embodiments, the method comprises administering to the subject a composition that provides a continuous release of the non-iron porphyrin.

In certain embodiments, the method comprises administering to the subject repeated or continuing doses of a composition comprising a non-iron porphyrin.

In certain embodiments, the method comprises administering to the subject a composition that provides a time for maximal release of the iron chelator which is less than the time for maximal release of the non-iron porphyrin.

In certain embodiments, the method comprises administering to the subject a composition that provides a time for maximal release of the non-iron porphyrin that is greater than the time for maximal release of the iron chelator.

In certain embodiments, the method further comprises administering to the subject an antibiotic. Examples of antibiotics are as described herein. Methods for using antibiotics are described herein.

In certain embodiments, the method comprises administering a composition providing a sustained or continuous release of the antibiotic.

In certain embodiments, the method comprises administering one or more repeated dosages of the antibiotic to the subject.

Formulations for controlling the release of active agents, such as immediate release formulations, sustained release formulations and delayed release formulations, are known in the art, for example as described in "Handbook of Pharmaceutical Controlled Release Technology" edited by Donald L Wise (2000) Marcel Dekker Inc., 270 Madison Avenue New York, N.Y. 10016. For example, immediate release formulations may utilise the agent for immediate release (the iron chelator) in a disintegrant such as like cross linked carboxymelhylcellulose, a sodium starch glycolate or a polyvinylpyrrolidone which provide rapid disintegration of a tablet, and delayed release formulations may utilise the delayed release agent (eg the non-iron metalloporphyrin) in a pH dependent coating of an agent using an acrylic based resin such as Eudragit S (methacrylic copolymer B, NF) and/or Eudragit L (methacrylic copolymer A, NF). Formulations that provide an immediate or sustained release of the iron chelator and a delayed release of the non-iron metalloporphyrin may be prepared by a person skilled in the art.

Certain embodiments of the present disclosure provide a composition comprising an iron chelator and an agent that is an iron mimetic and/or a heme mimetic, wherein the composition provides a delayed release of the agent that is an iron mimetic and/or a heme mimetic.

Certain embodiments of the present disclosure provide a composition comprising an iron chelator and an agent that is an iron mimetic and/or a heme mimetic, wherein the composition provides an immediate or sustained release of the iron chelator and a delayed release of the agent that is an iron mimetic and/or a heme mimetic.

Certain embodiments of the present disclosure provide a composition comprising an iron chelator and a non-iron porphyrin, wherein the composition provides a delayed release of the non-iron porphyrin.

Certain embodiments of the present disclosure provide a composition comprising an iron chelator and a non-iron porphyrin, wherein the composition provides an immediate or sustained release of the iron chelator and a delayed release of the non-iron porphyrin.

Release characteristics of compositions are as described herein.

Immediate, delayed release and sustained release formulations are known in the art. For example, an oral tablet formulation with immediate release properties for an iron chelator and delayed release properties for a non-iron metalloporphyrin may be prepared as follows:

(i) 1750 mg Deferiprone may be formulated into a powder for inclusion in a gelation capsule following excipients: microcrystalline cellulose, magnesium stearate, silicon dioxide, hypromellose, macrogol 3350 and titanium dioxide. To prepare, the deferiprone may be granulated, the granules dried and sized, blended with extragranular excipients, and then lubricated with magnesium stearate, and provided in a gelatin capsule with the enteric coated GaPP as produced below.

(ii) 700 mg of GaPP coated with Eudragit L and Eudragit S. Granules of GaPP may be prepared by dissolving polyvinylpyrrolidone in purified water, granulating the GaPP with the solution, drying and sizing the granules obtained, blending with extragranular excipients, lubricated with magnesium stearate and compressing into a suitable sized tablet core. For coating, Eudragit L 100 and Eudragit S 100 may be dispersed in isopropyl alcohol. Titanium dioxide, ferric oxide (red) and talc may be suspended in water and stirred, and the suspension added to the dispersion of Eudragit L 100 and Eudragit S 100. Triethyl citrate may then be added to the suspension, stirred for 30 minutes and coated with the suspension. The tablet core may then be coated with the suspension, and gelatin capsules filled with the deferiprone powder.

In certain embodiments, a composition as described herein is used for reducing the viability of a microorganism, as an antibacterial agent or treatment, for preventing and/or treating a microorganism infection, for treating a wound, or for treating rhinosinusitis.

In certain embodiments, a composition as described herein is a gel composition.

Certain embodiments of the present disclosure provide a gel composition comprising an iron chelator and an iron mimetic and/or a heme mimetic. Gel compositions, and methods for producing gel compositions, are as described herein.

In certain embodiments, the iron mimetic and/or the heme mimetic comprises a non-iron porphyrin.

Certain embodiments of the present disclosure provide use of a gel composition as described herein.

In certain embodiments, a gel composition as described herein is used for reducing the viability of a microorganism, as an antibacterial agent or treatment, for preventing and/or treating a microorganism infection, for treating a wound, or for treating rhinosinusitis.

In certain embodiments, a composition as described herein may further comprise an antibiotic. Examples of antibiotics are as described herein. In certain embodiments, the antibiotic comprises a fluoroquinolone antibiotic and/or a penicillin antibiotic. In certain embodiments, the antibiotic comprises ciprofloxacin, amoxicillin, or amoxicillin and clavulanate.

Certain embodiments of the present disclosure provide a composition comprising an iron chelator, a non-iron porphyrin and an antibiotic. In certain embodiments, a composition as described herein may further comprise an antibiotic. Examples of antibiotics are as described herein. In certain embodiments, the antibiotic comprises a fluoroquinolone antibiotic and/or a penicillin antibiotic. In certain embodiments, the antibiotic comprises ciprofloxacin, amoxicillin, or amoxicillin and clavulanate.

The release properties of compositions or formulations as described herein can be tested in in vitro dissolution studies (eg paddle tests) and/or the pharmacokinetic properties tested in a suitable animal model or in one or more human subjects. Such an oral formulation may be administered to a subject one or more times daily.

In certain embodiments, the composition is an anti-bacterial composition, an anti-fungal composition or an anti-viral composition. Other types of compositions are contemplated.

In certain embodiments, the composition is a topical composition, such as a gel. In certain embodiments, the composition is an oral composition, such as a tablet or capsule.

Iron chelators and agents that are an iron mimetic and/or a heme mimetic are described herein. Non-iron porphyrins are as described herein. Methods for formulating a composition that provides an immediate or sustained release of the iron chelator and/or a delayed release of an agent that is an iron mimetic and/or a heme mimetic are known in the art. In certain embodiments, the composition is a gel, such as a hydrogel.

In certain embodiments, a composition as described herein is used for reducing the viability of a microorganism. In certain embodiments, a composition as described herein is used to kill a microorganism.

In certain embodiments, a composition as described herein is used for preventing and/or treating a microorganism infection in a subject.

Certain embodiments of the present disclosure provide use of an iron chelator and an agent that is an iron mimetic and/or a heme mimetic for the prevention and/or treatment of a subject having a microorganism infection in a subject, wherein the iron chelator is provided in an immediate or sustained release form and the agent that is an iron mimetic and/or a heme mimetic is provided in a delayed release form.

Certain embodiments of the present disclosure provide use of an iron chelator and a non-iron porphyrin for the prevention and/or treatment of a subject having a microorganism infection in a subject, wherein the iron chelator is provided in an immediate or sustained release form and the non-iron porphyrin is provided in a delayed release form.

Certain embodiments of the present disclosure provide a method of preventing and/or treating a microorganism infection in a subject, the method comprising administering to the subject an effective amount of a composition as described herein.

Certain embodiments of the present disclosure provide an iron chelator and an agent that is an iron mimetic and/or a heme mimetic for the prevention and/or treatment of a subject having a microorganism infection.

Certain embodiments of the present disclosure provide an iron chelator and a non-iron porphyrin for the prevention and/or treatment of a subject having a microorganism infection.

Certain embodiments of the present disclosure provide an iron chelator and an agent that is an iron mimetic and/or a heme mimetic for the prevention and/or treatment of a microorganism infection in a subject.

Certain embodiments of the present disclosure provide an iron chelator and a non-iron porphyrin for the prevention and/or treatment of a microorganism infection in a subject.

Certain embodiments of the present disclosure provide an iron chelator and an agent that is an iron mimetic and/or a heme mimetic for the prevention and/or treatment of a subject having an infection associated with a bacterial biofilm.

Certain embodiments of the present disclosure provide an iron chelator and a non-iron porphyrin for the prevention and/or treatment of a subject having an infection associated with a bacterial biofilm.

Certain embodiments of the present disclosure provide use of an iron chelator and an agent that is an iron mimetic and/or a heme mimetic for the prevention and/or treatment of a subject having a microorganism infection in a subject, wherein the agent that is an iron mimetic and/or a heme mimetic is administered subsequent to the administration of the iron chelator.

Certain embodiments of the present disclosure provide use of an iron chelator and a non-iron porphyrin for the prevention and/or treatment of a subject having a microorganism infection in a subject, wherein the non-iron porphyrin is administered subsequent to the administration of the iron chelator.

Certain embodiments of the present disclosure provide a method of preventing and/or treating a microrganism infection in a subject.

In certain embodiments, the microorganism is a bacterium.

Examples of bacterial infections in a subject include a urinary tract infection (eg associated with *E. coli, Pseudomonas aeruginosa, enterococci, Klebsiella, Enterobacter* spp *Proteus, Serratia*), a persistent infection causing relapses and acute prostatitis; infection of a wound including acute or chronic wounds (eg associated with *S. aureus, P. aeruginosa*), post-operatve wounds, a lung infection (eg associated with *P. aeruginosa*, such as occurs in patients with cystic fibrosis), chronic osteomyelitis (eg associated with *S. aureus*), rhinosinusitis (eg associated with *S. aureus*), tuberculosis (eg associated *M. turbulocosis*) and an infection associated with foreign bodies inserted/implanted in the human body (eg *S. aureus*).

For example, the method may be used in treatment regimes that are beneficial for wound healing, treatment regimes that are beneficial for wound healing of an infected wound (such as that following abdominal surgery), treatment regimes that are beneficial for wound healing where the wound occurs during surgery or is a burn wound, treatment regimes that are beneficial for wound healing of chronic wounds, diabetic wounds and diabetic ulcers, treatment regimes that are beneficial for bacterial infections, including bacterial infections associated with a biofilm, treatment regimes that are beneficial for fungal infections, and treatment regimes for viral infections.

Certain embodiments of the present disclosure provide a method of preventing and/or treating a microorganism infection in a subject, the method comprising administering to the subject an effective amount of an iron chelator and subsequently administering to the subject an effective amount of an agent that is an iron mimetic and/or a heme, thereby preventing and/or treating the microorganism infection.

Certain embodiments of the present disclosure provide a method of preventing and/or treating a microrganism infection in a subject, the method comprising administering to the subject an effective amount of an iron chelator and subsequently administering to the subject an effective amount of a non-iron porphyrin, thereby preventing and/or treating the microorganism infection.

Certain embodiments of the present disclosure provide a method of preventing and/or treating a microrganism infection in a subject using a composition as described herein.

Certain embodiments of the present disclosure provide a method preventing and/or treating rhinosinusitis in a subject.

Certain embodiments of the present disclosure provide a method of preventing and/or treating rhinosinusitis in a subject, the method comprising administering to the subject an effective amount of an iron chelator and subsequently administering to the subject an effective amount of a non-iron porphyrin, thereby preventing and/or treating the rhinosinusitis.

In certain embodiments, the method comprises topical administration of the iron chelator and/or the non-iron porphyrin.

Certain embodiments of the present disclosure provide a method preventing and/or treating bacterial rhinosinusitis in a subject, the method comprising topically administering to the site of infection associated with the bacterial rhinosinusitis an effective amount of an iron chelator and subsequently topically administering to the site of bacterial infection an effective amount of a non-iron porphyrin, thereby preventing and/or treating the bacterial rhinosinusitis in the subject.

Certain embodiments of the present disclosure provide a method preventing and/or treating bacterial rhinosinusitis in a subject, the method comprising administering to the site of infection associated with the bacterial rhinosinusitis an effective amount of topical composition comprising an iron chelator and a non-iron porphyrin, thereby preventing and/or treating the bacterial rhinosinusitis in the subject.

Certain embodiments of the present disclosure provide use of an iron chelator and a non-iron porphyrin for preventing and/or treating bacterial rhinosinusitis in a subject.

Certain embodiments of the present disclosure provide a method of treating an infected wound in a subject.

Certain embodiments of the present disclosure provide a method of treating an infected wound in a subject, the method comprising administering to the wound an effective amount of an iron chelator and subsequently administering to the wound an effective amount of a non-iron porphyrin, thereby treating the infected word in the subject.

In certain embodiments, the method comprises topical administration of the iron chelator and/or the non-iron porphyrin.

Certain embodiments of the present disclosure provide a method of treating an infected wound in a subject, the method comprising topically administering to the wound an effective amount of an iron chelator and subsequently topically administering to the wound an effective amount of a non-iron porphyrin, thereby treating the infected word in the subject.

Certain embodiments of the present disclosure provide use of an iron chelator and a non-iron porphyrin for treating an infected wound.

Certain embodiments of the present disclosure provide a method of preventing and/or treating bacterial infection of a wound. Examples of wounds are as described herein, such as a wound arising during surgery, such as abdominal surgery.

Certain embodiments of the present disclosure provide a method of preventing and/or treating bacterial infection of a wound.

Certain embodiments of the present disclosure provide a method of preventing and/or treating bacterial infection of a wound, the method comprising administering to the wound an effective amount of an iron chelator and subsequently administering to the wound an effective amount of a non-iron porphyrin, thereby preventing and/or treating infection of the wound.

In certain embodiments, the method comprises topical administration of the iron chelator and/or the non-iron porphyrin.

In certain embodiments, the wound is a surgical wound, for example as occurs as a result of abdominal surgery or sinus surgery.

Certain embodiments of the present disclosure provide a method of preventing and/or treating bacterial infection of a wound, the method comprising topically administering to the wound an effective amount of an iron chelator and subsequently topically administering to the wound an effective amount of a non-iron porphyrin, thereby preventing and/or treating infection of the wound.

Certain embodiments of the present disclosure provide use of an iron chelator and a non-iron porphyrin for preventing and/or treating bacterial infection of a wound.

The term "preventing", and related terms such as "prevention" and "prevent", refer to obtaining a desired pharmacologic and/or physiologic effect in terms of arresting or suppressing the appearance of one or more symptoms in the subject.

The term "treatment", and related terms such as "treating" and "treat", refer to obtaining a desired pharmacologic and/or physiologic effect in terms of improving the condition of the subject, ameliorating, arresting, suppressing, relieving and/or slowing the progression of one or more symptoms in the subject, a partial or complete stabilization of the subject, a regression of the one or more symptoms, or a cure of a disease, condition or state in the subject.

Examples of microorganism infections are described herein. In certain embodiments, the microorganism infection comprises a bacterial infection, a fungal infection or a viral infection.

In certain embodiments, the microorganism infection comprises a bacterial infection. Example of bacterial infections are described herein. In certain embodiments, the microorganism infection comprises a Gram positive bacterial infection or a Gram negative bacterial infection. In certain embodiments, the microorganism infection comprises an infection with a small colony variant of a bacterium and/or an antibiotic resistant variant of a bacterium.

In certain embodiments, the microorganism infection comprises a bacterial infection associated with a bacterial biofilm.

In certain embodiments, the subject is suffering from a bacterial infection, such as bacterial biofilm infection. In certain embodiments, the subject is susceptible to a bacterial infection, such as bacterial biofilm infection. Examples of bacteria and bacterial infections are described herein.

In certain embodiments, the microorganism infection comprises a fungal infection. Examples of fungal infections are described herein and include infections associated with a fungal species such as *Aspergillus, Alternaria, Candida, Malassezia, Fusarium, Penicillium, Curvularia, Cryptococcus, Histoplasma, Paracoccidioides, Pneumocystis, Pythium, Rhizopus, Trichosporon, Aureobasidium, Cladosporium, Ulocladium, Engodontium*, and *Trichtophyton*.

In certain embodiments, the infection comprises a fungal skin or mucosal infection. In certain embodiments, the infection comprises a fungal sinonasal infection.

In certain embodiments, the microorganism infection comprises a viral infection. Examples of viral infections are described herein and include infections associated with a virus such as Adenovirus, Influenza virus, respiratory syncytial virus (RSV), Rhinovirus, Parainfluenza, Coronavirus, Human Papillomavirus, HIV-1, Cytomegalovirus, Enterovirus, Human metapneumoviruses, vaccinia virus, herpes simplex virus 1 and hepatitis B virus, hepatitis A virus, hepatitis C virus, haemorrhagic arenaviruses, canine and feline parvoviruses and mouse mammary tumour virus.

In certain embodiments, the microorganism infection comprises an infection associated with a microorganism selected from the following species or genus: *Rhizobia, Bordetella, Shigella, E. coli, Vibrio, Aeromonas, Francisella Tularensis, Bacteroides, Campylobacter jejuni, Cyanobacteria, Bacillus subtilis, Staphylococcus epidermidis, Staphylococcus aureus, Neisseria, Pseudomonas aeruginosa, Salmonella, Helicobacter pylori, Haemophilus influenza, Corynebacterium, Mycobacterium, Streptomyces* and *Saccharomyces, Acinetobacter, Proteus, Salmonella, Streptococcus, Moraxella, Clostridium, Klebsiella, Chlamydia, Legionella, Pasteurella, Escherichia, Enterobacter* and or a small colony variant or an antibiotic resistant variant of any of the aforementioned.

In certain embodiments, the microorganism infection comprises an infection associated with a microorganism selected from the genus: *Staphylococcus, Pseudomonas* or *Acinetobacter*, and or a small colony variant or an antibiotic resistant variant of any of the aforementioned.

In certain embodiments, the microorganism infection comprises a *Staphylococcus* infection. In certain embodiments, the microorganism infection comprises a *Staphylococcus aureus* infection or a *Staphylococcus epidermidis* infection, or a small colony variant or an antibiotic resistant variant thereof.

In certain embodiments, the microorganism infection comprises a *Pseudomonas* infection. In certain embodiments, the microorganism infection comprises a *Pseudomonas aeruginosa* infection or a small colony variant or an antibiotic resistant variant thereof.

In certain embodiments, the microorganism infection comprises an *Acinetobacter* infection. In certain embodiments, the microorganism infection comprises a *Acinetobacter johnsonii* infection or a small colony variant or an antibiotic resistant variant thereof.

In certain embodiments, the microorganism infection comprises rhinosinusitis.

In certain embodiments, the microorganism infection comprises chronic rhinosinusitis. In certain embodiments, the microorganism infection comprises acute rhinosinusitis.

In certain embodiments, the microorganism infection comprises an infected wound, a chronic wound, a diabetic wound or a diabetic ulcer. In certain embodiments, the microorganism infection comprises a post surgery infected wound or an infected wound following abdominal surgery. In certain embodiments, the microorganism infection comprises a burn injury.

Certain embodiments of the present disclosure provide post-surgical use of an iron chelator and a non-iron porphyrin for preventing and/or treating bacterial infection.

In certain embodiments, the subject is suffering from, or susceptible to, an infection with a microorganism as described herein.

In certain embodiments, the subject is suffering from, or susceptible to, a urinary tract infection (eg associated with *E. coli, Pseudomonas aeruginosa, enterococci, Klebsiella, Enterobacter* spp *Proteus, Serratia*), a persistent infection causing relapses and acute prostatitis; infection of a wound including acute or chronic wounds (eg associated with *S. aureus, P. aeruginosa*), a post operative infection, a lung infection (eg associated with *P. aeruginosa*, such as occurs in patients with cystic fibrosis), chronic osteomyelitis (eg associated with *S. aureus*), rhinosinusitis (eg associated with *S. aureus*), tuberculosis (eg associated *M. turbulocosis*) and an infection associated with foreign bodies inserted/implanted in the human body (eg *S. aureus*).

Methods for administering to the subject an iron chelator and an agent that is an iron mimetic and/or a heme mimetic, such as a non-iron porphyrin, are described herein.

In certain embodiments, the method comprises topical administration of the iron and/or the iron mimetic and/or heme mimetic to the site of a bacterial infection. In certain embodiments, the method comprises topical administration of the iron and/or the non-iron porphyrin to the site of a bacterial infection.

Examples of iron chelators are as described herein. In certain embodiments, the iron chelator comprises deferiprone.

In certain embodiments, the method comprises exposing microorganisms associated with the infection to 20 mM or less deferiprone. Other concentrations are as described herein.

Example of agents that are an iron mimetics and/or a heme mimetics are described herein. Examples of non-iron porphyrins are as described herein.

In certain embodiments, the non-iron porphyrin comprises a non-iron metalloporphyrin. In certain embodiments, the non-iron porphyrin comprises a non-iron metalloprotoporphyrin.

In certain embodiments, the non-iron porphyrin comprises one or more of a gallium protoporphyrin, a manganese protoporphyrin, a zinc protoporphyrin, an indium protoporphyrin, a cobalt protoporphyrin, a ruthenium protoporphyrin, a silver protoporphyrin or a copper protoporphyrin.

In certain embodiments, the method comprises exposing microorganisms associated with the infection to 200 µg/ml or less of a gallium protoporphyrin. Other concentrations are as described herein.

In certain embodiments, the method comprises administering the agent that is an iron mimetic and/or a heme mimetic to the subject 2 hours or greater after administering the iron chelator to the subject. In certain embodiments, the method comprises administering the agent that is an iron mimetic and/or a heme mimetic to the subject 8 hours or greater after administering the iron chelator to the subject.

In certain embodiments, the method comprises administering the non-iron porphyrin to the subject 2 hours or greater after administering the iron chelator to the subject. In certain embodiments, the method comprises administering the non-iron porphyrin to the subject 8 hours or greater after administering the iron chelator to the subject. Other administration regimes are contemplated.

In certain embodiments, the method comprises administering to the subject one or more compositions as described herein. In certain embodiments, a composition as described herein is a composition for topical administration. In certain embodiments, the composition is a topical composition. In certain embodiments, the composition is a gel composition.

In certain embodiments, the method comprises administering to the subject a composition comprising the iron chelator and subsequently administering to the subject a composition comprising the agent that is an iron mimetic and/or a heme mimetic.

In certain embodiments, the method comprises administering to the subject a composition comprising the iron chelator and subsequently administering to the subject a composition comprising the non-iron porphyrin.

Examples of compositions are as described herein.

In certain embodiments, the method comprises administering to the subject a composition that provides an immediate or sustained release of the iron chelator.

In certain embodiments, the method comprises administering to the subject a composition that provides a continuous release of the iron chelator.

In certain embodiments, the method comprises administering to the subject a composition that provides a delayed release of the agent that is an iron mimetic and/or a heme mimetic.

Release characteristics are as described herein.

In certain embodiments, the method comprises administering to the subject a composition that provides an immediate or sustained release of the iron chelator and a delayed release of the agent that is an iron mimetic and/or a heme mimetic.

In certain embodiments, the method comprises administering to the subject a composition that provides an immediate or sustained release of the iron chelator and a delayed release of the non-iron porphyrin.

In certain embodiments, the method further comprises administering an effective amount of an antibiotic to the subject. Examples of antibiotics are as described herein. In certain embodiments, the antibiotic comprises a fluoroquinolone antibiotic and/or a penicillin antibiotic. In certain embodiments, the antibiotic comprises ciprofloxacin, amoxicillin, or amoxicillin and clavulanate.

In certain embodiments, the methods as described herein comprise administering to a subject one or more compositions as described herein. In certain embodiments, a composition as described herein is a composition for topical administration. In certain embodiments, the composition is a topical composition. In certain embodiments, the composition is a gel composition.

Certain embodiments of the present disclosure provide a method of producing a topical composition for the treatment of a microorganism infection.

Certain embodiments of the present disclosure provide a kit.

In certain embodiments, the kit comprises one or more agents and/or instructions as described herein.

Certain embodiments of the present disclosure provide a kit for performing a method as described herein.

Certain embodiments of the present disclosure provide a product for the prevention and/or treatment of a microorganism infection in a subject.

Certain embodiments of the present disclosure provide a method preventing and/or treating rhinosinusitis in a subject, the method comprising administering to the site an effective amount of an iron chelator and subsequently administering to the subject an effective amount of a non-iron porphyrin, thereby preventing and/or treating the rhinosinusitis in the subject.

Certain embodiments of the present disclosure provide a product for the prevention and/or treatment of a microorganism infection in a subject, the product comprising the following components:

an iron chelator; and
an agent that is an iron mimetic and/or a heme mimetic;
wherein the components are provided in a form for administration of the iron chelator to the subject followed by subsequent administration of the agent that is an iron mimetic and/or a heme mimetic to the subject.

In certain embodiments, the an agent that is an iron mimetic and/or a heme mimetic comprises a non-iron porphyrin.

Certain embodiments of the present disclosure provide a product for the prevention and/or treatment of a microorganism infection in a subject, the product comprising the following components:

an iron chelator; and
a non-iron porphyrin;
wherein the components are provided in a form for administration of the iron chelator to the subject followed by subsequent administration of the non-iron porphyrin to the subject.

In certain embodiments, the product comprises a composition for administration of the iron chelator, and a composition for the administration of the non-iron protoporphyrin. Compositions are as described herein.

In certain embodiments, the product optionally comprises instructions for use of the product for preventing and/or treating a microorganism. Methods for administration are as described herein.

In certain embodiments, the product further comprises an antibiotic for administration to the subject. Examples of antibiotics are as described herein. In certain embodiments, the antibiotic comprises a fluoroquinone and/or a penicillin antibiotic. In certain embodiments, the antibiotic comprises a fluoroquinolone antibiotic and/or a penicillin antibiotic. In certain embodiments, the antibiotic comprises ciproflaxin, amoxiciilin and/or amoxicillin and clavunate.

Certain embodiments of the present disclosure provide a method for screening for a combination of agents useful for preventing and/or treating a microorganism infection. A combination of agents may then be identified.

Certain embodiments of the present disclosure provide a method of identifying a combination of agents for use to prevent and/or treat a microorganism infection, the method comprising:

providing an iron chelator and an agent that is an iron mimetic and/or a heme mimetic;
exposing a microorganism to the iron chelator and subsequently exposing the microorganism to the agent that is an iron mimetic and/or a heme mimetic; and
identifying a combination of the iron chelator and the agent that is an iron mimetic and/or a heme mimetic as a combination of agents for use to prevent and/or treat a microorganism infection on the basis of the combination reducing the viability of the microorganism.

Certain embodiments of the present disclosure provide a method of identifying a combination of agents for use to prevent and/or treat a microorganism infection, the method comprising:

providing an iron chelator and a non-iron porphyrin;
exposing a microorganism to the iron chelator and subsequently exposing the microorganism to the non-iron porphyrin; and
identifying a combination of the iron chelator and the non-iron porphyrin as a combination of agents for use to prevent and/or treat a microorganism infection on the basis of the combination reducing the viability of the microorganism.

Methods for exposing a microorganism to agents, and assessing the ability of the agents to reduce viability of the microorganism, are as described herein.

In certain embodiments, the method comprises exposing the microorganisms to the agents in vitro. In certain embodiments, the method comprises exposing the microorganisms to the agents in vivo. In certain embodiments, the method comprises using a suitable animal model.

Certain embodiments of the present disclosure provide a method for screening for a combination of agents useful for increasing the sensitivity of bacterium to an antibiotic.

Certain embodiments of the present disclosure provide a method of identifying a combination of agents for use to increase the sensitivity of a bacterium to an antibiotic, the method comprising:

providing an iron chelator and an agent that is an iron mimetic and/or a heme mimetic;
exposing a microorganism to the iron chelator and subsequently exposing the microorganism to the agent that is an iron mimetic and/or a heme mimetic; and
identifying a combination of the iron chelator and the agent that is an iron mimetic and/or a heme mimetic as a combination of agents that increase the sensitivity of a bacterium to an antibiotic, The present disclosure is further described by the following examples. It is to be understood that the following description is for the purpose of describing particular embodiments only and is not intended to be limiting with respect to the above description.

Example 1—Antibacterial Efficacy of Deferiprone and Gallium-Protoporphyrin Against *Staphylococcus aureus* Biofilms Materials and Methods (i) Culture Conditions and Biofilm Formation Single colonies of *S. aureus* ATCC 25923 (American Type Culture Collection, Manassas, Va., USA) were immersed in 0.45% saline (Sigma Aldrich, Germany), adjusted to 1.0±0.1 McFarland units ($3\times10^8$ colony forming units/ml), and diluted 1:15 in nutrient broth (Oxoid Ltd., England). The bacteria-broth mixture was added into 96-well plates at 150 µl per well (Costar®, Corning Incorporated, NY, USA). Incubation for 72 hours at 37° C. on a rotating plate set at 70 rpm (3D Gyratory Mixer, Ratek Instruments, Australia) assured extensive *S. aureus* biofilm growth.

(ii) Biofilm Treatment

Biofilms were washed twice with phosphate buffered saline (PBS, Sigma Aldrich, Germany) to remove planktonic cells, before treating the biofilms with various concentrations of i) Deferiprone ("Def"; 3-hydroxy-1,2-dimethylpyridin-4(1H)-one, Sigma Aldrich, Germany), ii) Gallium-Protoporphyrin ("GAPP"; Frontier Scientific, UT, USA), iii) a concurrent combination of both compounds and iv) a consecutive combination of both compounds. To prepare the treatments, Def was dissolved in water and GaPP was dissolved in an aqueous 0.03% solution of Tween® 80 (polyoxyethylene sorbitan monolaurate, Sigma Aldrich, Germany), i.e. above the critical micelle concentration (CMC) of Tween® 80 (0.015%). Controls included bacterial wells without treatment (i.e. 100% bacterial growth, negative control), blank wells without bacteria (i.e. 0% growth, positive control) and bacterial wells with Tween® 80 treatment (as a control for GaPP dilutions). After 2 hours incubation of each treatment at 37° C. on a rotating plate, a second washing step with PBS followed to remove the treatments.

All experiments were performed as triplicates on individual plates with at least 4 wells per treatment.

(iii) Viability Assessment

Bacterial viability was assessed using the AlamarBlue cell viability assay as described in Peeters, E. et al. (2008) *Journal of Microbiological Methods*, 72(2): p. 157-165. A 10% AlamarBlue dilution (Resazurin, Life Technologies, Australia) in nutrient broth was prepared and added to each well. Plates were incubated in the dark at 37° C. on a rotating plate. Fluorescence of Resorufin was measured hourly on a FLUOstar OPTIMA plate reader (BMG LABTECH, Germany). The method was set at bottom reading and fluorescence was measured at $\lambda_{excitation}$ 530 nm/$\lambda_{emission}$ 590 nm. Maximum intensities were typically reached after 6 hours incubation and used for quantification according to Equation 1:

$$\% BK = \frac{I_C - I_T}{I_C} \times 100\% \quad (1)$$

Bacterial viability was determined as the percentage of biofilm killing (% BK), where $I_C$ represents the fluorescence intensity of the controls (i.e. 100% bacterial growth) and $I_T$ indicates the maximum intensity of the treatments. Both $I_C$ and $I_T$ were corrected by the intensity of background (i.e. 0% bacterial growth).

(iv) Minimal Inhibitory Concentration (MIC)

MIC values were assessed for the individual compounds Def and GaPP against planktonic *S. aureus* using standard methods, specifically colony suspension method and broth microdilution as described in Wiegand, I. et al. (2008) *Nat Protoc*, 3(2): p. 163-75. Briefly, single colonies of *S. aureus* ATCC 25923 were suspended in 0.45% saline and adjusted to 0.5 McFarland units. The bacterial suspension was 1:100 diluted with nutrient broth and plated into 96-well plates. Various treatment dilutions of Def and GaPP were added, followed by incubation of the plate at 37° C. for 20 hours. The MIC was determined as the lowest drug concentration preventing turbidity.

(v) Human Cell Culture

L929 cells (mouse fibroblast cell line) and Nuli-1 cells (human airway epithelial cell line) were obtained from ATCC (American Type Culture Collection, Manassas, Va., USA). The Nuli-1 cell line was cultured in Bronchial Epithelial Cell Growth Medium (Lonza, Australia) and L929 cells were grown in Dulbecco's Modified Eagle Medium (Sigma-Aldrich, Germany). Cells were maintained in a fully humidified incubator with 5% CO2 at 37° C.

(vi) Cell Viability Test

The lactate dehydrogenase (LDH) bioassay (Roche Diagnostics Corporation, Indianapolis, Ind., USA) was performed to assess the cytotoxic effects of Def and GaPP. Briefly, cells were seeded at $1\times10^4$ into each well in 100 µl in quadruplicate wells of 96-well flat-bottom plates and incubated for 24 hours (37° C., 5% $CO_2$) to allow attachment of cells. To assess the toxicity of the dual treatment, firstly, 100 µl of Def (20 mM) was added to each well. After 2 hours incubation, cells were washed three times with PBS and were exposed to different concentrations of GaPP (100, 200, 300, 400 and 500 µg/ml) for another 2 hours. In addition, cells were separately treated with either Def or GaPP for 2 hours. The OD was measured at 490 nm.

(vii) Statistics and Software

Results were statistically analysed using one-way ANOVA and unpaired t-test (GraphPad Prism version 6.00 for Windows, GraphPad Software, La Jolla, Calif., USA) and statistical significance inferred at $p<0.05$.

Results (i) Efficacy Studies

The following results of in vitro efficacy studies indicate the percentage of biofilm killing relative to controls, inferring 0% biofilm killing for negative controls (i.e. 100% bacterial growth) and 100% biofilm killing for positive controls (i.e. 0% bacterial growth). Controls for GaPP treatments (i.e. aqueous 0.03% solution of Tween® 80) revealed no significant anti-biofilm activity (data not shown).

(ii) Single Treatments

*S. aureus* biofilms were treated for 2 hours with various concentrations of Def ranging from 0.5 to 50 mM. As depicted in FIG. 1A, the percentage of biofilm killing significantly increased with higher Def concentrations, however, at concentrations above 20 mM the biofilm reduction plateaued at approximately 34%.

When *S. aureus* biofilms were exposed for 2 hours to GaPP at different concentrations (1 to 200 µg/ml), the compound demonstrated significant efficacy in a dose dependent manner. The highest concentration (200 µg/ml) killed approximately 77% of *S. aureus* biofilms (see FIG. 1B).

(iii) Dual Treatments

For the evaluation of a treatment combining Def and GaPP, the drug concentrations were chosen in accordance with the most effective single treatment concentrations (i.e. Def concentration 20 mM, GaPP concentration 200 µg/ml). The efficacy of the dual treatment against *S. aureus* biofilms was assessed in 2 ways.

Figure 2:
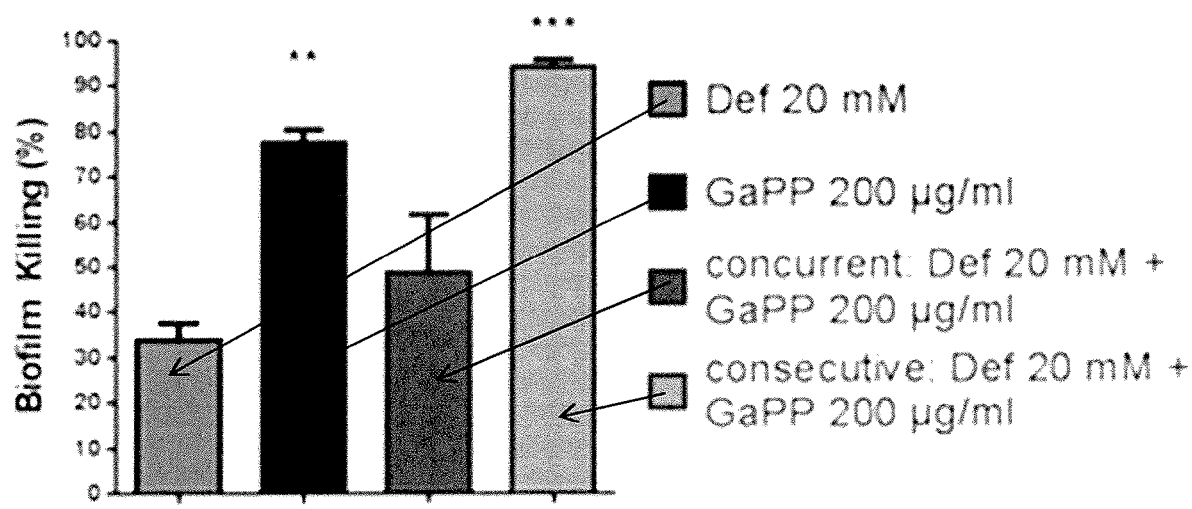
FIG. 2 shows GaPP treatment and dual treatments compared to Def treatment. (a) Def 20 mM, (b) GaPP 200 µg/ml, (c) concurrent: Def 20 mM+GaPP 200 µg/ml, (d) consecutive: Def 20 mM+GaPP 200 µg/ml. Incubation time 2 h for: Def (20 mM), GaPP (200 µg/ml) and the concurrent dual treatment. Incubation time for the consecutive dual treatment: 2 h Def followed by 2 h GaPP. The values indicate mean±SD of 3 individual plates with 4 wells for each treatment, n=12. Statistical analysis: one-way ANOVA.  $p<0.01$ * $p<0.001$

Firstly, both compounds were applied together as a concurrent treatment and incubated for 2 hours. The concurrent treatment removed approximately 48% of *S. aureus* biofilms as shown in FIG. 2. However, this result was not significantly higher than the single Def treatment ($p>0.05$), but significantly lower than the single GaPP treatment ($p<0.05$) and the consecutive dual treatment ($p<0.01$).

Secondly, *S. aureus* biofilms were exposed to a consecutive treatment of 2 hours Def followed by 2 hours GaPP. This consecutive treatment eradicated *S. aureus* biofilms almost completely (approximately 94% biofilm killing, see FIG. 3) and showed superior efficacy against *S. aureus* biofilms. The consecutive treatment was significantly different from the single treatments of Def ($p<0.001$) and GaPP ($p<0.05$) and the concurrent dual treatment ($p<0.01$).

(iv) Effects of Consecutive Dual Treatments

In order to investigate the power of consecutive dual treatments, studies were performed with lower Def concentrations of 0.5, 1.5, 5, 10 and 20 mM, and GaPP concentrations of 1, 5, 10, 50, 100 and 200 µg/ml (Table 1). The biofilm killing (%) of individual single treatments were added to obtain a theoretical biofilm killing percentage of consecutive dual treatments in an additive effect model. The measured biofilm killing of dual treatments was compared to the theoretical biofilm killing to investigate synergism. According to the calculated difference (i.e. measured biofilm killing−theoretical biofilm killing) the effect of the dual treatments has been classified as:

i) synergistic, if measured biofilm killing>theoretical biofilm killing ii) additive, if measured biofilm killing=theoretical biofilm killing iii) negative, if measured biofilm killing<theoretical biofilm killing.

Figure 3:
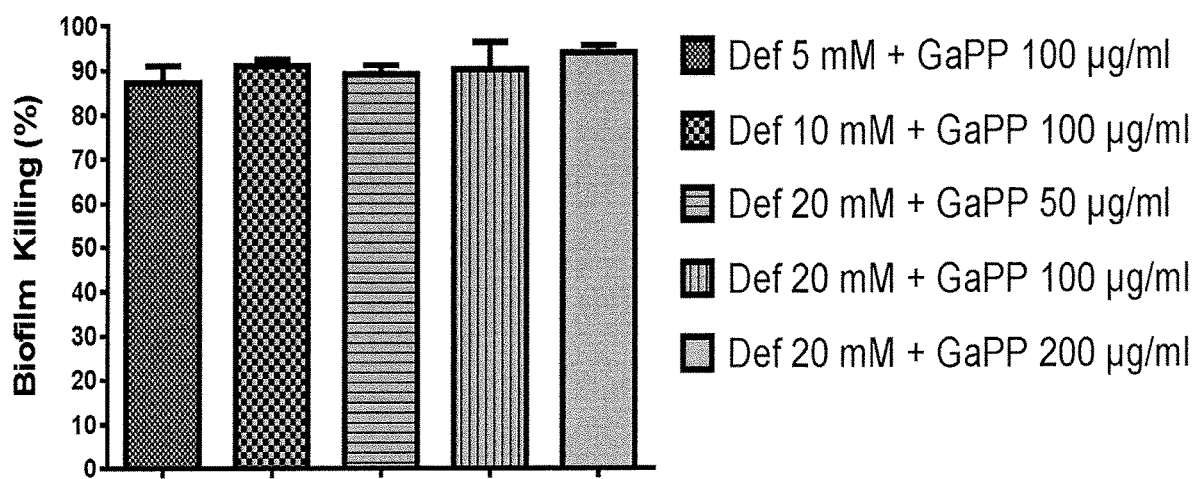
FIG. 3 shows *S. aureus* biofilm killing (%) by consecutive dual treatments. (a) Def 5 mM+GaPP 100 µg/ml, (b) Def 10 mM+GaPP 100 µg/ml, (c) Def 20 mM+GaPP 50 µg/ml, (d) Def 20 mM+GaPP 100 µg/ml, (e) Def 20 mM+GaPP 200 µg/ml. Incubation time 2 h Def followed by 2 h GaPP. The values indicate mean±SD of 3 individual plates with 4 wells for each treatment, n=12.

The best efficacy against *S. aureus* biofilms (biofilm killing activity of >85%) was achieved with consecutive dual treatments depicted in FIG. 3.

(v) Consecutive Dual Treatments with Prolonged Def Exposure

Figure 4:
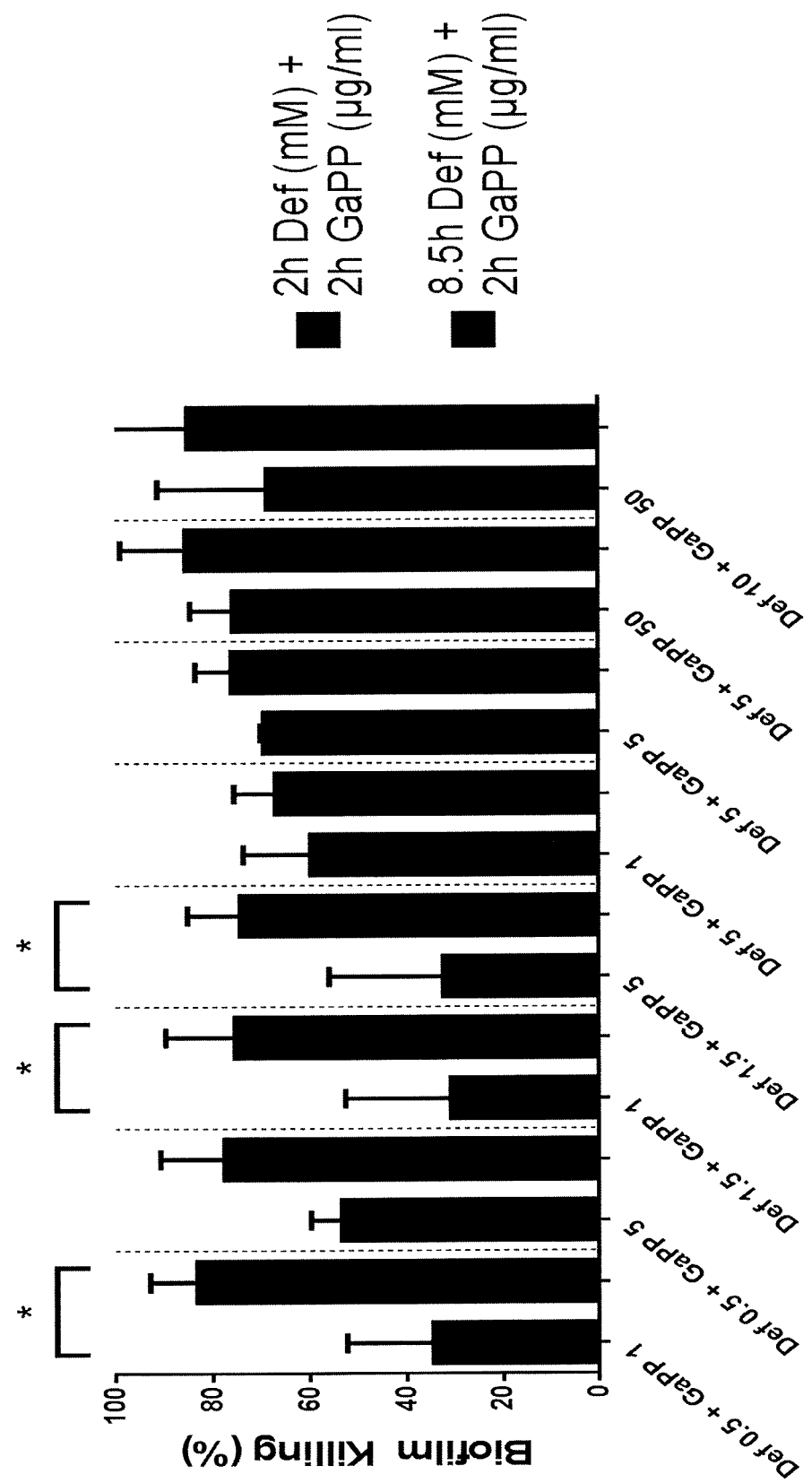
FIG. 4 shows a comparison of consecutive dual treatments with different Def incubation times: 2 h Def followed by 2 h GaPP (black) versus 8.5 h Def followed by 2 h GaPP (grey). The values indicate mean±SD of 3 individual plates with 4 wells for each treatment, n=12. Statistical analysis: unpaired t-test. * $p<0.05$.

The influence of prolonged Def incubation (8.5 hours instead of 2 hours) during a consecutive dual treatment was assessed. Eight different treatment combinations were chosen as model treatments. FIG. 4 compares the efficacy of the model treatments according to two different Def incubation times (i.e. 2 hours versus 8.5 hours) prior to 2 hours GaPP treatment. Treatment with Def for 8.5 hours followed by 2 hours GaPP treatment significantly enhanced the synergistic effect against *S. aureus* biofilms (around 85% biofilm killing) when low Def (up to 1.5 mM) and GaPP (up to 5 µg/ml) concentrations were used.

(vi) Minimal Inhibitory Concentration (MIC)

The MIC of Def was evaluated at 2.5 mM and the MIC of GaPP was 0.4 µg/ml against planktonic *S. aureus* ATCC 25923 (results not shown).

TABLE 1

| Dual treatment | Biofilm killing (%) by single treatment Def | GaPP | Biofilm killing (%) by Def + GaPP Theory | Measured | Difference (%) | Effect |
|---|---|---|---|---|---|---|
| Def 0.5 + GaPP 1 | 6.09 | 9.04 | 15.13 | 34.43 | 19.30 | Synergistic |
| Def 0.5 + GaPP 5 | | 32.18 | 38.27 | 53.34 | 15.07 | Synergistic |
| Def 0.5 + GaPP 10 | | 41.99 | 48.08 | 69.65 | 21.57 | Synergistic |
| Def 0.5 + GaPP 50 | | 52.90 | 58.99 | 61.14 | 2.15 | Additive |
| Def 0.5 + GaPP 100 | | 69.86 | 75.95 | 58.37 | −17.58 | Negative |
| Def 0.5 + GaPP 200 | | 77.61 | 83.7 | 68.53 | −15.17 | Negative |
| Def 1.5 + GaPP 1 | 7.65 | 9.04 | 16.69 | 30.69 | 14.00 | Synergistic |
| Def 1.5 + GaPP 5 | | 32.18 | 39.83 | 32.32 | −7.51 | Additive |
| Def 1.5 + GaPP 10 | | 41.99 | 49.64 | 47.59 | −2.05 | Additive |
| Def 1.5 + GaPP 50 | | 52.90 | 60.55 | 41.74 | −18.81 | Negative |
| Def 1.5 + GaPP 100 | | 69.86 | 77.51 | 66.52 | −10.99 | Negative |
| Def 1.5 + GaPP 200 | | 77.61 | 85.26 | 74.94 | −10.32 | Negative |
| Def 5 + GaPP 1 | 12.07 | 9.04 | 21.11 | 59.67 | 38.56 | Synergistic |
| Def 5 + GaPP 5 | | 32.18 | 44.25 | 69.86 | 25.61 | Synergistic |
| Def 5 + GaPP 10 | | 41.99 | 54.06 | 62.15 | 8.09 | Synergistic |
| Def 5 + GaPP 50 | | 52.90 | 64.97 | 75.77 | 10.80 | Synergistic |
| Def 5 + GaPP 100 | | 69.86 | 81.93 | 87.29 | 5.36 | Additive |
| Def 5 + GaPP 200 | | 77.61 | 89.68 | 74.50 | −15.18 | Negative |
| Def 10 + GaPP 1 | 22.88 | 9.04 | 31.92 | 53.58 | 21.66 | Synergistic |
| Def 10 + GaPP 5 | | 32.18 | 55.06 | 47.21 | −7.85 | Negative |
| Def 10 + GaPP 10 | | 41.99 | 64.87 | 54.46 | −10.41 | Negative |
| Def 10 + GaPP 50 | | 52.90 | 75.78 | 68.72 | −7.06 | Negative |
| Def 10 + GaPP 100 | | 69.86 | 92.74 | 91.05 | −1.69 | Additive |
| Def 10 + GaPP 200 | | 77.61 | >100 | 79.25 | −20.75 | Negative |
| Def 20 + GaPP 1 | 34.00 | 9.04 | 43.04 | 41.80 | −1.24 | Additive |
| Def 20 + GaPP 5 | | 32.18 | 66.18 | 52.22 | −13.96 | Negative |
| Def 20 + GaPP 10 | | 41.99 | 75.99 | 75.64 | −0.35 | Additive |
| Def 20 + GaPP 50 | | 52.90 | 86.9 | 89.21 | 2.31 | Additive |
| Def 20 + GaPP 100 | | 69.86 | >100 | 90.24 | −9.76 | Additive |
| Def 20 + GaPP 200 | | 77.61 | >100 | 94.03 | −5.97 | Additive |

Comparison of the *S. aureus* biofilm killing (%) by single treatments and consecutive dual treatments of various drug concentrations. The theoretical biofilm killing (i.e. biofilm killing single treatment Def + single treatment GaPP) is compared with the measured biofilm killing of dual treatments. According to the calculated difference (i.e. measured biofilm killing − theoretical biofilm killing) the effect of the dual treatment has been classified. The values indicate mean (without SD for better readability) of 3 individual plates with 4 wells for each treatment, n = 12.

Overall, dual treatments with low concentrations of both Def and GaPP resulted in synergistic anti-biofilm effects, as the measured biofilm killing was significantly higher ($p<0.05$) than the theoretical biofilm killing. Additive effects were accomplished with high concentrations of both Def and GaPP.

(vii) Cytotoxicity Studies

Single Treatments

Figure 5:
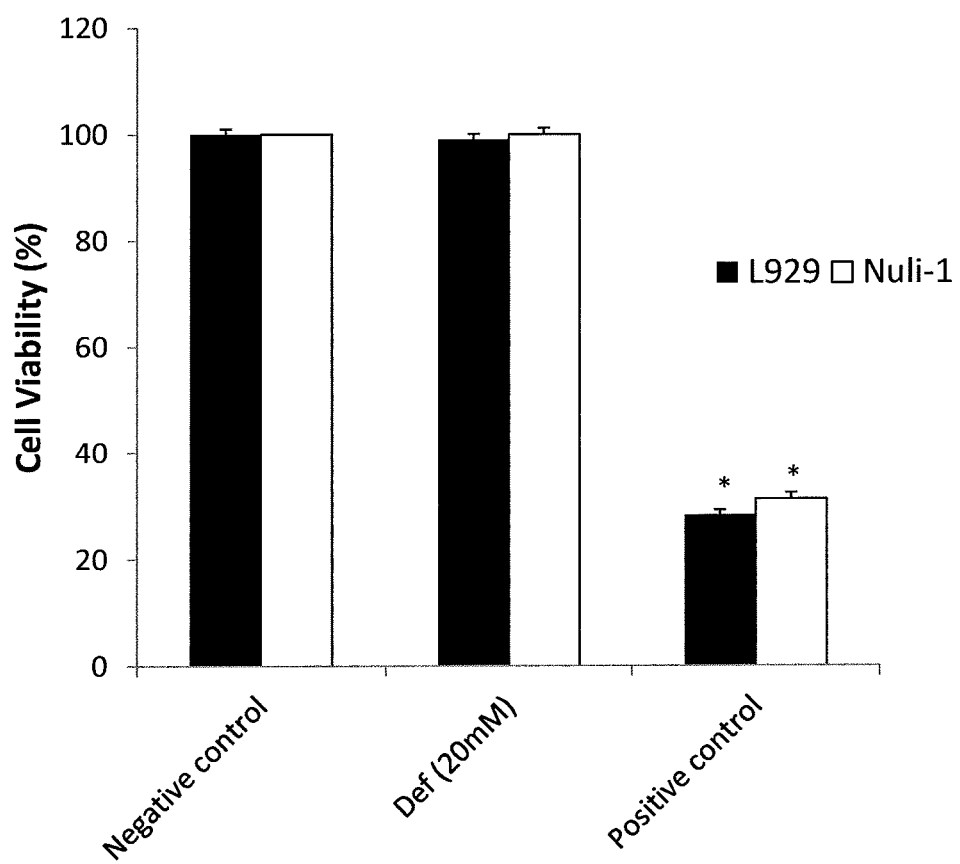
FIG. 5 shows cell viability (%) of L929 (black) and Nuli-1 (grey) cell lines estimated by the LDH assay in 96-well plates following 2 h exposure to Def (20 mM). Data is shown as relative surviving cell numbers (%) compared to the negative control (no treatment). The values indicate mean±SEM of 3 individual plates with 3 wells for each treatment, n=9. Statistical analysis: one-way ANOVA. * $p<0.05$.
Figure 6:
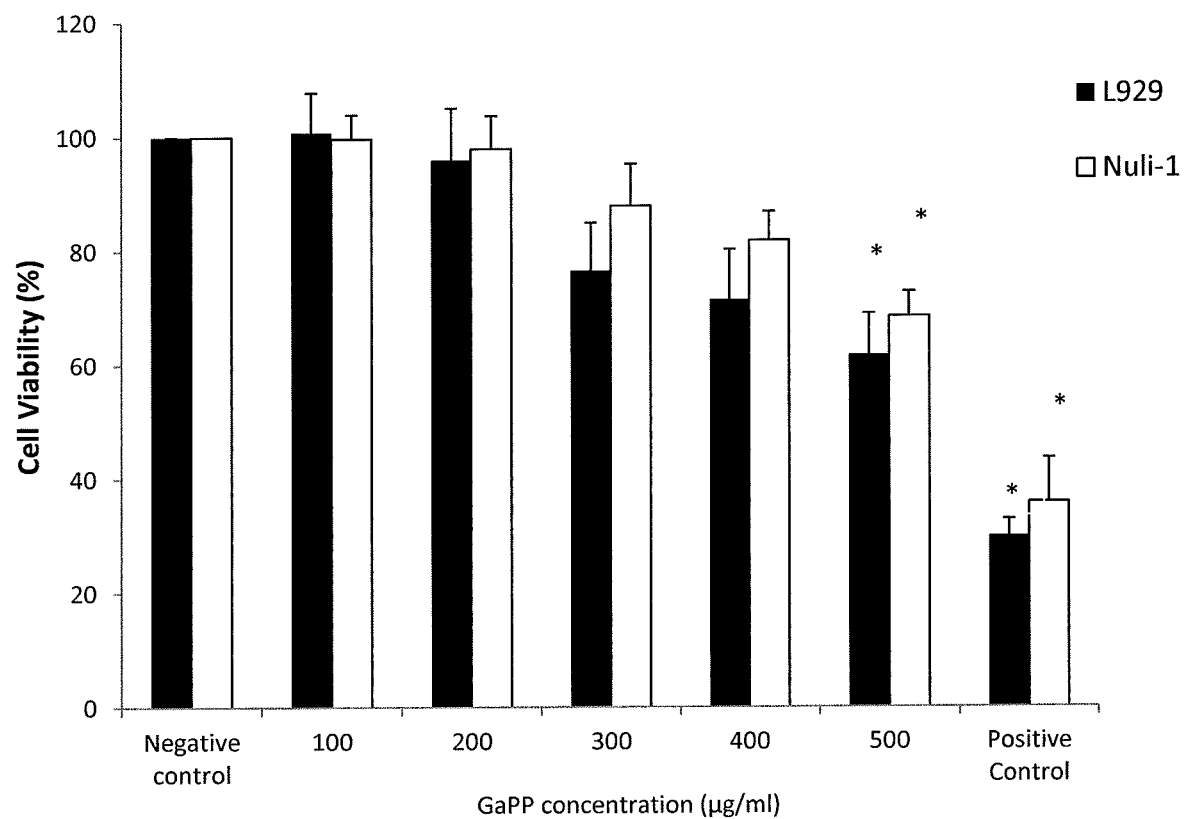
FIG. 6 shows cell viability (%) of L929 (black) and Nuli-1 (grey) cell lines estimated by the LDH assay in 96-well plates following 2 h exposure to GaPP. Data is shown as relative surviving cell numbers (%) compared to the negative control (no treatment). The values indicate mean±SEM of 3 individual plates with 3 wells for each treatment, n=9. Statistical analysis: one-way ANOVA. * $p<0.05$.

Induction of cell hazard was determined by the LDH assay. Def (20 mM) as single treatment was tested on L929 and Nuli-1 cell lines and no statistically significant difference ($p>0.05$) was observed (FIG. 5). Similarly, single treatment with GaPP had no significant effect on both cell lines at concentrations ranging from 100-400 µg/ml. Only the highest concentration of 500 µg/ml GaPP induced cell toxicity on both cell lines (FIG. 6).

Dual Treatment

Figure 7:
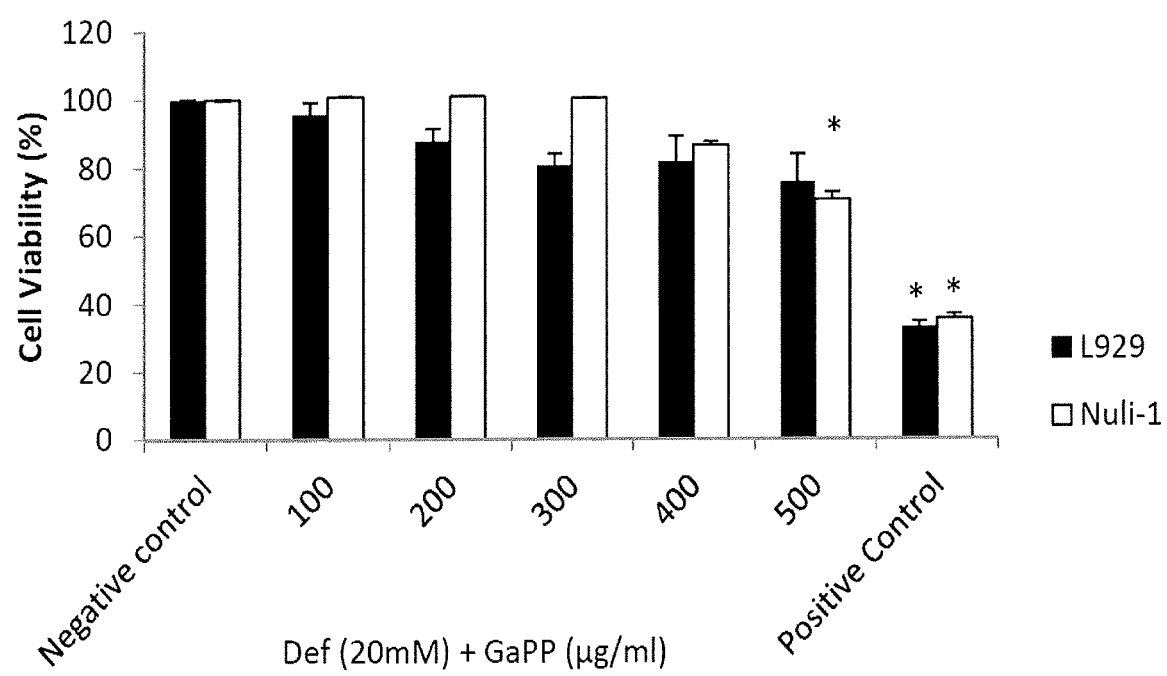
FIG. 7 shows cell viability (%) of L929 (black) and Nuli-1 (grey) cell lines estimated by the LDH assay in 96-well plates following 2 h exposure to Def (20 mM) and then 2 h exposure to GaPP. Data is shown as relative surviving cell numbers (%) compared to the negative control (no treatment). The values indicate mean±SEM of 3 individual plates with 3 wells for each treatment, n=9. Statistical analysis: one-way ANOVA. * $p<0.05$.

L929 cells were not sensitive to any of the tested concentrations in consecutive treatments with Def and GaPP (FIG. 7). In the Nuli-1 cell line, treatment with Def and GaPP reduced viability at the concentration of 500 µg/ml GaPP (FIG. 7).

DISCUSSION

Bacterial biofilms represent a major challenge for current medical therapies, as bacteria residing in biofilms are able to evade the host's immune system, quickly adapt to environmental conditions and easily establish resistance against medical treatments. Due to the emergence and spread of bacterial resistance over the past decades antibiotics became increasingly less effective, hence, there is an ongoing demand for novel treatment strategies. One approach is to target the bacterial iron metabolism, as iron is essential for bacterial growth and pathogenesis, particularly for S. aureus.

During a S. aureus infection, nutrients (especially iron) are consumed by bacteria and become limited with progression of the infection and proliferation of bacteria. S. aureus adapts to the iron deprivation by up-regulation of iron transporter proteins on the surface membrane. The iron-regulated surface determinant system (Isd) and the haem transport system (Hts) are specialised systems efficiently securing iron supply by sequestering haem from the host. After haem is taken up by bacteria, it can be i) enzymatically degraded to release free iron as nutrient source, ii) incorporated as enzyme cofactor for respiratory proteins on the membrane surface, or iii) in the case of haem accumulation, carried out of the bacterial cells by efflux pumps to prevent haem intoxication.

In this study a novel treatment combination interfering with the bacterial iron metabolism was examined using the two compounds Deferiprone (Def) and Gallium-Protoporphyrin (GaPP). S. aureus biofilms were used to assess the efficacy of treatments with the individual compounds, as well as treatment combinations, while studies with planktonic S. aureus indicated the MIC of the single compounds. Moreover, cytotoxicity studies were conducted with two different cell lines (i.e. L929, Nuli-1) in order to examine safety of the treatments.

In vitro efficacy studies of Def and GaPP on S. aureus biofilms revealed superior efficacy of dual consecutive treatments compared to the individual compounds and dual concurrent treatments, respectively (FIG. 3). We showed that both Def and GaPP as individual treatments demonstrate a dose-dependent anti-biofilm effect, however, none of the individual compounds was able to eradicate S. aureus biofilms (FIG. 1). The antimicrobial activity of Def appears to be the result of iron chelation and nutrient deprivation, while the antimicrobial activity of GaPP may ow to partial interference with cellular pathways inside bacterial cells.

In contrast, the combination of both compounds as a dual consecutive treatment eradicated S. aureus biofilms, hence, demonstrated superior antimicrobial activity. This finding indicated mechanistic effects of each individual compound working synergistically together.

Without being bound by theory, we have interpreted these results as follows: Def as an iron chelator can trigger iron deprivation of S. aureus. In response, bacteria up-regulate iron transporter proteins in order to sequester iron from any available iron source in the environment. When GaPP is introduced, bacteria are likely to take up the compound via iron transporter proteins recognising the haem ring as their preferred iron source. Once GaPP entered the bacterial cells, it is reported to interfere with essential bacterial pathways potentially leading to starvation, limited respiration and introduction of reactive oxygen species (ROS), which ultimately kill the bacteria.

GaPP lacks the oxidation potential of haem, as the gallium ion only exists in the +3 oxidation state, while iron is found as $Fe^{+2}$ and $Fe^{+3}$. After treatment with GaPP, respiratory proteins including membrane-bound cytochromes are incapable of transferring electrons for ATP production, resulting in limited respiration and contributing to the production of ROS. Furthermore, GaPP cannot be cleaved by bacterial enzymes, hence, precluding nutrient/iron release and inducing starvation.

Haem efflux pumps play an important role for S. aureus to regulate the amount of haem inside bacterial cells. Frequently, the highly efficient haem uptake systems overpower the metabolic capability of S. aureus, therefore efflux pumps balance intrabacterial haem levels in order to avoid intoxication by excess haem or haem metabolites. Inhibition of these efflux pumps by GaPP could provoke haem accumulation in S. aureus, which catalyses the generation of toxic oxygen radicals and subsequent DNA and protein damage.

We found that the interacting mechanisms work best, when Def and GaPP were applied as a consecutive treatment. This is hypothesized to be due to the latency for up-regulation of iron transporter proteins after Def treatment. Increased presence of iron transporter proteins would subsequently augment and accelerate GaPP uptake into bacterial cells, where GaPP is effectively inhibiting vital cellular pathways, and ultimately generating toxic oxygen radicals. In contrast, a concurrent treatment lacks the initial time for up-regulation of iron transporter proteins by Def, hence, less GaPP would enter bacterial cells, which might explain the lower efficacy of the concurrent treatment compared to the consecutive treatment. Furthermore, Def is considered to be able to interact with GaPP when both compounds are applied together. The tetrapyrrole backbone of GaPP is a planar structure prone to enable Def access from two sides to interact with the central gallium ion, hence, decreasing the activity of the whole molecule, which is suggested to be the reason for lower efficacy of the concurrent treatment compared to the single GaPP treatment.

In an additional study we extended the incubation time of Def to 8.5 hours (instead of 2 hours), while the consecutive treatment time with GaPP remained the same (2 hours). The results indicated higher efficacy of the consecutive treatment for very low concentrations of Def and GaPP with prolonged Def exposure, likely owing to enhanced up-regulation of iron transporter proteins and subsequently augmented uptake of GaPP. The amount of GaPP entering bacterial cells will have a strong impact on the efficacy of the dual treatment, as GaPP represents the major active compound of the dual treatment being responsible for inhibition of essential bacterial pathways and generation of ROS. Accordingly, up-regulation of iron transporter proteins by Def is a fundamental step for a highly efficient consecutive treatment.

Cytotoxicity studies with two sensitive cell lines (i.e. L929 and Nuli-1 cell lines) were carried out to assess potential cytotoxicity of Def, GaPP and a consecutive dual treatment. No toxicity was examined for the highest drug concentrations used throughout the efficacy studies.

In conclusion, the consecutive dual treatment of Def and GaPP represents a safe and highly efficient novel treatment strategy with promising properties to control *S. aureus* biofilms.

Example 2—Plate Assay for Antibacterial Properties of Combined Def and GaPP

To investigate the anti-bacterial properties of Def and GaPP individually, or with Def and GaPP in combination, a plate assay was used. Briefly, liquid nutrient agar was mixed with an aliquot of a *S. aureus* or *Pseudomonas aeruginosa* overnight culture and poured into Petri dishes. After the agar was solidified, holes (0.9 cm diameter) were punched into the agar and aspirated. Subsequently, the holes were filled with 200 μl of a vehicle with and without Def/GaPP. Following incubation at 37° C. for 24 hours, the inhibition diameter was assessed as a measure of efficacy against *S. aureus* or *Pseudomonas aeruginosa* bacteria.

Figure 8:
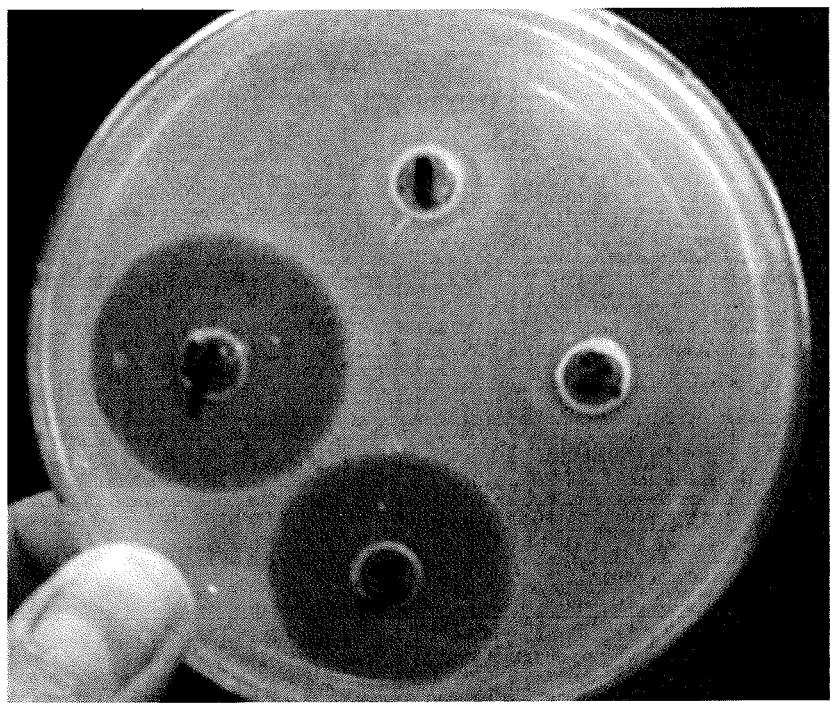
FIG. 8 shows a plate assay to investigate anti-bacterial properties against *S. aureus* of (1) vehicle alone, (2) vehicle with 20 mM Def, (3) vehicle with 200 μg/ml GaPP and (4) vehicle with 20 mM Def and 200 μg/ml GaPP combined.

The inhibition of *S. aureus* is shown in FIG. 8.

As can be seen in the system used, the vehicle alone or with Def had relatively little anti-bacterial activity against *S. aureus*. When GaPP alone was incorporated into the vehicle, the composition showed significant anti-bacterial activity. The combination of Def and GaPP further improved the anti-bacterial activity.

Figure 9:
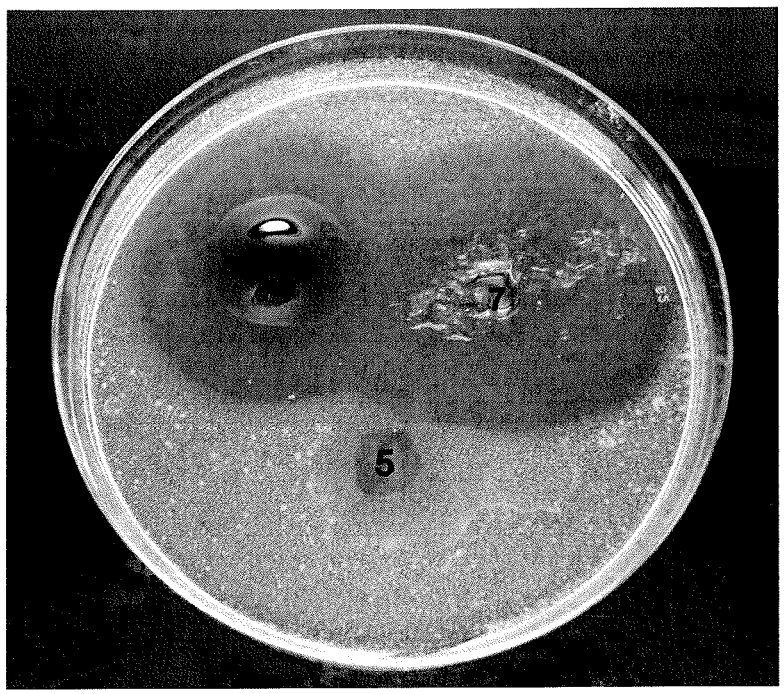
FIG. 9 shows a plate assay to investigate anti-bacterial properties against *Pseudomonas aeruginosa* of (5) vehicle alone, (6) vehicle with 20 mM Def and 200 μg/ml GaPP combined and (7) vehicle with 20 mM Def and 500 μg/ml GaPP combined.

The inhibition of *Pseudomonas aeruginosa* is shown in FIG. 9.

As can be seen in the system used, the vehicle alone had no anti-bacterial activity against *Pseudomonas aeruginosa*, while the combination of Def and GaPP (in two different concentrations) showed significant anti-bacterial activity.

These results demonstrate that the combination of Def and GaPP provided anti-bacterial activity.

Example 3—Treatment of Chronic Rhinosinusitis Using a Combination of Deferiprone and GaPP Our studies support the use of a treatment protocol to apply Def and GaPP consecutively. For the treatment of rhinosinusitis this treatment modality could, for example, be achieved by application of Def and GaPP in nasal spray solutions, douche bottles or nasal irrigations consecutively with a delay in time between consecutive respective applications of Def and GaPP. This time delay could be less or more than 1, 2, 3, 4, 6, 8, 12 hours and could be achieved by delays in application of Def and GaPP in water-based solutions. These solutions may be, for example, isotonic, hypotonic or hypertonic saline solutions.

Alternatively, the treatment combination could be achieved by application of Def and GaPP in a delivery device or formulation that delivers Def faster than GaPP. This could be achieved by application of Def and GaPP incorporated in a single formulation or in another device or formulation that delivers Def faster than GaPP. Another treatment regime would be to deliver Def in a water-based solution together with GaPP, where the GaPP compound is incorporated in a pharmaceutical formulation that allows a delayed delivery of the GaPP compound within the solution.

To test safety and efficacy in vivo, we have established an in vivo animal model (a rhinosinusitis sheep model) for antibiofilm agent testing using the frontal sinuses (Ha K R, Psaltis A J, Tan L, Wormald P J. A sheep model for the study of biofilms in rhinosinusitis. *Am J Rhinol.* 2007 May-June; 21(3):339-45). The optimal dosage of the Def and GaPP compounds will be selected based on in vitro efficacy studies; plus a dosage with double the Def and GaPP concentration to assess a broad safety range. Merino sheep will undergo bilateral frontal trephination (placement of small metal cannulae through a drill hole into both frontal sinuses) under general anaesthesia. The sheep will be housed for a minimum of 2 weeks to allow the devices to heal in place. Sheep will then have Def/GaPP instilled (twice a day for 14 days) in one frontal sinus (4 sheep in each of the groups instilled with (a) Def, (b) GaPP and (c) Def/GaPP concurrently and (d) Def/GaPP consecutively) while the contralateral sinus will receive vehicle control. Sheep will then be euthanized, sinus tissue harvested and assessed macroscopically and microscopically (histopathological analysis and evaluation of ciliary and tight junction morphology, using Scanning Electron Microscopy). General wellbeing of the sheep (appetite, behaviour, weight change) represents the secondary measures. Efficacy study: The 1st stage entails turbinectomy (removal of the middle turbinates, tissue protrusions at the lateral side of both nasal cavities) and ethmoidectomy (removal of ethmoid air cells) to gain convenient access to the frontal sinus ostium. Sheep are then allowed a period of convalescence for minimum 3 weeks. The $2^{nd}$ surgical stage involves frontal sinus mini-trephination (as in the safety study), blocking the frontal sinus ostium with vaseline gauze and instillation of *S. aureus* via the minitrephines into the obstructed frontal sinus. The sheep are monitored for a 7 day incubation period to allow *S. aureus* biofilms to form on the sinus mucosa. On day eight, the ostia are unblocked under sedation and treatment begun. 4 sheep will serve as positive control and euthanized on day 8. The best Def/GaPP combination will be selected based on the results of the safety arm and in vitro studies. Sheep will be given twice daily irrigation through trephines for a period of five days. Right sinuses receive a control flush of 0.9% saline. Within groups (n=4) left sinuses receive either (a) Def (b) GaPP (c) Def/GaPP concurrently and (d) Def/GaPP consecutively. Outcome measures: Once euthanized, mucosal tissue will be harvested from all frontal sinuses, stained for *S. aureus* biofilm using LiveDead Baclight stain and viewed using CLSM. Biofilm quantification will be performed using the software COMSTAT 2 as per our previously validated protocol (Singhal D, Boase S, Field J, Jardeleza C, Foreman A, Wormald P J. Quantitative analysis of in vivo mucosal bacterial biofilms. *Int Forum Allergy Rhinol.* 2012 January-February; 2(1):57-62.). Biofilm biomass (μm3/μm2) of 2 z-stacks taken from each mucosal sample will be averaged, and the results compared for the different treatment arms. Tissue is also assessed for inflammation by staining mucosal sections with Haematoxylin & Eosin and counting inflammatory cells using established protocols our laboratories. For this, three random images will be taken of each sinus and from each image two sections of the epithelial layer (section length of 0.1 mm) and of the sub-epithelial layer are selected (area 0.1 $mm^2$). Within each epithelial section the number of inflammatory cells and goblet cells are counted, and within each sub-epithelial section the number of inflammatory cells are counted. Inflammatory cell counts are divided into two categories; acute (neutrophil and eosinophil cells) and chronic inflammatory cells (lymphocytes, plasma cells, Russell bodies).

Example 4—Treatment of Planktonic Infections Using a Combination of Deferiprone and GaPP To treat planktonic bacterial infections, an intravenous solution or an oral dosage form of an iron chelator such as deferiprone may be administered to a subject suffering from, or susceptible to, a suitable bacterial infection. In this case, a typical administration dosage of the agent is in the range from 25 mg/kg to 33 mg/kg body weight, orally, three times per day, for a total daily dose of 75 mg/kg to 99 mg/kg body weight. The subject may then subsequently be treated, typically 8 to 48 hours later, with a non-iron porphyrin such as GaPP, at a dosage typically in the range from 10 mg/kg to 40 mg/kg as an intravenous or oral dosage form. The treatment may involve withdrawal of treatment with deferiprone when GaPP treatment is commenced, or alternatively treatment with deferiprone may continue and GaPP treatment may subsequently occur in the presence of deferiprone treatment.

Clinical parameters may then be used to assess the efficacy of the treatment regime.

Example 5—Gel Formulation

A hydrogel formulation was prepared as described in WO/200902896 and loaded with 20 mM of deferiprone (3-hydroxy-1,2-dimethylpyridin-4(1H)-one, Sigma Aldrich, Steinheim, Germany) or various concentrations (100, 250, and 500 µg/ml) of gallium-protoporphyrin IX (Frontier Scientific, Logan, Utah, USA) or a combination of both compounds. Controls included drug-free gel and the gel loaded with 5 µg/ml of the antibiotic ciprofloxacin (i.e. 40 times above the MIC for *S. aureus* ATCC 25923).

Drug release: Five millilitre of gel was prepared in a Falcon tube and allowed to solidify, after which 10 ml release medium (phosphate buffered saline, Sigma Aldrich) was added. The tube was incubated at 37° C. on a rotating platform for 20 days. Aliquots of 0.5 ml were taken at specific time points (0.5, 1, 2, 8, 16, 24, 48, 72, 96, 120, 170, 220, 290, 460 hours) and replaced with fresh release medium. The concentration of Def and GaPP was quantified by UV-Vis spectroscopy (Evolution 201 UV-Vis Spectrophotometer, Thermo Fisher Scientific, Scoresby, VIC, Australia) at 280 nm and 405 nm, respectively, by interpolating from a standard curve.

Figure 10:
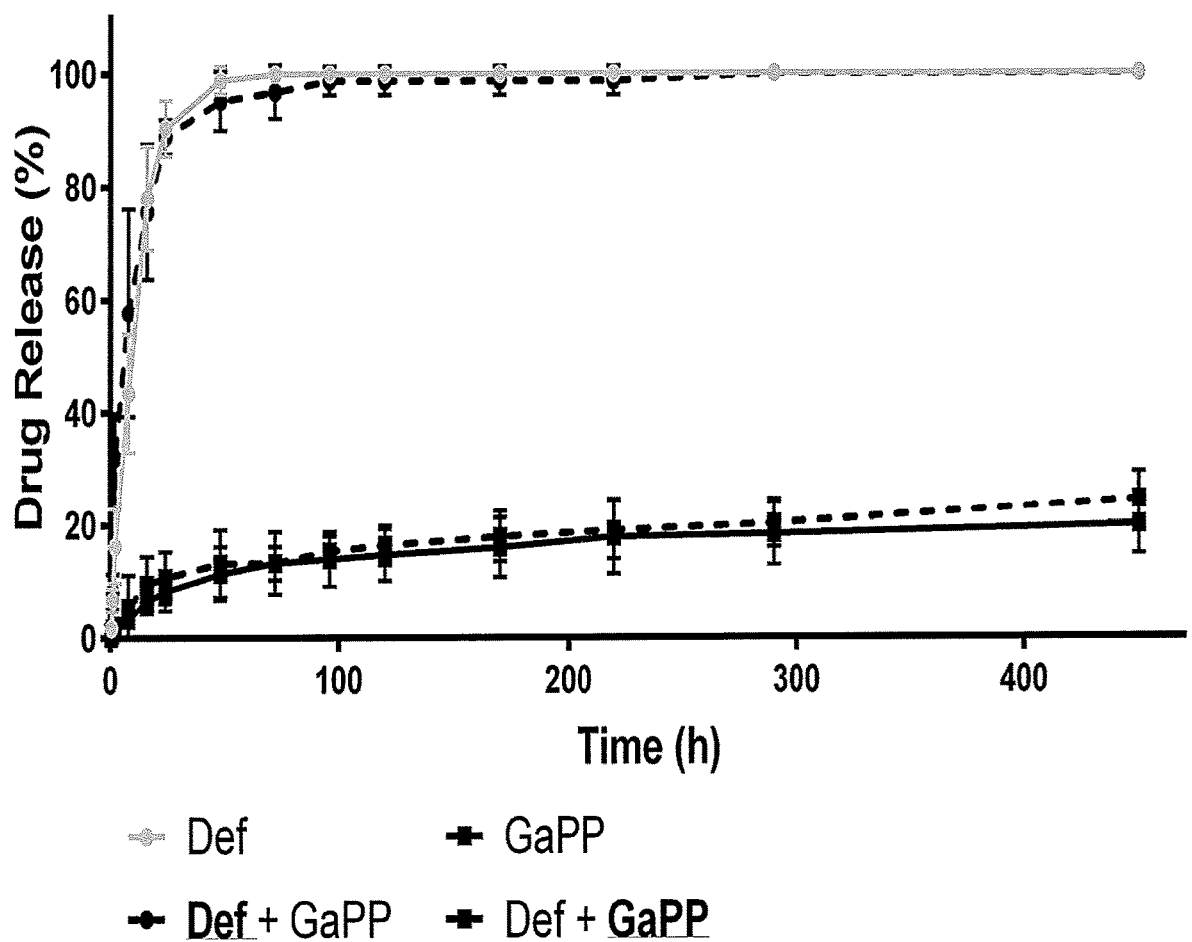
FIG. 10 shows release profiles of gels loaded with 20 mM deferiprone (Def), 250 μg/ml gallium-protoporphyrin (GaPP) or a combination of both. Data are the mean±SD of 3 replicates.

The data is shown in FIG. 10. The concentration of Def and GaPP in the release medium was expressed as a percentage of the original concentration in the gel. The release of Def reached 100% after approximately 48-72 hours, while the release of GaPP gradually increased over time, reaching 20-25% after 460 hours. These release profiles were independent of drug concentrations in the gels. There was no statistical difference between the release from gels incorporating single compounds and the release of the corresponding drug from the combination gel.

The hydrogel formulation provides a drug-delivery-system combining both compounds to facilitate a quick release of Def while enabling the sustained release of GaPP. Def as a water-soluble drug was completely released within 48-72 hours, while the low water-solubility of GaPP caused a gradual release over time driven by diffusion. In our experimental system, the total amount of GaPP released from the hydrogel was limited (approximately 25% of the incorporated GaPP was released after 20 days).

Example 6—Combination Treatment of Planktonic *S. aureas* and MRSA

Bacterial strains: *S. aureus* ATCC 25923 was purchased from American Type Culture Collection (Manassas, Va., USA). Clinical MRSA isolate strains were obtained from Adelaide Pathology Partners (Mile End, SA, Australia). The specimens derived from chronic rhinosinusitis patients and encoded resistance from 4 to up 9 antimicrobials (i.e. penicillin, oxacillin, erythromycin, clindamycin, trimethoprim, tetracycline, amoxicillin/clavulanic acid, cephalexin and ciprofloxacin).

Three-week-old gel formulation as described in Example 5 containing solubilised Def and GaPP was used to assess the minimal inhibitory concentrations (MI against planktonic *S. aureus* ATCC 25923 and 5 clinical MRSA isolates (holding resistance to up to 9 antibiotics) as described in Wiegand I, Hilpert K, Hancock R E. "Agar and broth dilution methods to determine the minimal inhibitory concentration (MIC) of antimicrobial substances" *Nat Protoc* 2008; 3:163-75. Treatment concentrations were calculated based on the release profile and ranged from 0.02 to 8 mM Def and 0.01 to 25 µg/ml GaPP; the control included ciprofloxacin in the range from 0.02 to 5 µg/ml. The MIC was evaluated as the lowest drug concentration preventing bacterial growth.

The MICs against planktonic *S. aureus* ATCC 25923 and 5 different planktonic clinical MRSA isolate strains are depicted in Table 2, showing minimal inhibitory concentrations of deferiprone (Def), gallium-protoporphyrin (GaPP), a combination of both compounds and the antibiotic-control ciprofloxacin (CIP) against planktonic *S. aureus* and MRSA strains. In brackets: number of antibiotics the strain is resistant to.

TABLE 2

|  | S. aureus 25923 | MRSA a (4) | MRSA b (4) | MRSA c (5) | MRSA d (7) | MRSA e (9) |
| --- | --- | --- | --- | --- | --- | --- |
| Def (mg/l) | 28 | 56 | 56 | 56 | 56 | 56 |
| GaPP (mg/l) | 0.90 | 1.48 | 0.74 | 1.48 | 1.48 | 1.48 |
| Combination (GaPP mg/l) | 0.69 | 1.39 | 0.69 | 1.39 | 1.39 | 1.39 |
| CIP (mg/l) | 0.125 | 0.25 | 0.125 | 0.5 | 2.0 | 4.0 |

Example 7—Anti-Biofilm Efficacy Studies

Materials and Methods

Bacterial strains: *S. aureus* ATCC 25923 was purchased from American Type Culture Collection (Manassas, Va., USA). Clinical MRSA isolate strains were obtained from Adelaide Pathology Partners (Mile End, SA, Australia). The specimens derived from chronic rhinosinusitis patients and encoded resistance to up to 9 antimicrobials (i.e. penicillin, oxacillin, erythromycin, clindamycin, trimethoprim, tetracycline, amoxicillin/clavulanic acid, cephalexin and ciprofloxacin).

Hydrogel was prepared as described in Example 5.

Colony Biofilm Model: Biofilm Culture Conditions and Treatment

Single colonies of *S. aureus* ATCC 25923 and a clinical MRSA isolate strain (holding resistance to 5 antibiotics)

were immersed in 0.9% saline (Sigma Aldrich) and adjusted to 1.0±0.1 McFarland units (3×108 colony forming units (CFU)/ml). Following a 1:1000 dilution in nutrient broth (Oxoid Ltd., Basingstoke, UK), 1 µl of the bacterial suspension was spotted on a Whatman® Cellulose Nitrate Membrane Filter (0.2 µm pore size, 25 mm diameter, GE Healthcare Ltd., Little Chalfont, UK) placed on nutrient agar.21, 22 Biofilms were grown for 24 hours at 37° C., before transferring the filters onto nutrient-poor AB trace agar (minimal growth agar including 0.5% glucose as carbon source and 0.5% peptone as amino acid source). The colony biofilms were then covered in 100 µl treatment and incubated for 5 days at 37° C. The filters were transferred onto new AB trace agar after 2.5 days. Finally, bacteria were extracted from the filter-grown biofilms by vortexing and sonication, diluted and spot plated on nutrient agar to assess the treatment efficacy by counting CFU.

Punch Agar Model: Biofilm Culture Conditions and Treatment

An overnight culture of *S. aureus* ATCC 25923 and the clinical MRSA isolate strain encoding for resistance to 5 antibiotics was adjusted to 7.0 McFarland units using 0.9% saline. Twenty microliter of the adjusted overnight culture was suspended in 25 ml liquid nutrient agar (40° C.) and poured into a petri dish. After the agar solidified, cavities of 0.9 cm diameter were punched and the agar was aspirated. The cavities were filled with 200 µl of formulation and the bacterial inhibition diameter was measured after 24 hours incubation at 37° C.

Biofilm Visualisation

Colony biofilms were grown on membrane filters and treated using the conditions stated above. Thereafter, biofilms (together with treatment and membrane) were fixed in 2.5% glutaraldehyde solution (Sigma Aldrich) and incubated with live/dead BacLight stain (SYTO 9/propidium iodide, Life Technologies, Scoresby, VIC, Australia) in the dark. This was followed by fixation in 10% neutral buffered formalin (Sigma Aldrich) for 24 hours at 4° C. and transfer to 70% ethanol. Biofilms were then dehydrated in an ascending ethanol series (80%, 85%, 90%, 95%, 100% ethanol) and cross-sectioned before embedding in paraffin wax. Sections of 3 µm were cut (Microtome HM 325, Thermo Fisher Scientific) and placed on adhesive Superfrost glass slides (Grale HDS, Ringwood, VIC, Australia). Subsequently, sections were deparaffinised and rehydrated prior to analysis by confocal laser scanning microscopy (LSM 710, Carl Zeiss, Jena, Germany) using a 63×/1.4 oil objective. The excitation/emission wavelengths of the BacLight staining were 485/530 nm and 485/630 nm, respectively.

To correlate confocal microscopy images with scanning electron microscopy images (MERLIN, Carl Zeiss) using Zeiss' shuttle and find software, additional samples were prepared as above. After deparaffinisation and rehydration, samples were incubated with osmium tetroxide (ProSciTech, Townsville, QLD, Australia) followed by an ethanol series and subsequent hexamethyldisilazane incubation (ProSciTech). Finally, samples were sputter-coated with 10 nm gold particles (ANFF-SA, Mawson Lakes, SA, Australia).

Statistics and Software

All experiments were conducted in triplicate and are presented as mean±standard deviation (SD).

Results were analysed using one-way ANOVA with Dunnett's test (GraphPad Prism version 6.00 for Windows, GraphPad Software, La Jolla, Calif., USA). Statistical significance was assessed at the 95% confidence level.

Results

Colony Biofilm Model

Figure 11:
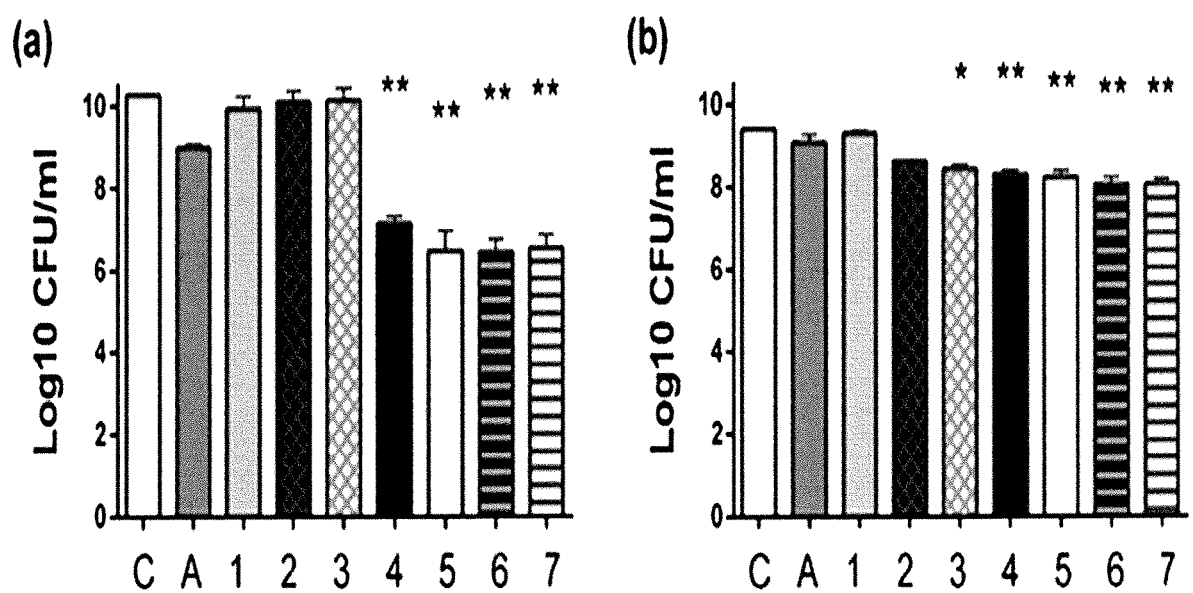
FIG. 11 shows treatment efficacy against (A) *S. aureus* biofilm and (B) MRSA biofilm after 5 days exposure relative to antibiotic-loaded control gel. C: drug-free control, A: antibiotic-loaded control (ciprofloxacin 5 μg/ml), 1: Deferiprone 20 (Def in mM), 2: Gallium-protoporphyrin 100 (GaPP in μg/ml), 3: Def 20+GaPP 100, 4: GaPP 250, 5: Def 20+GaPP 250, 6: GaPP 500, 7: Def 20+GaPP 500. Data are the mean±SD of 3 biological replicates. * $p<0.05$ ** $p<0.01$.

The efficacy of the treatments against *S. aureus* biofilms was assessed after 5 days (FIG. 11A). The Def 20, GaPP 100 and Def 20+GaPP 100 gels demonstrated low efficacy against biofilms, showing only a 0.3-, 0.2- and 0.2-fold log 10 reduction in CFU/ml, respectively, compared to the drug-free control. In contrast, the GaPP 250, Def 40+GaPP 250, GaPP 500 and Def 40+GaPP 500 gels demonstrated a 3.1- to 3.8-fold log 10 reduction in CFU/ml (corresponding to up to 99.98% biofilm killing), thereby significantly ($p<0.01$) exceeding the efficacy of the antibiotic-control (1.3-fold log 10 reduction in CFU/ml). When treatments were tested against MRSA biofilms (FIG. 2b), the Def 20, GaPP 100 and Def 20+GaPP 100 gels showed a 0.1-, 0.8- and 1.0-fold log 10 reduction in CFU/ml, respectively, while the GaPP 250, Def 40+GaPP 250, GaPP 500 and Def 40+GaPP 500 gels reduced the log 10 CFU/ml by 1.1- to 1.4-fold (corresponding to up to 96.00% biofilm killing). This efficacy was significantly ($p<0.01$) better than the antibiotic-control (0.3-fold log 10 reduction in CFU/ml). However, the efficacy of all drug-loaded gels that included GaPP concentrations over 250 µg/ml were statistically not different.

Punch Agar Model

Figure 12:
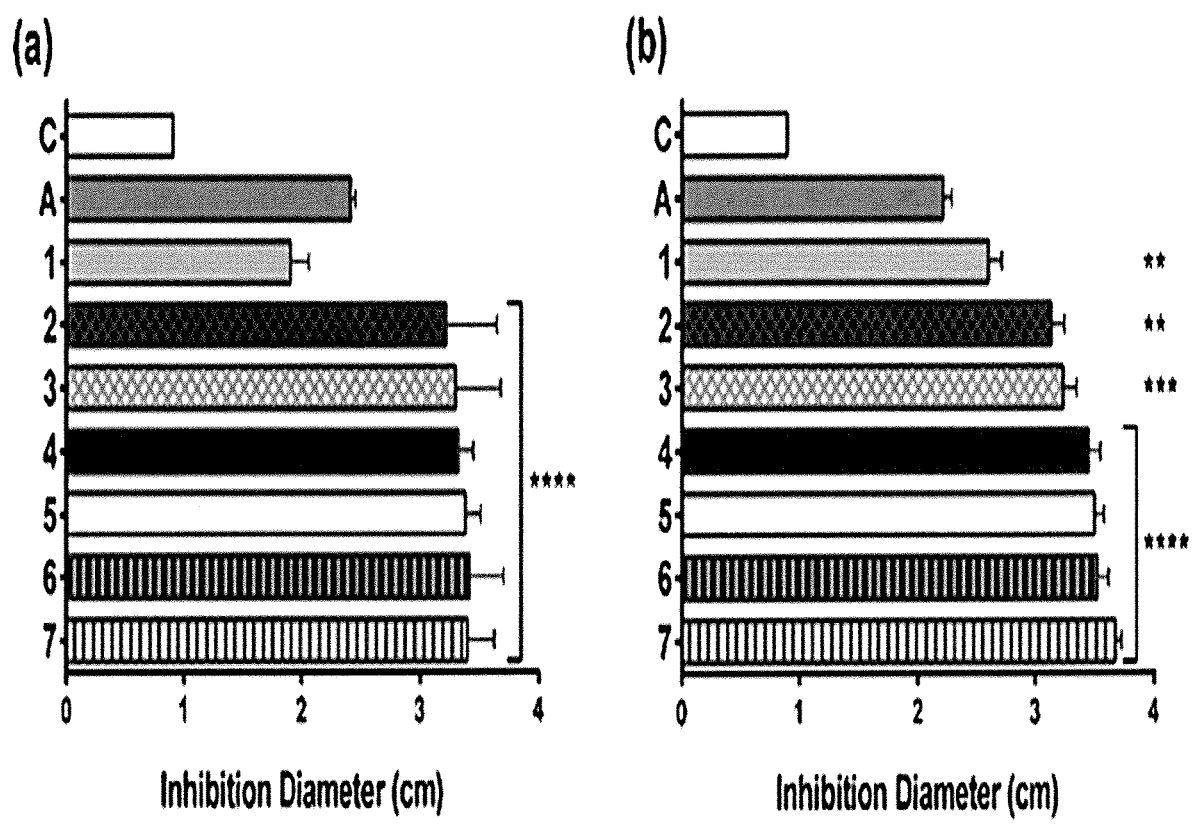
FIG. 12 shows inhibition diameter (cm) of (A) *S. aureus* biofilm and (B) MRSA biofilm after 24 hours treatment exposure relative to antibiotic-loaded control gel. Treatments and concentrations as per FIG. 2. Data are the mean±SD of 3 biological replicates.  $p<0.01$ * $p<0.001$ **** $p<0.0001$.

In this model, assessment of treatment efficacy revealed that the Def gel showed only slight inhibition (1.9 cm diameter) of *S. aureus* biofilm (FIG. 12), while all GaPP gels as well as all combination gels significantly ($p<0.0001$) inhibited biofilm growth (up to 3.4 cm) compared to the antibiotic-loaded gel (2.4 cm). All drug-loaded gels significantly ($p<0.01$ to $p<0.0001$) exceeded the efficacy of the antibiotic-control (2.2 cm inhibition diameter) against MRSA biofilm, inhibiting growth by 2.6 cm (Def), up to 3.5 cm (GaPP) and up to 3.7 cm (Def+GaPP) (FIG. 12).

Biofilm Visualisation

Figure 13:
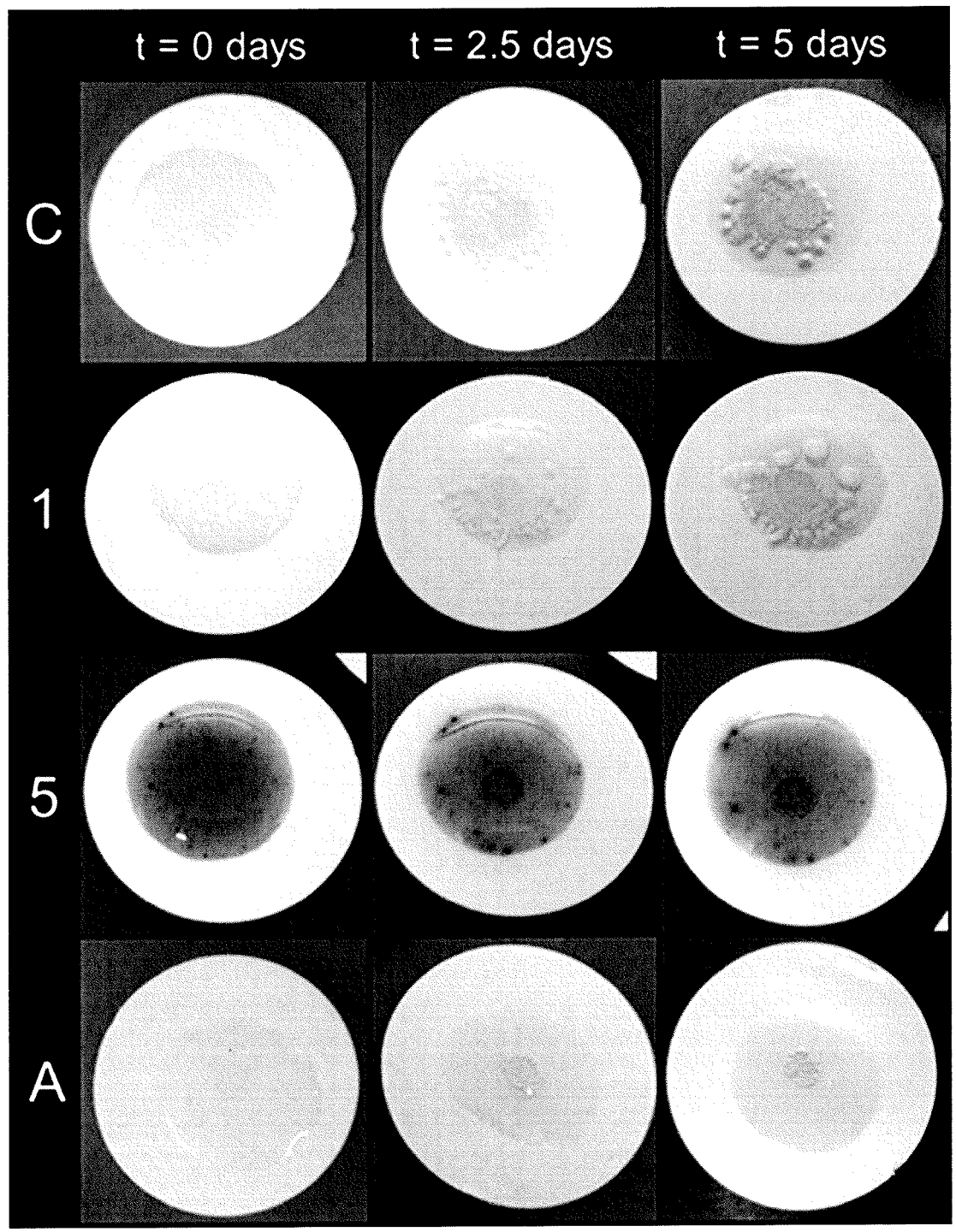
FIG. 13 shows representative examples of *S. aureus* biofilm growth over time.

FIG. 13 depicts examples of *S. aureus* colony biofilms covered in hydrogel. Treatments and concentrations were as per FIG. 10. Macroscopic analysis of biofilm growth over time indicated the efficacy of different treatments. While biofilms grew extensively in the drug-free control and Def gels, a clear anti-biofilm effect was observed for GaPP gel (images not shown), combination gel, and the antibiotic-loaded gel.

Figure 14:
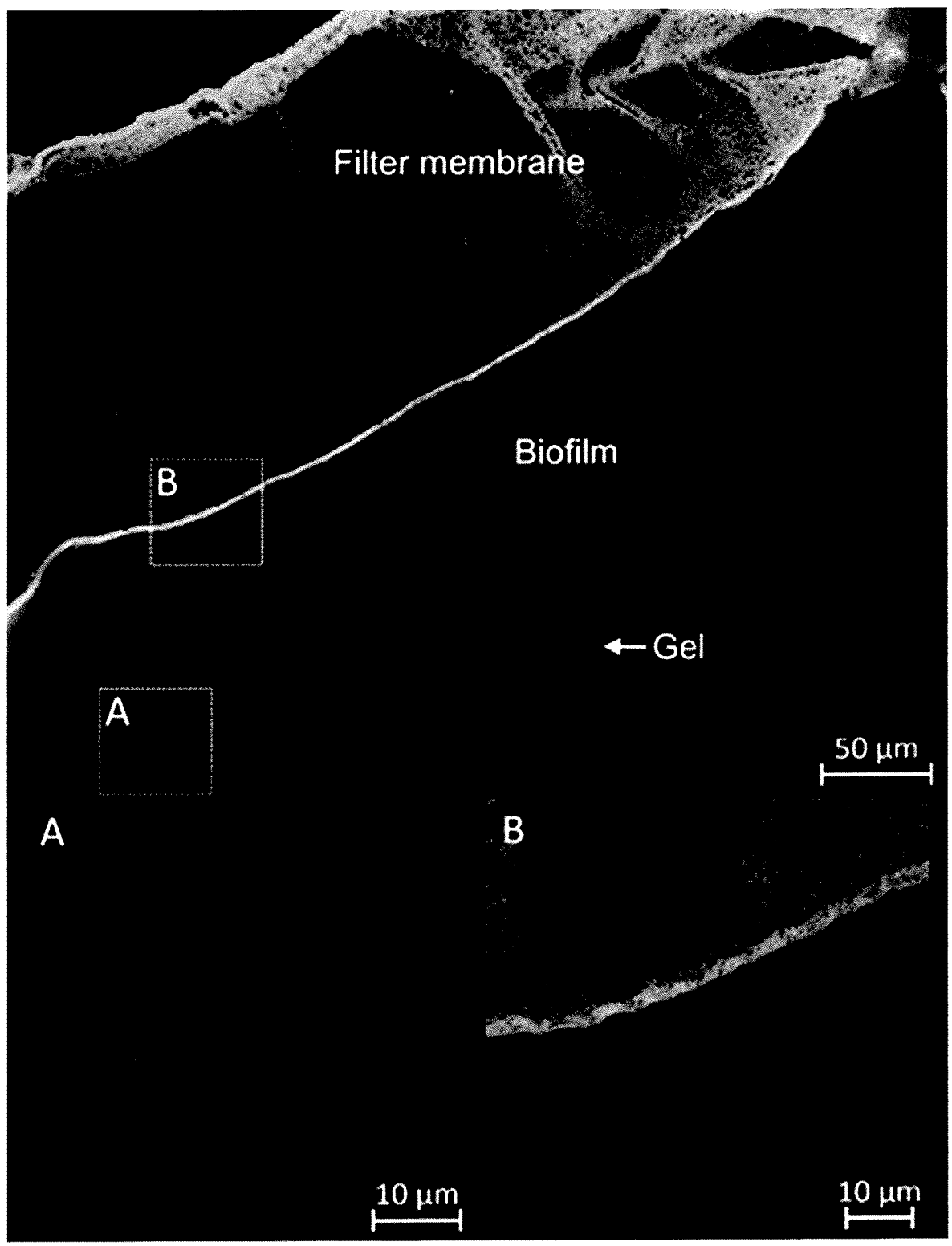
FIG. 14 shows a cross-section of *S. aureus* biofilm treated with Def 20+GaPP 250 gel, stained for live/dead cells and visualised by confocal laser scanning microscopy. The autofluorescent filter membrane is visible under the stained *S. aureus* biofilm and gel.

Confocal laser scanning microscopy with live/dead staining confirmed the efficacy of the drug-loaded gels. FIG. 14 shows a representative cross-section of *S. aureus* colony biofilm after 5 days of treatment with the combination Def 20+GaPP 250 gel. The red staining (propidium iodide) indicates dead bacteria within the biofilm.

Treatment efficacy was further confirmed by correlative light and electron microscopy overlaying confocal and scanning electron microscopy images (data not shown).

DISCUSSION

This study examined the antimicrobial activity of a novel formulation combining the iron-chelator Def and the haem-analogue GaPP. The drug release from a hydrogel was assessed and the efficacy against *S. aureus* and MRSA biofilms was evaluated.

Without being bound by theory, in targeting the bacterial iron metabolism that is particularly vital for growth, survival and pathogenesis of *Staphylococcus* species, Def induces starvation and upregulation of specific iron acquisition systems 2 while GaPP exploits the latter. By mimicking haem (i.e. iron-protoporphyrin), the preferred iron source of *S.*

*aureus*, GaPP is taken up into bacterial cells where it inhibits essential cellular pathways, disrupts the respiratory chain and introduces reactive oxygen species that are toxic to bacteria.

To maximise anti-microbial efficacy, we consider it important for a drug-delivery-system combining both compounds to facilitate a quick release of Def while enabling the sustained release of GaPP. This was accomplished by using a hydrogel as a drug-delivery system.

Anti-biofilm effects against different *S. aureus*, including clinical MRSA isolates, were observed in vitro.

We consider that the use of hydrogels is an approach for some topical applications in clinical practice.

In conclusion, this study evaluated a novel formulation for the topical treatment of *S. aureus* and MRSA biofilms. In vitro studies revealed that a hydrogel incorporating Def and GaPP showed better anti-biofilm efficacy than the antibiotic-control containing ciprofloxacin.

Example 8—Use of Hydrogels Against Biofilms from Various Bacteria

Methods
Bacterial Strains

*Staphylococcus aureus* (ATCC 25923), *Staphylococcus epidermidis* (ATCC 12228), *Acinetobacter johnsonii* (ATCC 17946) was purchased from American Type Culture Collection (Manassas, Va., USA). *Pseudomonas aeruginosa* 01 was received from the School of Molecular Medical Sciences, Centre for Biomolecular Sciences, University of Nottingham, Nottingham, UK. Clinical isolates were obtained from Adelaide Pathology Partners (Mile End, SA, Australia) and included a Methicillin-Resistant *Staphylococcus aureus* strain (derived from a chronic rhinosinusitis (CRS) patient), two *S. aureus* small colony variant (SCV) strains (derived from CRS patients) and a *P. aeruginosa* strain (derived from a cystic fibrosis patient). The MRSA strain showed resistance against 5 antibiotics (i.e. penicillin, oxacillin, amoxicillin/clavulanic acid, cephalexin, erythromycin).

Preparation of Hydrogels

Hydrogels was prepared as described in Example 5 and loaded with 20 mM of deferiprone (Def, 3-hydroxy-1,2-dimethylpyridin-4(1H)-one) and/or various concentrations (100, 250, and 500 μg/ml) of gallium-protoporphyrin IX (GaPP). Controls included drug-free gel and the gel loaded with 5 μg/ml of the antibiotic ciprofloxacin (i.e. 40 times above the MIC for *S. aureus* ATCC 25923). A triple gel comprised of Def 20 mM, GaPP 100 μg/ml and Cip 5 μg/ml was also tested. Ciprofloxacin (Cip) was chosen as antibiotic-control due to its clinical relevance as broad-spectrum therapy against various gram-positive (including *S. aureus*) and gram-negative bacteria that are e.g. associated with infections of the respiratory tract and skin.

Activity in the Colony Biofilm Model

Single colonies of bacteria were immersed in 0.9% saline and adjusted to 1.0±0.1 McFarland units (approx. 3×10⁸ colony forming units (CFU)/ml). Following a 1:1000 dilution in medium (i.e. nutrient broth for *S. aureus*, MRSA, *S. epidermidis, A. johnsonii*; Luria Bertani broth for *P. aeruginosa* and the clinical *P. aeruginosa* isolate, tryptic soy broth for both SCVs), 1 μl of the bacterial suspension was spotted on a Whatman cellulose nitrate membrane filter (0.2 μm pore size, 25 mm diameter, GE Healthcare Ltd., Little Chalfont, UK) placed on agar. Biofilms were grown for 24 hours at 37° C., before transferring the filters onto nutrient-poor AB trace agar (minimal growth agar including 0.5% glucose as carbon source and 0.5% peptone as amino acid source). The colony biofilms were then covered with 100 μl gel (with or without active compounds) and incubated for 5 days at 37° C. The filters were transferred onto new AB trace agar after 2.5 days. Finally, bacteria were recovered from the filter-grown biofilms in PBS by vortexing (1 min) and sonication (15 min in an ice water bath), diluted and spot plated on agar to assess the treatment activity by counting CFU.

Results
Effect of Loaded Hydrogels on Biofilms

FIGS. 15 and 16, and Table 3, show the antibiofilm activity of treatments against various biofilms.

A) The Def 20, GaPP 100 and Def 20+GaPP 100 gels demonstrated low activity against *S. aureus* biofilm, showing 42.96%, 20.37% and 12.96% biofilm reduction, respectively. In contrast, the GaPP 250, Def 40+GaPP 250, GaPP 500 and Def 40+GaPP 500 gels demonstrated 99.91% to 99.98% biofilm reduction, thereby significantly ($p<0.01$) exceeding the activity of Cip gel included as control (94.63% biofilm reduction). The triple gel consisting of Def 20+GaPP 100+Cip showed a substantial antibiofilm reduction of 99.48% being significantly ($p<0.01$) more effective than Cip gel.

B) When MRSA biofilm (clinical isolate derived from a CRS patient) was exposed to the treatments, the Def 20, GaPP 100 and Def 20+GaPP 100 gels showed 18.66%, 82.8% and 88.8% biofilm reduction, respectively, while the GaPP 250, Def 40+GaPP 250, GaPP 500 and Def 40+GaPP 500 gels reduced the biofilm by 91.73% to 95.33%. This reduction was significantly ($p<0.01$) higher than that observed for Cip gel (49.33% biofilm reduction). The triple gel exceeded the antibiofilm activity of all gels tested against MRSA with 99.88 biofilm reduction, which was significantly (better $p<0.0001$) than Cip gel.

C) *P. aeruginosa* biofilm was less affected by Def 20 gel, as well as GaPP 100, GaPP 250 and GaPP 500 gels, showing 78.10%, 77.14%, 89.52% and 95.05% biofilm reduction, respectively. The gels combining Def 20 and GaPP (100. 250 and 500) demonstrated 99.79%, 99.77% and 99.95% biofilm reduction, respectively, being as effective as the Cip gel with 99.95% biofilm reduction. No statistical difference between the combination gels and Cip gel was observed. The triple gel, however, significantly ($p<0.001$) exceeded the Cip gel with a calculated 100% biofilm reduction.

D) A similar treatment efficacy pattern was observed against a *P. aeruginosa* biofilm (derived from a cystic fibrosis patient). The Def 20 gel, GaPP 100, GaPP 250 and GaPP 500 gels showed 96.93%, 78.73%, 99.21% and 99.53% biofilm reduction, respectively, while the combination gels demonstrated higher antibiofilm activity (99.98%, 99.97%, 99.99% biofilm reduction for Def 20+GaPP 100/250/500 gels).

E) Def 20 gel failed to reduce *S. epidermidis* biofilm; in contrast, gels containing GaPP and the combination gels all showed a substantial antibiofilm effect (calculated 99.99%-100% biofilm reduction) which was calculated to be as good as the Cip gel. Only the Def 20+GaPP 250 gel was significantly ($p<0.01$) better than the antibiotic control.

F) The antibiofilm activity of Def 20, GaPP 100, Def 20+GaPP 100 and GaPP 250 gels against *A. johnsonii* biofilm ranged from 90.88% to 98.16% biofilm reduction, all being not statistically different from the Cip gel with 92.63% biofilm reduction. In contrast, Def 20+GaPP 250, GaPP 500 and Def 20+GaPP 500 gels showed significantly ($p<0.05$) higher antibiofilm effects (98.25%–98.05% biofilm reduction) than the antibiotic control gel.

G) The treatment gels showed activity against a SCV (C8) strain of S. aureus (gentamycin induced). While the Def 20 gel promoted SCV biofilm growth, the GaPP 100 and Def 20+GaPP 100 gels showed modest antibiofilm activity (96.86% and 94.91% biofilm reduction, respectively). In contrast, the biofilm reduction of GaPP 250, Def 20+GaPP 250, GaPP 500 and Def 20+GaPP 500 gels was calculated to be 99.99%-100%, thereby significantly (p<0.0001) exceeding the antibiofilm activity of Cip gel (58.17% biofilm reduction). Similar, the triple gel showed with 99.96% biofilm reduction significantly (p<0.001) higher antibiofilm effect than Cip.

H) When tested against another SCV (C12) strain of S. aureus (derived from a CRS patient), neither the Def 20, GaPP 100, Def 20+GaPP 100 nor the Cip gel was able to reduce the SCV biofilm. Gels with higher concentrations of GaPP, i.e. the GaPP 250, Def 20+GaPP 250. GaPP 500 and Def 20+GaPP 500 gels showed with 91.30% to 99.66% biofilm reduction significant (p<0.01) antibiofilm effect compared to the Cip gel (15.74% biofilm reduction). A significant (p<0.0001) antibiofilm activity was achieved with the triple gel (99.92% biofilm reduction).

TABLE 3

| Log10 reduction and corresponding % biofilm reduction of various treatments against biofilms. | | | | | | | | | |
|---|---|---|---|---|---|---|---|---|---|
| | A | 1 | 2 | 3 | T | 4 | 5 | 6 | 7 |
| A) S. aureus | | | | | | | | | |
| Log10 reduction | 1.28 | 0.31 | 0.15 | 0.13 | 2.33 | 3.11 | 3.78 | 3.80 | 3.70 |
| % Biofilm reduction | 94.63 | 42.59 | 20.37 | 12.96 | 99.48 | 99.92 | 99.98 | 99.98 | 99.98 |
| B) MRSA | | | | | | | | | |
| Log10 reduction | 0.32 | 0.09 | 0.77 | 0.96 | 2.94 | 1.09 | 1.17 | 1.36 | 1.35 |
| % Biofilm reduction | 49.33 | 18.67 | 82.80 | 88.80 | 99.88 | 91.73 | 92.93 | 95.33 | 95.33 |
| C) P. aeruginosa | | | | | | | | | |
| Log10 reduction | 3.30 | 0.81 | 0.65 | 2.69 | 4.94 | 1.03 | 2.85 | 1.32 | 3.27 |
| % Biofilm reduction | 99.95 | 78.10 | 77.14 | 99.79 | 100.00 | 89.52 | 99.77 | 95.05 | 99.95 |
| D) P. aeruginosa (cystic fibrosis) | | | | | | | | | |
| Log10 reduction | 5.29 | 1.60 | 0.91 | 3.87 | n/a | 2.11 | 3.87 | 2.64 | 3.95 |
| % Biofilm reduction | 100.0 | 96.93 | 78.73 | 99.98 | n/a | 99.21 | 99.97 | 99.53 | 99.99 |
| E) S. epidermidis | | | | | | | | | |
| Log10 reduction | 3.92 | 0 | 4.24 | 4.48 | n/a | 5.13 | 4.26 | 4.60 | 4.32 |
| % Biofilm reduction | 99.99 | 0 | 99.99 | 100.00 | n/a | 100.00 | 99.99 | 100.00 | 100.00 |
| F) A. johnsonii | | | | | | | | | |
| Log10 reduction | 1.19 | 1.04 | 1.21 | 1.74 | n/a | 1.64 | 1.90 | 1.78 | 1.98 |
| % Biofilm reduction | 92.63 | 90.88 | 93.68 | 98.16 | n/a | 97.56 | 98.74 | 98.25 | 98.95 |
| H) SCV (C8) strain of S. aureus | | | | | | | | | |
| Log10 reduction | 0.41 | 0 | 1.68 | 1.29 | 3.38 | 3.98 | 3.87 | 4.36 | 4.19 |
| % Biofilm reduction | 58.17 | 0 | 96.86 | 94.71 | 99.96 | 99.99 | 99.99 | 100.00 | 99.99 |
| H) SCV (C12) strain of S. aureus | | | | | | | | | |
| Log10 reduction | 0.07 | 0.03 | 0.07 | 0.05 | 3.10 | 1.07 | 1.14 | 1.38 | 2.49 |
| % Biofilm reduction | 15.74 | 6.48 | 13.89 | 9.72 | 99.92 | 91.30 | 92.69 | 95.74 | 99.66 |

A: ciprofloxacin 5 µg/ml,
1: deferiprone 20 (Def in mM),
2: gallium-protoporphyrin 100 (GaPP in µg/ml),
3: Def 20 + GaPP 100,
T: triple gel consisting of Def 20 + GaPP 100 + Cip,
4: GaPP 250,
5: Def 20 + GaPP 250,
6: GaPP 500,
7: Def 20 + GaPP 500.
Data are the mean of 3 biological replicates.

When Def and the lowest concentration of GaPP were combined with Cip as a triple therapy, the treatment exceeded the antibiofilm activity of the individual compounds against biofilms of S. aureus, MRSA, P. aeruginosa and both SCV strains. Accordingly, Def-GaPP is able to potentiate the activity of Cip showing a synergistic antibiofilm effect against various biofilms.

SUMMARY

Def-GaPP gel showed significant biofilm killing compared to the drug-free control and was statistically better than Cip against S. aureus, MRSA and two SCV strains. Against P. aeruginosa, a clinical isolate of P. aeruginosa, S. epidermidis and A. johnsonii the Def-GaPP gel showed significant biofilm killing compared to the blank gel and demonstrated equal antibiofilm activity as Cip (no statistical difference). A triple gel comprising of Def, GaPP and Cip exhibited significant antibiofilm activity against S. aureus, MRSA, P. aeruginosa and both SCV strains, thereby potentiating the antibiotic effect even against resistant strains of MRSA and SCV.

In conclusion, Def and GaPP represent alternative to antibiotic treatments, in particular in light of increasing antibiotic resistance. The combination of Def-GaPP with antibiotics might help to overcome bacterial resistance and increase the susceptibility of pathogens.

Example 9—Treatment of Biofilms in a Rhinosinusitis Model

We used an animal (sheep) model of rhinosinusitis inoculated with S. aureus to study the effect of treatment of a bacterial biofilm in vivo. This sheep model provides an accepted experimental model to study the association between biofilm and sinusitis, as described in Ha, K. R. et al (2007) *American Journal of Rhinology*, 21(3): 339-345.

A total of 23 male merino sheep between 1-2 years of age were used; 8 allocated to the safety arm and 15 in the efficacy arm. For the safety arm, 4 sheep were randomised into each safety group (i) Hydogel (Gel) and (ii) Hydrogel-Deferiprone-Gallium Protoporphyrin (Gel-DG). For the efficacy arm 5 sheep were randomised to each efficacy group (i) Twice daily saline flush (NT), (ii) Hydrogel (Gel) and (iii) Hydrogel Deferiprone-Gallium Protoporphyrin (Gel-DG)

Bacterial inoculum A known biofilm-forming reference strain of S. aureus, American Type Culture Collection (ATCC) 25923 was used. A frozen glycerol stock was defrosted and subcultured overnight in 3 mL of nutrient broth (Oxoid, Adelaide, Australia) on a shaker at 37° C. for 24 hours before being transferred to a 1% nutrient agar plate (Oxoid, Adelaide, Australia). The plate was incubated at 37° C. for 16-18 hours, at which point a single colony forming unit (CFU) was diluted in 0.45% sterile saline to 0.5 McFarland standard and transferred on ice for instillation into sheep sinuses.

Endoscopic sinus surgery. Safety. The sheep underwent bilateral frontal trephination (placement of small metal cannulae through a drilled hole into both frontal sinuses) under general anaesthesia. The sheep were then be housed for a minimum of 2 weeks to allow the devices to heal in place. For the safety study, sheep were instilled in one frontal sinus while the contralateral sinus receives vehicle control. Sheep were then euthanized, sinus tissue harvested and assessed macroscopically and microscopically (histopathological analysis and evaluation of ciliary and tight junction morphology, using scanning electron microscopy). General wellbeing of the sheep (appetite, behaviour, weight change) represents the secondary measures.

For the efficacy study, sheep underwent turbinectomy (removal of the middle turbinates, tissue protrusions at the lateral side of both nasal cavities) and ethmoidectomy (removal of ethmoid air cells) to gain access to the frontal sinus ostium followed by a period of convalescence for minimum 3 weeks. Sheep underwent frontal sinus minitrephination (as in the safety study), blocking the frontal sinus ostium with vaseline gauze and instillation of S. aureus (or P. aeruginosa in a second project) via the minitrephines into the obstructed frontal sinus. According to our well-established sinusitis sheep model, the sheep were monitored for a 7-day period to allow mucosal biofilms to form. On day eight, the ostia were unblocked and treatment begun. Each sheep was assigned into one of three efficacy groups (i) Twice daily saline flush (NT), (ii) gel and (iii) Gel-Deferiprone-Gallium Protoporphyrin (G-DG). For sheep assigned to gel group (ii) and (iii), gel prepared was instilled into each sinus cavity via minitrephines until gel extrusion from frontal sinus ostium was visualised under direct endoscopic visualisation. The minitrephines were then capped. After 24 hours, sinuses were irrigated with 15 mL of sterile normal saline twice a day for the remaining 6 days of treatment. On day 8, all efficacy sheep were euthanized and sinus mucosa harvested.

Hydrogel. The hydrogel was produced as described in Example 5.

All components of the gel were treated for sterility prior to being used in this study. All stocks were stored at room temperature.

Deferiprone and Gallium Protoporphyrin 20 mM Deferiprone (sourced from Sigma-Aldrich, Germany) and 250 µg/mL Gallium Protoporphyrin (sourced from Frontier Scientific, UT, USA). All stocks were stored at room temperature.

Preparation Deferiprone-Gallium Protoporphyrin Gel:

20 mM Deferiprone and 250 µg/mL Gallium Protoporphyrin were diluted in 10 ml of phosphate buffer under sterile conditions the day before. This prepared solution was then used to prepare the hydrogel using sterile technique.

Instillation of Gel into Frontal Sinuses

Gel prepared was instilled into bilateral frontal sheep sinuses via minitrephines while under direct endoscopic visualisation of the anterior ethmoid complex. Sinus cavity was instilled with gel until it was seen to extrude from frontal sinus ostium. The minitrephines were then capped.

Figure 17:
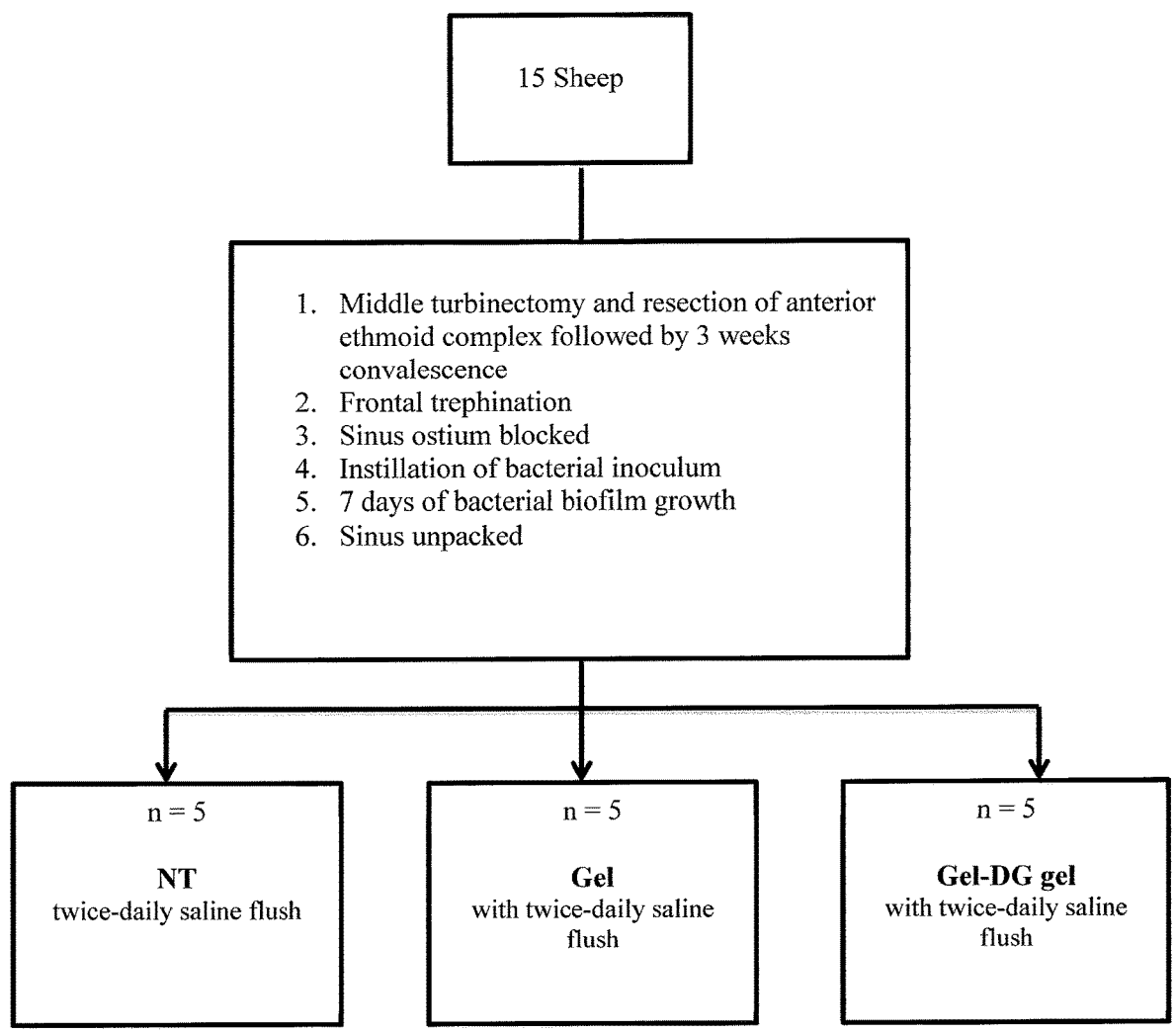
FIG. 17 shows a flow diagram describing efficacy groups and protocol. Each sheep was randomised into (1) Twice daily saline flush (NT), (2) Gel with twice-daily saline flush (Gel), and (3) Gel-DG with twice-daily saline flush respectively. NT=No treatment; Gel=hydrogel; Gel-DG=Hydrogel-Deferiprone-Gallium Protoporphyrin.

Efficacy protocol. The details of the efficacy protocol are shown in FIG. 17.

Histopathology Tissue is assessed for inflammation by histopathology.

Scanning electron microscopy was used to evaluate ciliary and tight junction morphology Biofilm imaging. Once euthanized, mucosal tissue were harvested from all frontal sinuses, stained for biofilms using LiveDead Baclight stain and quantitated using CLSM as per our previously validated protocol.

Statistical analysis was undertaken comparing each treatment side vs. saline side in each of the sheep using paired t-tests. Due to the inherent variability in biofilm growth and extent of inflammation biofilm biomass and inflammation between the different treatment arms must be compared on a logarithmic. This was followed by statistical analysis using 1-way ANOVA. Data transformations were applied as appropriate to better satisfy the assumptions of the statistical models. Analysis was done using R Statistical Software.

Comparison of mucosal biofilms between treatment groups were analysed using Kruskal Wallis 1-way analysis of variance (ANOVA) with Dunn's multiple comparison post test. Statistical significance was considered at 0.05. All statistical tests were done using GraphPad Prism 5.0 software (San Diego, Calif.).

Results

Safety arm. Safety study looking at histopathology and SEM analysis showed no denudation of ciliary morphology when comparing G-DG to gel treated sheep.

Histopathological analysis. There were no significant differences comparing sheep sinus mucosa treated with (A) NT, (B) gel and (C) G-DG gel looking at degree of inflammation, acute inflammation, epithelial thickness, goblet cell hyperplasia, oedema, fibrosis and cilia (preliminary data)

SEM tissue analysis. SEM tissue analysis showed no ciliary denudation when comparing G-DG to Gel treated sheep.

Figure 18:
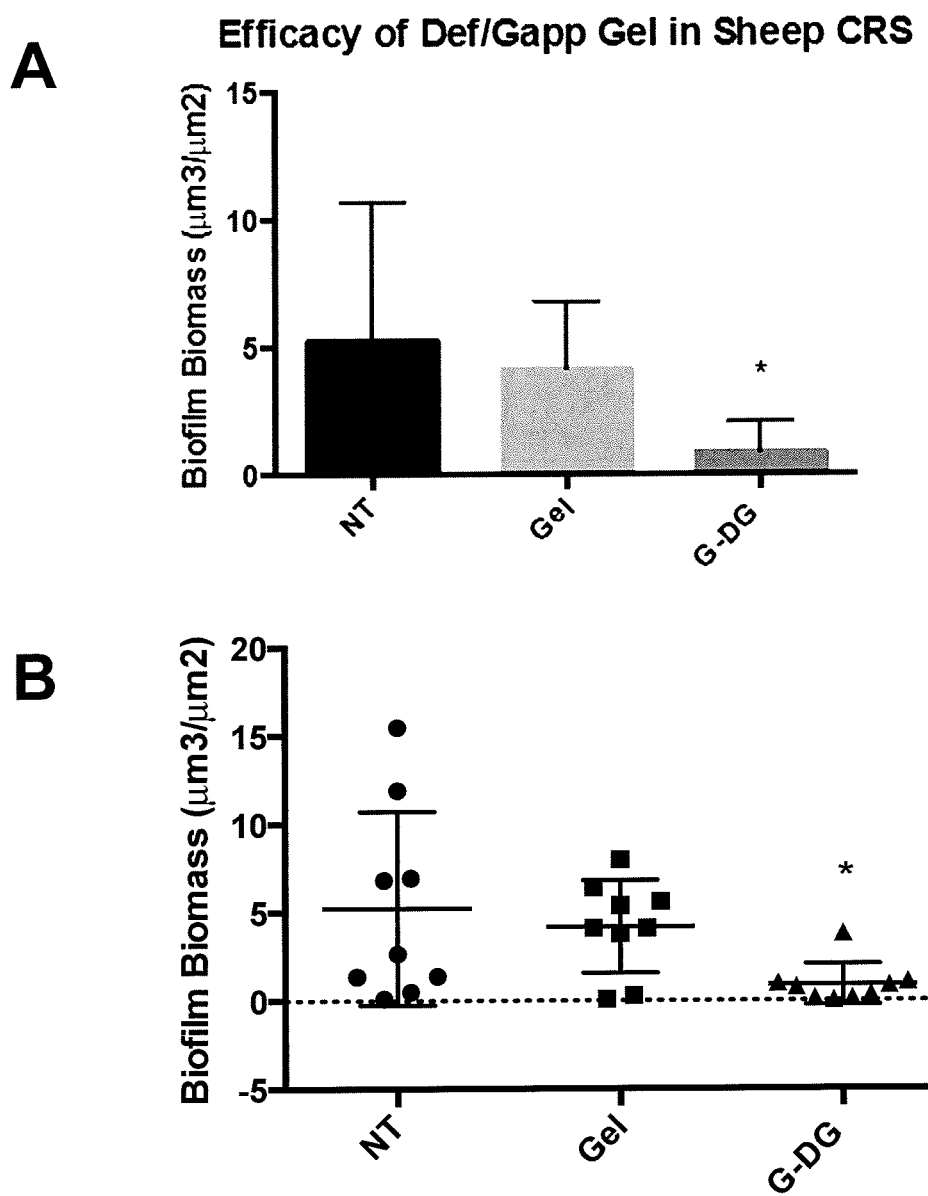
FIG. 18 shows COMSTAT2 assessment of biofilm biomass showed a significant reduction in CD-DG treated sheep compared to NT controls (95% CI [0.3702, 8.278], $p<0.05$, Kruskal Wallis test), but not between NT and CD treated sheep.

COMSTAT2 assessment of biofilm biomass showed a significant reduction in G-DG treated sheep compared to NT controls (95% CI [0.3702, 8.278], p<0.05), but not between NT and gel treated sheep, as shown in FIG. 18.

Although the present disclosure has been described with reference to particular embodiments, it will be appreciated that the disclosure may be embodied in many other forms. It will also be appreciated that the disclosure described herein is susceptible to variations and modifications other than those specifically described. It is to be understood that the disclosure includes all such variations and modifications. The disclosure also includes all of the steps, features, compositions and compounds referred to, or indicated in this specification, individually or collectively, and any and all combinations of any two or more of the steps or features.

Also, it is to be noted that, as used herein, the singular forms "a", "an" and "the" include plural aspects unless the context already dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Reference to any prior art in this specification is not, and should not be taken as, an acknowledgment or any form of suggestion that this prior art forms part of the common general knowledge in any country.

The subject headings used herein are included only for the ease of reference of the reader and should not be used to limit the subject matter found throughout the disclosure or the claims. The subject headings should not be used in construing the scope of the claims or the claim limitations.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Future patent applications may be filed on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the present disclosure. Features may be added to or omitted from the example claims at a later date.

Although the present disclosure has been described with reference to particular examples, it will be appreciated by those skilled in the art that the disclosure may be embodied in many other forms.

The invention claimed is:

1. A method of preventing and/or treating a microorganism infection in a subject, the method comprising administering to the subject an effective amount of an iron chelator and subsequently administering to the subject an effective amount of a non-iron porphyrin, thereby preventing and/or treating the microorganism infection.

2. The method according to claim 1, wherein the iron chelator comprises deferiprone.

3. The method according to claim 2, wherein the method comprises exposing microorganisms associated with the infection to 20 mM or less deferiprone.

4. The method according to claim 1, wherein the non-iron porphyrin comprises a non-iron metalloprotoporphyrin.

5. The method according to claim 4, wherein the non-iron porphyrin comprises a gallium protoporphyrin.

6. The method according to claim 5, wherein the method comprises exposing microorganisms associated with the infection to 200 µg/ml or less of the gallium protoporphyrin.

7. The method according to claim 1, wherein the method comprises administering the non-iron porphyrin to the subject 2 hours or greater after administering the iron chelator to the subject.

8. The method according to claim 1, wherein the microorganism infection comprises a bacterial infection.

9. The method according to claim 8, wherein the administering comprises topical administration of the iron chelator and/or the non-iron porphyrin to the site of bacterial infection.

10. The method according to claim 1, wherein the microorganism infection comprises an infection with a small colony variant of a bacterium, or an antibiotic resistant variant of a bacterium.

11. The method according to claim 1, wherein the microorganism infection comprises an infection associated with a bacterial biofilm.

12. The method according to claim 1, wherein the microorganism infection comprises rhinosinusitis.

13. The method according to claim 1, wherein the microorganism infection comprises an infected wound, a chronic wound, a diabetic wound, a diabetic ulcer, a post-surgery infected wound, an infected wound following abdominal surgery, an implant infection, or a burn injury.

14. A hydrogel composition for the prevention and/or treatment of a bacterial infection in a subject comprising an iron chelator and a non-iron porphyrin, wherein the composition provides an immediate or sustained release of the iron chelator and a delayed release of the non-iron porphyrin.

15. The hydrogel composition according to claim 14, wherein the iron chelator comprises deferiprone.

16. The hydrogel composition according to claim 14, wherein the non-iron porphyrin comprises a gallium protoporphyrin.

17. A method for reducing viability of a microorganism, the method comprising exposing the microorganism to an effective amount of an iron chelator and subsequently exposing the microorganism to an effective amount of a non-iron porphyrin, thereby reducing the viability of the microorganism.

\* \* \* \* \*